US009717761B2

(12) United States Patent
Pitaru et al.

(10) Patent No.: US 9,717,761 B2
(45) Date of Patent: Aug. 1, 2017

(54) STEM CELL-DERIVED NEURAL CELLS FOR CELL THERAPY IN NEUROLOGICAL DISORDERS

(71) Applicant: RAMOT AT TEL-AVIV UNIVERSITY LTD., Tel Aviv (IL)

(72) Inventors: Sandu Pitaru, Ramat Gan (IL); Javier Ganz, Tel Aviv (IL); Daniel Offen, Kfar Haroeh (IL); Eldad Melamed, Tel Aviv (IL)

(73) Assignee: RAMOT AT TEL-AVIV UNIVERSITY LTD., Tel Aviv (IL)

( * ) Notice: Subject to any disclaimer, the term of this patent is extended or adjusted under 35 U.S.C. 154(b) by 336 days.

(21) Appl. No.: 14/359,623

(22) PCT Filed: Nov. 21, 2012

(86) PCT No.: PCT/IL2012/050471
§ 371 (c)(1),
(2) Date: May 21, 2014

(87) PCT Pub. No.: WO2013/076726
PCT Pub. Date: May 30, 2013

(65) Prior Publication Data
US 2014/0335059 A1    Nov. 13, 2014

Related U.S. Application Data

(60) Provisional application No. 61/561,955, filed on Nov. 21, 2011.

(51) Int. Cl.
*C12N 5/00* (2006.01)
*A61K 35/30* (2015.01)
*C12N 5/0793* (2010.01)
*C12N 5/079* (2010.01)
*A61K 35/12* (2015.01)

(52) U.S. Cl.
CPC ............ *A61K 35/30* (2013.01); *C12N 5/0619* (2013.01); *C12N 5/0622* (2013.01); *A61K 2035/124* (2013.01); *C12N 2500/38* (2013.01); *C12N 2500/90* (2013.01); *C12N 2501/01* (2013.01); *C12N 2501/11* (2013.01); *C12N 2501/115* (2013.01); *C12N 2501/119* (2013.01); *C12N 2501/13* (2013.01); *C12N 2501/135* (2013.01); *C12N 2501/41* (2013.01); *C12N 2501/415* (2013.01); *C12N 2501/999* (2013.01); *C12N 2506/097* (2013.01)

(58) Field of Classification Search
None
See application file for complete search history.

(56) References Cited

U.S. PATENT DOCUMENTS

| | | | |
|---|---|---|---|
| 3,753,357 | A | 8/1973 | Schwartz |
| 4,199,022 | A | 4/1980 | Hirsch |
| 4,559,298 | A | 12/1985 | Fahy |
| 5,968,829 | A | 10/1999 | Carpenter |
| 6,310,195 | B1 | 10/2001 | Colucci et al. |
| 2005/0032207 | A1 | 2/2005 | Wobus |
| 2006/0211109 | A1 | 9/2006 | Totey |
| 2009/0004736 | A1 | 1/2009 | Reubinoff |
| 2010/0080780 | A1 | 4/2010 | Pitaru |

FOREIGN PATENT DOCUMENTS

| | | |
|---|---|---|
| WO | 0003002 A2 | 1/2000 |
| WO | 03089631 A1 | 10/2003 |
| WO | 2004046348 A1 | 6/2004 |
| WO | 2006134602 A2 | 12/2006 |
| WO | 2007004776 A1 | 1/2007 |
| WO | 2007066338 A1 | 6/2007 |
| WO | 2007142449 A1 | 12/2007 |
| WO | 2008132722 A1 | 11/2008 |
| WO | 2009/150415 A2 | 12/2009 |
| WO | 2009144718 A1 | 12/2009 |
| WO | 2010090843 A2 | 8/2010 |
| WO | 2012009581 A2 | 1/2012 |

OTHER PUBLICATIONS

Arenas "Towards stem cell replacement therapies for Parkinson's disease". Biochem Biophys Res Commun 396:1: 152-156 (2010).
Bahat-Stroomza et al. "Induction of adult human bone marrow mesenchymal stromal cells into functional astrocyte-like cells: potential for restorative treatment in Parkinson's disease". J Mol Neurosci 39:1-2: 199-210 (2009).
Bampton and Taylor "Effects of Schwann cell secreted factors on PC12 cell neuritogenesis and survival". J Neurobiol 63:1: 29-48 (2005).
Barzilay et al., "Adult stem cells for neuronal repair"Isr Med Assoc J 8:1: 61-6 (2006).
Barzilay et al., "Induction of human mesenchymal stem cells into dopamine-producing cells with different differentiation protocols" Stem Cells Dev 17:3: 547-54 (2008).
Blondheim et al. "Human mesenchymal stem cells express neural genes, suggesting a neural predisposition" Stem Cells Dev 15:2: 141-64 (2006).
J. Peter H. Burbach et al. "Molecular programming of stem cells into mesodiencephalic dopaminergic neurons". Trends Neurosci 29:11: 601-3 (2006).
Caiazzo et al., "Direct generation of functional dopaminergic neurons from mouse and human fibroblasts". Nature 476:7359: 224-7 (2011).
Goncalo Castelo-Branco et al."Function of Wnts in dopaminergic neuron development". Neurodegener Dis 3:1-2: 5-11 (2006).

(Continued)

*Primary Examiner* — Blaine Lankford
(74) *Attorney, Agent, or Firm* — Browdy and Neimark, PLLC

(57) ABSTRACT

The present invention provides methods and uses of neural cells differentiated from adult stem cells of the oral mucosa for cell therapy of neurological and psychiatric diseases and disorders. Methods for direction of differentiation of oral mucosal stem cells into neuronal or neuron supporting cells are also provided.

10 Claims, 21 Drawing Sheets

(56) References Cited

OTHER PUBLICATIONS

Chung et al., "Isolation of neural crest derived chromaffin progenitors from adult adrenal medulla". Stem Cells 27:10: 2602-13 (2009).

Da Silva Meirelles et al., "Mesenchymal stem cells reside in virtually all post-natal organs and tissues". J Cell Sci 119:11: 2204-13 (2006).

Dadon-Nachum et al., "Differentiated mesenchymal stem cells for sciatic nerve injury". Stem Cell Rev 7:3: 664-71 (2011).

Dadon-Nachum et al., "Therapeutic effect of myogenic cells modified to express neurotrophic factors in a rat model of sciatic nerve injury". J Stem Cells Regen Med 8:1: 21-7 (2012).

Davies et al., "A multipotent neural crest-derived progenitor cell population is resident within the oral mucosa lamina propria". Stem Cells Dev 19:6: 819-30 (2010).

Diaz-Amarilla et al., "Phenotypically aberrant astrocytes that promote motoneuron damage in a model of inherited amyotrophic lateral sclerosis". Proc Natl Acad Sci U S A 108:44: 18126-31(2011).

Elisabeth Dupin et al. "Neural crest progenitors and stem cells: from early development to adulthood". Dev Biol 366:1: 83-95 (2012).

Dupin et al., "Neural crest progenitors and stem cells". C R Biol 330:6-7: 521-9 (2007).

Fasano et al., "Culture of postnatal mesencephalic dopamine neurons on an astrocyte monolayer". Curr Protoc Neurosci Chapter 3: 3-21 (2008).

Femandes et al., "A dermal niche for multipotent adult skin-derived precursor cells". Nat Cell Biol 6:11: 1082-93 (2004).

Ganz et al., Cell replacement therapy for Parkinson's disease: how close are we to the clinic? Expert Rev Neurother 11:9: 1325-39 (2011).

Angela Gritti "Neuronal-glial interactions in central nervous system neurogenesis: the neural stem cell perspective". Neuron Glia Biol 3:4: 309-23 (2007).

Stefan Hauser et al. "Isolation of novel multipotent neural crest-derived stem cells from adult human inferior turbinate". Stem Cells Dev 21:5: 742-56 (2012).

Hunka "Stem cells of the oral mucosa stay young. Medical News Today". Retrieved from http://www.medicalnewstoday.com/releases/233197.php Hunka G Aug. 24, 2011 (Aug. 24, 2011) (2011).

Mary Hynes et al. "Embryonic stem cells go dopaminergic". Neuron 28:1: 11-4 (2000).

Iancu et al., "Behavioral characterization of a unilateral 6-OHDA-lesion model of Parkinson's disease in mice". Behav Brain Res 162:1: 1-10 (2005).

Idris AM et al., "Characterization of an amorphous deposit in the lamina propria in oral snuff users in the Sudan as collagen". J Oral Pathol Med 27:4: 157-62 (1998).

Izumi et al., "Development and characterization of a tissue-engineered human oral mucosa equivalent produced in a serum-free culture system". J Dent Res 79:3: 798-805 (2000).

Ying Jin et al., "Transplantation of human glial restricted progenitors and derived astrocytes into a contusion model of spinal cord injury". J Neurotrauma 28:): 579-94 (2011).

Barbara Kaltschmidt et al., "Adult craniofacial stem cells: sources and relation to the neural crest". Stem Cell Rev 8:3: 658-71 (2012).

Hyun-Jung Kim "Stem cell potential in Parkinson's disease and molecular factors for the generation of dopamine neurons". Biochim Biophys Acta 1812:1: 1-11 (2011).

Harold K. Kimelberg "Functions of astrocytes and their potential as therapeutic targets". Neurotherapeutics 7:4: 338-53 (2010).

Deniz Kirik et al., "Characterization of behavioral and neurodegenerative changes following partial lesions of the nigrostriatal dopamine system induced by intrastriatal 6-hydroxydopamine in the rat". Exp Neurol 152:2: 259-77 (1998).

Mauriice Kleber et al., "Neural crest stem cell maintenance by combinatorial Wnt and BMP signaling". J of Cell Biol 169:2: 309-320 (2005).

YS Levy et al., "Regenerative effect of neural-induced human mesenchymal stromal cells in rat models of Parkinson's disease". Cytotherapy 10:4: 340-52 (2008).

Olle Lindvall et al. "Stem cells in human neurodegenerative disorders—time for clinical translation?" J Clin Invest 120:1: 29-40 (2010).

Keren Marynka-Kalmani et al., "The lamina propria of adult human oral mucosa harbors a novel stem cell population". Stem Cells 28:5: 984-95 (2010).

John W. McDonald et al., "Transplanted embryonic stem cells survive, differentiate and promote recovery in injured rat spinal cord". Nature Medicine 5:12: 1410-2 (1999).

Ernesto Miquel et al., "Modulation of astrocytic mitochondrial function by dichloroacetate improves survival and motor performance in inherited amyotrophic lateral sclerosis". PLoS One 7:4: e34776 (2012).

Katrin Montzka et al., "Neural differentiation potential of human bone marrow-derived mesenchymal stromal cells: misleading marker gene expression". BMC Neurosci 10: 16 (2009).

Hans W. Muller et al., "Astroglial neurotrophic and neurite-promoting factors". Pharmacol Ther 65:1: 1-18 (1995).

Narihito Nagoshi et al., "Ontogeny and multipotency of neural crest-derived stem cells in mouse bone marrow, dorsal root ganglia, and whisker pad". Cell Stem Cell 2:4: 392-403 (2008).

S. Pitaru et al., "Bone morphogenetic protein 2 induces the expression of cementum attachment protein in human periodontal ligament clones". Connect Tissue Res 43:2-3: 257-64 (2002).

G. Rozas "Drug-free evaluation of rat models of parkinsonism and nigral grafts using a new automated rotarod test". Brain Res 749:2: 188-99 (1997).

Dong Rui "Experimental study on the biological properties and the effects in promoting wound repair of oral mucosal stem cells", China Doctor/Master Dissertations Full-text Database (Doctor), Medical and Health Technology 2006 ; 12: E074-7, ( 2006).

Ofer Sadan et al. "Bone-marrow-derived mesenchymal stem cell therapy for neurodegenerative diseases". Expert Opin Biol Ther 9:12: 1487-97 (2009).

O. Sadan et al., "Mesenchymal stem cells induced to secrete neurotrophic factors attenuate quinolinic acid toxicity: a potential therapy for Huntington's disease". Exp Neurol 234:2: 417-27 (2012).

R. K. W. Schwarting "The unilateral 6-hydroxydopamine lesion model in behavioral brain research. Analysis of functional deficits, recovery and treatments". Progress in Neurobiology 50(2-3): 275-331 (1996).

J.C. Steele et al., "Lingual striated muscle hamartoma or herniation?" J Oral Pathol Med 33:8: 454-5 (2004).

P Stephens et al., "Non-epithelial oral mucosal progenitor cell populations". Oral Dis 13:1: 1-10 (2007).

Szpaderska et al., "Differential injury responses in oral mucosal and cutaneous wounds". J Dent Res 82:8: 621-6 (2003).

Kazutoshi Takahashi et al. "Induction of pluripotent stem cells from mouse embryonic and adult fibroblast cultures by defined factors". Cell 126:4: 663-76 (2006).

Peter Teismann et al., "Pathogenic role of glial cells in Parkinson's disease". Mov Disord 18:2: 121-9 (2003).

Muri Tio et al., "Roles of db-cAMP, IBMX and RA in aspects of neural differentiation of cord blood derived mesenchymal-like stem cells". PLoS One 5:2: e9398 (2010).

Yi Wang et al., "Stem cell transplantation: a promising therapy for Parkinson's disease". J Neuroimmune Pharmacol 2:3: 243-50 (2007).

Jinsong Wang et al., "Stem cells from human-exfoliated deciduous teeth can differentiate into dopaminergic neuron-like cells". Stem Cells Dev 19:9: 1375-83 (2010).

Marius Wering et al., "Neurons derived from reprogrammed fibroblasts functionally integrate into the fetal brain and improve symptoms of rats with Parkinson's disease". Proc Natl Acad Sci USA 105:15: 5856-61 (2008).

Ian Q. Whishaw et al., "Analysis of limb use by control rats and unilateral DA-depleted rats in the Montoya staircase test: movements, impairments and compensatory strategies". Behav Brain Res 89:1-2: 167-77 (1997).

(56) References Cited

OTHER PUBLICATIONS

Darius Widera et al., "Adult palatum as a novel source of neural crest-related stem cells". Stem Cells 27:8: 1899-910 (2009).
N Xiong et al., "VEGF-expressing human umbilical cord mesenchymal stem cells, an improved therapy strategy for Parkinson's disease". Gene Ther 18:4: 394-402 (2011).
Weilan Ye et al., "FGF and Shh signals control dopaminergic and serotonergic cell fate in the anterior neural plate". Cell 93:5: 755-66 (1998).
Chengyun Zheng et al., "VEGF reduces astrogliosis and preserves neuromuscular junctions in ALS transgenic mice". Biochemical and Biophysical Research Communications 363:4: 989-93 (2007).

Figure 2A-F
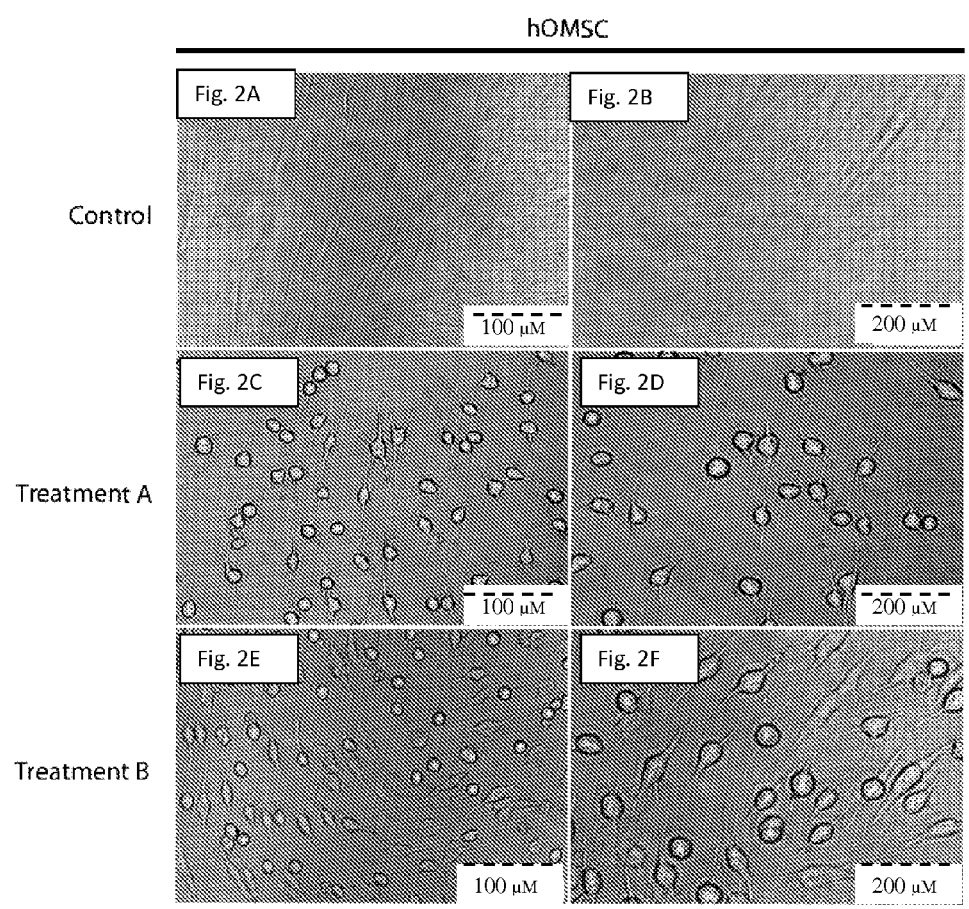

Figure 6A-D
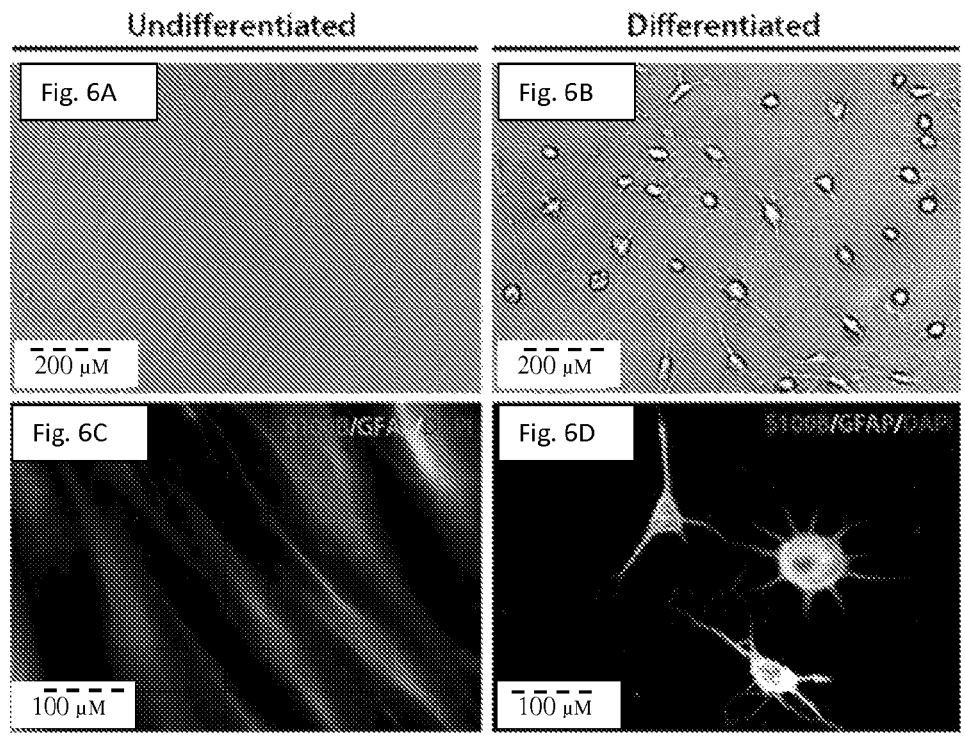

Undifferentiated    Differentiated

STEM CELL-DERIVED NEURAL CELLS FOR CELL THERAPY IN NEUROLOGICAL DISORDERS

FIELD OF THE INVENTION

The present invention is in the field of stem cells and their use is neurological disorders. In particular, the present invention provides an accessible source of adult stem cells from the mucosa of the gastrointestinal track, methods for direction of their differentiation into neural cells and uses of the differentiated cells, particular in cell therapy of neurological and psychiatric diseases and disorders.

BACKGROUND OF THE INVENTION

A goal of regenerative medicine is to regenerate the architecture and function of tissues and organs totally or partially lost due to disease, trauma and ageing. Stem cells are considered crucial building blocks for any regenerative strategy. The challenge and motivation are to find ways for recruiting and/or delivering to the injured site pluripotent stem cells populations capable of regenerating nonfunctional or lost tissues and organs. Bone marrow and to a very limited extent peripheral blood, fat, and muscle are the major sources for such a population. A serious drawback of these sources is that aging and disease substantially lower the functionality and possibly the availability of adult stem cells.

Mesenchymal stem cells (MSCs) were suggested for regenerative therapy in the diseases involving neurodegeneration (Barzilay, R., Levy, Y. S., *Isr Med Assoc J,* 2006, 8, 61-66, Blondheim, N. R., et al., *Stem Cells Dev.,* 2006, 15, 141-164; Sadan, O., Melamed, E. & Offen, D. *Expert Opin Biol Ther.,* 2009, 9, 1487-1497).

Acute or chronic damage to the nervous system includes a variety of conditions such as motion disorders, dissociative disorders, mood disorders, affective disorders, addictive disorders and convulsive disorders. A chronic neurological disease or disorder is for example, Parkinson's disease (PD), multiple sclerosis, epilepsy, amyotrophic lateral sclerosis, glaucomatous neuropathy, Alzheimer's disease and Huntington's disease. Other demyelinating or dysmyelinating disorders, such as Pelizaeus-Merzbacher disease, leukodystrophies, neuritis and neuropathies are also categorized as CNS disorders. An acute neurological disease or disorder is for example stroke or autoimmune encephalomyelitis. A CNS disease or disorder may be a psychiatric disease or disorder such as schizophrenia, anxiety, depression or autism.

US 2006/211109 describes improved methods for efficiently producing neuroprogenitor cells and differentiated neural cells such as dopaminergic neurons and serotonergic neurons from pluripotent stem cells, for example human embryonic stem cells.

Parkinson's disease is a chronic progressive neurodegenerative disease that affects over 1% of the population over 65 years and has been positioned as the second most common neurodegenerative disorder after Alzheimer's Disease. The cardinal symptoms of PD include resting tremor, rigidity, bradykinesia, and postural instability. Advanced symptoms also include non-motor signs such as autonomic, sensory, psychiatric and cognitive impairments (Arenas, E., 2010 *Biochem Biophys Res Commun* 396, 152-156). The clinical motor dysfunction observed in PD is primarily the consequence of a progressive and selective degeneration of dopaminergic (DA) neurons in the substantia nigra pars compacta of the ventral midbrain, resulting in a severe deficiency of dopamine in the nigrostriatal pathway affecting the striatum. Many therapeutic approaches, including cell therapy, have been tested in PD therapy but none was found successful to date. (Lindvall, O. & Kokaia, Z., *J Clin Invest.,* 2010 120, 29-402208).

PD is an attractive model disease to study the effect of direct cell replacement therapy (CRT) by new and healthy neurons (Ganz J, et al., Expert Rev Neurother. 2011; 11:1325-1339 Although this approach was exhaustively investigated, several obstacles have emerged that prevented its wide application in PD therapy.

The progress made in stem cell biology enabled the development of new approaches aimed at coaxing various stem cells to differentiate into DA neurons. These include genetic manipulation and exposure to a variety of morphogenetic factors or chemical compounds. A myriad of stem cell populations have been explored in the search for new DA neuron sources including embryonic, mesenchymal, neural progenitors, induced pluripotent stem cells as well as induced neuronal cells (Wernig M, et al. Proc Natl Acad Sci USA. 2008; 105:5856-5861; Caiazzo M, et al. Nature. 2011; 476:224-227).

Another stem cell based therapy approach currently under research is to use the cells as vectors that contain and secrete neuroprotective or neurotrophic agents, in order to provide neuroprotection or trophic stimuli to the surviving neurons. In the nervous system, the neuroprotective role is mostly played by astrocytes, also called astroglia, which are one of the major types of glial cells and historically have been regarded as the support cells of the nervous system (Kimelberg H K, Nedergaard M. 2010; 7:338-353). Recently malfunction of astrocytes has been proposed to play a role in the pathogenesis of non-cell autonomous diseases (Miguel E, et al. PLoS One. 2012; 7:e34776; Diaz-Amarilla P, et al. Proc Natl Acad Sci USA. 2011; 108:18126-18131).

Neurotrophic factors (NTFs) are naturally occurring polypeptides that support the development, survival and neurite outgrowth in neurons and have been related to neurotransmitter production and release (Gritti A, Bonfanti L. Neuron Glia Biol. 2007; 3:309-323). Several studies concerning neuronal injury have demonstrated that NTFs such as brain-derived neurotrophic factor (BDNF), Vascular endothelial growth factor (VEGF), glial-derived neurotrophic factor (GDNF) and insulin growth factor-I (IGF-1) play an important role in the development, maintenance and regeneration of the nervous system (Dadon-Nachum M, et al. Stem Cell Rev. 2011; 7:664-671; Xiong N, et al. Gene Ther. 2011; 18:394-402). NTFs administration in neuronal dysfunction animal models, for instance, in motor neuron diseases, has been related to axon regeneration and functional recovery (Zheng C, et al. Biochem Biophys Res Commun. 2007; 363:989-993). Although there are some indications of restoration and recovery of motor function, clinical trials of systemic or intrathecal administration of recombinant NTFs to patients with motor neuron disorders did not show significant efficacy, possibly due to NTFs short half-life, poor delivery and low concentrations at target sites. Thus, continuous cellular-derived supply of NTF may overcome this drawback and provide an efficient treatment modality. Transplantation of stem/progenitor cells that mature into astrocytes-like cells in vivo have been reported to improve the outcome of spinal cord injury and ALS symptoms in mice models (Jin Y, et al. J Neurotrauma. 2011; 28:579-594). Genetically modified cells, induced to overexpress NTFs, enhanced nerve regeneration and preserved neuromuscular junctions in motorneuron lesions, such as spinal cord injury and ALS (Dadon-Nachum M et al. Journal of Stem Cells and Regenerative Medicine. 2012; 8:22-26).

It was shown that after a two-step medium based protocol and without transgenes expression, MSCs can be induced into NTFs secreting cells with astrocyte-like characteristics. After transplantation of these cells, clinical symptoms are attenuated in mouse models of multiple sclerosis, Parkinson's disease, Huntington, optic nerve transection and sciatic nerve injury (Sadan O, et al. Exp Neurol. 2012; 234: 417-427). MSC differentiated into astrocyte-like cells, show the ability to protect motorneurons from sciatic nerve injury by preserving rat neuromuscular junctions (NMJ) and by increasing the NTFs levels at the site of injury.

WO2004/046348 teaches differentiation protocols for the generation of neural-like cells from bone marrow-derived stem cells.

WO2006/134602 teaches differentiation protocols for the generation of neurotrophic factor secreting cells.

WO2007/066338 teaches differentiation protocols for the generation of oligodendrocyte-like cells.

WO2009/144718 discloses stem cells having mesenchymal phenotype and increased secretion of brain-derived neurotrophic factor (BDNF). Bone-marrow derived cells, are propagated in platelet lysate prior to differentiation to achieve increases secretion of neurotrophic factors.

WO2010/090843 discloses gingiva-derived mesenchymal stem cells and their use in immunomodulation and reconstruction.

WO 2012/009581 discloses pharmaceutical compositions comprising gingiva-derived mesenchymal stem cells and methods of treating inflammation, wound healing and contact hypersensitivity.

Oral Mucosa Stem Cells

Oral Mucosa is the mucosal lining the oral cavity, namely: the cheeks and the alveolar ridge including the gingiva and the palate, the tongue, the floor of the mouth and the oral part of the lips. Oral mucosa consists of an epithelial tissue of ectodermal origin and the lamina propria (LP) which is a connective tissue of ectomesenchymal origin. Similarly to the ectomesenchymal origin of connective tissues in the oral cavity, cells of the oral mucosa lamina propria (OMLP) originate from the embryonic ectodermal neural crest. Wounds in human oral mucosa heal mainly by regeneration. The rate of healing is faster than that in the skin or other connective tissues and seems to be affected negligibly by age and gender (Szpaderska, A. M., et al., *J Dent Res*, 2003, 82, 621-626). Recently, the first evidence that the OMLP gives rise to a robust multipotent SC population was provided suggested the human oral mucosa as a novel source for therapeutic adult SC (Marynka-Kalmani, K., et al., *Stem Cells*, 2010, 28, 984-995). They also reported that explantation of the adult human OMLP reproducibly generates trillions of SC that they called, human oral mucosa stem cells (hOMSC). Immunophenotyping of hOMSC revealed a primitive neural crest stem cells (NCSC) phenotype, which is not affected by adult donor age. The expression of early neural crest stem/progenitor cell markers (Sox2 and p75) in vitro and in vivo points to the neural crest origin of this population. The identification of mRNA for Oct4, Sox2, Myc-c, and Kfl4, the four transcription factors used for induced pluripotent stem cell (iPS) induction (Takahashi, K. & Yamanaka, S. *Cell*, 2006, 126, 663-676) in the human palate cells (Widera, D., et al. *Stem Cells*, 2009, 27, 1899-1910) suggests that OMLP harbors a primitive SC population.

In vitro assays demonstrated that unsorted hOMSC subjected to neuronal differentiation regimens, differentiated into neuroectoderm lineages as evidenced by the decrease in Oct4 and Nanog, increase in MAP2 expression (neural) and the induction of neuritogenesis in PC12 cells, the last being considered a functional assay for glial differentiation (Bampton E T, Taylor J S. J Neurobiol 2005; 63:29-48). Undifferentiated hOMSC however, supported only PC12 cells survival, probably via the secretion of nerve growth factor (NGF) and Fibroblast Growth Factor-2 (FGF-2). In addition, it was shown (Marynka-Kalmani, K., et al., ibid) that hOMSC can differentiate in vitro, into lineages of the three germ layers and after stimulation with dexamethasone, their implantation in vivo resulted in the formation of bilineage mixed tumors consisting of tissues that develop from cranial neural crest cells during embryogenesis. WO 2008/132722 discloses the lamina propria of the mucosa of the gastrointestinal tract and in particular of the oral mucosa, as a source for pluripotent adult stem cells.

There remains an unmet need to provide safe and readily accessible source of stem cells and methods for their differentiation into different types of neural cells. These stem cells should be capable of generating a population that can be expanded in vitro without losing its pluripotency and differentiated into which can be retransplanted into the affected donor to effectively restore neurological functions. Adult stem cells seems to take the lead and are being positioned as a safe alternative deprived from the immunologic, ethical and safety concerns associated with embryonic, fetal and induced pluripotent stem cell (iPS) stem cells.

SUMMARY OF THE INVENTION

Stem cells derived from the lamina propria of the mucosa of the gastrointestinal tract, and specifically stem cells derived from the lamina propria of the oral mucosa (OMSC), are now disclosed as a stem cell population for induction or preservation of neurogenesis, and for therapy in neurodegenerative and psychiatric disorders and in loss of neural tissue due to trauma. The invention is based on the properties of OMSC of neuroectodermal (neural crest) origin and on their capacity to differentiate fully into different neural lineages, applying selective differentiation protocols.

It is herein shown for the first time that a population of cells selected from the group consisting of: undifferentiated, neuron-differentiated or glial-differentiated OMSC have the potential to restore particular affected systems in neurological and psychiatric diseases and disorders.

Human OMSC (hOMSC), are now shown to be a therapeutic cell population specifically potent to restore neurological disorders. As disclosed herein hOMSC differentiated to dopaminergic neuron-like and glial-like cells through defined protocols provide cell populations useful for restoration of neural function or protection against neural damage.

The present invention provides populations of neural cells differentiated from multipotent stem cells which were obtained or derived from the mucosa of the gastrointestinal tract.

According to the present invention it is disclosed that the oral mucosa contains stem cells that can be readily isolated, maintained in culture, differentiated into neuronal or glial stem cells and used in therapeutic applications.

The present invention provides neural cells differentiated from pluripotent or multipotent stem cells derived from the oral mucosa, and cell populations comprising such cells, for protection against neural damage and treatment of neurological and psychiatric diseases and disorders. Neural cells according to the present invention include neuronal and neuron supporting cells, for example dopaminergic and glial cells respectively. The present invention further provides methods for obtaining such differentiated neural cells methods for maintaining or expanding these cells, and therapeutic uses thereof.

According to one aspect of the present invention, neural cells, differentiated from pluripotent or multipotent stem cells which are derived from the mucosa of the gastrointestinal tract are provided.

According to some embodiments, the pluripotent or multipotent stem cells are derived from the oral mucosa.

According to a specific embodiment the pluripotent or multipotent stem cells are from the lamina propria (LP) of the oral mucosa.

According to a specific embodiment the pluripotent or multipotent stem cells are from the lamina propria (LP) of the gingival oral mucosa.

According to another embodiment the pluripotent or multipotent stem cells are derived from mucosa obtained from the upper part of the gastrointestinal tract.

According to another aspect the invention provides a cell population comprising at least one neural cell differentiated from pluripotent or multipotent stem cells obtained from the lamina propria of the human oral mucosa.

According to some embodiments, the cell population comprises at least 10% neural cells differentiated from oral mucosa stem cells.

According to some embodiments, the cell population comprises at least 20%, 30%, 40%, 50% or 60% neural cells differentiated from oral mucosa stem cells. Each possibility represents a separate embodiment of the present invention.

According to some embodiments the mucosa-derived pluripotent or multipotent stem cells are characterized by expressing at least one embryonic, neural or neural crest stem cell marker which is not expressed constitutively in mesenchymal stem cells or is expressed at very low levels.

According to some specific embodiments, the mucosa-derived stem cells are characterized by expressing at least one neural or neural crest stem cell marker selected from the group consisting of: Snail, Slug, Nestin, p75, TUJ1 (β-TubIII), MAP2, Synapsin and S100β.

According to a more specific embodiment the mucosa-derived stem cells are characterized by expressing a plurality of neural stem cell markers wherein at least one marker is selected from the group consisting of: Nanog, Oct4, Sox2, Snail, Slug, Nestin, p75, TUJ1 (β-TubIII), MAP2, Synapsin and S100β.

According to one embodiment the cells are pluripotent.

According to one embodiment the cells are multipotent.

According to a specific embodiment the stem cells are autologous.

According to some embodiments, multipotent stem cells are obtained from the oral mucosa by isolation.

According to specific embodiments, isolation of stem cells from the oral mucosa comprises enzymatic digestion or explantation.

According to other embodiments, the stem cells are derived from whole population of stem cells obtained from the oral mucosa without enzymatic digestion or explantation.

The present invention also provides a cell population comprising differentiated stem cells derived from human oral mucosa. Mucosa-derived pluripotent or multipotent stem cells may be maintained and expanded in tissue culture in an undifferentiated state. According to various embodiments, these cells can be induced to differentiate into different neural cell types.

According to some embodiments, the cell population comprises at least 10% neural cells differentiated from oral mucosa stem cells. According to some embodiments, the cell population comprises at least 10% mature neural cells derived from oral mucosa stem cells. According to some embodiments, the cell population comprises at least 20%, 30%, 40%, 50% or 60% neural cells differentiated from oral mucosa stem cells. Each possibility represents a separate embodiment of the present invention.

According to a specific embodiment the cell population comprises cells which were not subjected to any sorting procedure.

According to some embodiments, the cell population is in the form of a culture, a suspension or an explant or in the form of a pharmaceutical composition further comprising an additive or excipient.

According to another aspect, the present invention provides a method of generating neural cells useful for treating neurological or psychiatric disease or disorder, the method comprising:
    (a) obtaining hOMSCs from human oral mucosa;
    (b) incubating the hOMSC of (a) in a pre-differentiating medium capable of inducing the differentiation of hOMSC toward a specific neural lineage; and
    (c) incubating the hOMSC of (b) in a differentiation medium, thereby generating cells useful for treating neurological or psychiatric disease or disorder.

According to some embodiments, the pre-differentiating medium comprises at least one agent selected from the group consisting of: N-2 supplement, basic Fibroblast Growth Factor 2 (bFGF) and epidermal growth factor (EGF).

According to particular embodiments, the hOMSC are incubated in a pre-differentiating medium for a duration of 24-96 hours.

According to some particular embodiments, the hOMSC are incubated in a pre-differentiating medium for a duration of about 48-72 hours.

According to some embodiments the differentiating medium comprises at least one agent selected from the group consisting of: Dibutyryl cyclic adenosine monophosphate (dbcAMP), IBMX (3-Isobutyl-1-methylxanthine), neuregulin and platelet-derived growth factor (PDGF).

According to some embodiments the differentiating medium comprises dbcAMP, IBMX, neuregulin, and PDGF, and the hOMSC are differentiated into glial neural cells.

According to specific embodiments, the incubation in differentiating medium is for a duration of about 24-120 hours.

According to some specific embodiments, the hOMSC are differentiated into glial neural cells by incubation for a duration of about 24-120 hours.

According to some embodiments, hOMSC derived glial cells comprise at least one cell type selected from the group consisting of: astrocytes, oligodendrocytes and Schwann cells.

According to some embodiments, the hOMSC are incubated in a differentiating medium comprising 0.1-10 mM dbcAMP, 0.0.1-10 mM IBMX, 5-500 ng/ml neuregulin, and 0.1-10 ng/ml PDGF for about 24-120 hours and are thereby differentiated into glial neural cells.

According to some specific embodiments the incubation in the differentiation medium is for about 48-96 hours.

According to some specific embodiments, the hOMSC are incubated in a differentiating medium comprising about 0.5-2 mM dbcAMP, about 0.2-1 mM IBMX, about 20-100 ng/ml neuregulin, and about 0.5-2 ng/ml PDGF for about 48-96 hours and are thereby differentiated into glial neural cells.

According to some specific embodiments, the hOMSC are incubated in a differentiating medium comprising about 1 mM dbcAMP, about 0.5 mM IBMX, about 50 ng/ml neuregulin, and about 1 ng/ml PDGF for about 48-96 hours and are thereby differentiated into glial neural cells.

According to some specific embodiments the incubation in the differentiation medium is for about 72 hours.

According to some alternative embodiments, the hOMSC are incubated in a differentiating medium comprising a plurality of agents selected from the group consisting of: B27, IBMX (3-Isobutyl-1-methylxanthine), dbcAMP, ascorbic acid, BNDF, Sonic Hedgehog (SHH), Wnt-1, fibroblast growth factor-8 (FGF-8), and bFGF, for a duration of at least 2 days and are thereby differentiated into dopaminergic neural cells.

According to some specific embodiments, the incubation is for at least 4 days.

According to some embodiments, the hOMSC are incubated in the differentiating medium for at least 11 days.

According to other embodiments, the hOMSC are incubated in the differentiating medium for 13 days.

According to yet other alternative embodiments, the hOMSC are differentiated into dopaminergic neural cells by incubation in a differentiating medium comprising 0.1-5% B27, 0.1-5 mM IBMX, 0.1-10 mM dbcAMP, 10-500 µM ascorbic, 10-500 ng/ml BNDF, for 2-4 days.

According to some particular embodiments, the hOMSC are differentiated into dopaminergic neural cells by incubation in a differentiating medium comprising 0.5% B27, 0.5 mM IBMX, 1 mM dbcAMP, 200 µM ascorbic, 50 ng/ml BNDF, for 4 days.

According to alternative embodiments, the hOMSC are differentiated into dopaminergic neural cells by incubation in a differentiating medium comprising 0.1-5% B27, 85-750 ng/mL Sonic Hedgehog, 30-300 ng/mL Wnt-1, 30-300 ng/mL FGF-8, 15-150 ng/mL BDNF, 15-150 ng/mL bFGF, and 65-600 ng/mL of ascorbic acid for at least 11 days.

According to some particular embodiments, the hOMSC are differentiated into dopaminergic neural cells by incubation in a differentiating medium comprising 0.5% B27, 100-400 ng/mL Sonic Hedgehog, 50-150 ng/mL Wnt-1, 50-150 ng/mL FGF-8, 25-100 ng/mL BDNF, 25-100 ng/mL bFGF, and 100-400 ng/mL of ascorbic acid for 13 days.

According to yet another aspect the present invention provides a method of treating a neurological or psychiatric disease or disorder or loss of neural tissue due to trauma, comprising administering to an individual in need thereof a therapeutically effective amount of a cell population comprising at least one neural cell differentiated from oral mucosa stem cells, thereby treating the neurological or psychiatric disease or disorder or loss of neural tissue due to trauma. According to some embodiments, the neural cell is a cell capable of secreting at least one neurotrophic factor (NTF). According to particular embodiments, the at least one NTF is selected from the group consisting of: glial-derived neurotrophic factor (GDNF), brain-derived neurotrophic factor (BDNF), neurotrophin-3 (NT-3), neurotrophin-4/5; Neurturin (NTN), Neurotrophin-4, Persephin, artemin (ART), ciliary neurotrophic factor (CNTF), insulin growth factor-I (IGF-I), Vascular endothelial growth factor (VEGF) and Neublastin.

According to some embodiments, the neural cell is a glial cell.

According to some embodiments, the glial cell is an astrocyte.

According to other embodiments, the glial cell is an oligodendrocyte or a Schwann cell.

According to some embodiments, the neural cell is a neuronal cell

According to other embodiments, the neural cell is a dopaminergic (DA) cell.

According to yet other embodiments, the cell population comprises glial and DA cells.

According to some embodiments, the neurological disease or disorder is a peripheral disease or disorder. According to particular embodiments, the peripheral disease or disorder is peripheral neuropathy. According to another particular embodiment, the peripheral disease or disorder is diabetic neuropathy.

According to other embodiments, the neurological disease or disorder is a central nervous system (CNS) disease or disorder.

According to some embodiments of the invention, the CNS disease or disorder is a neurodegenerative disease or disorder.

According to some embodiments a method of treatment of loss of neural tissue due to trauma is provided.

According to some embodiments of the invention, the CNS disease or disorder is selected from the group consisting of a motion disorder, a dissociative disorder, a mood disorder, an affective disorder, an addictive disorder and a convulsive disorder.

According to some embodiments of the invention, the neurological disease or disorder is a chronic neurological disease or disorder. According to particular embodiments, the chronic neurological disease or disorder is selected from the group consisting of Parkinson's, multiple sclerosis, epilepsy, amyotrophic lateral sclerosis, glaucomatous neuropathy, Alzheimer's disease and Huntington's disease.

According to a specific embodiment, the neurological disease is Parkinson's disease.

According to yet other embodiments, the neurological disease or disorder is an acute neurological disease or disorder. According to some particular embodiments, the acute neurological disease or disorder is stroke or autoimmune encephalomyelitis.

According to other embodiments, the CNS disease or disorder is a psychiatric disease or disorder. According to some particular embodiments, the psychiatric disease or disorder is schizophrenia, anxiety, depression or autism.

According to another aspect a method is provided of treating neurological or psychiatric disease or disorder associated with neural cell deficiency or dysfunction, or loss of neural tissue due to trauma, comprising administering to a patient in need thereof adult human mucosa-derived stem cells according to the invention, and providing conditions for differentiation of said cells into neural cells, thereby treating the neural cell deficiency or dysfunction.

According to some embodiments, the neurological disease or disorder is a neurodegenerative or psychiatric disease or disorder.

According to some embodiments, the neurological disease or disorder is a CNS disease or disorder. According to other embodiments, the neurological disease or disorder is a peripheral disease or disorder.

According to yet another aspect the present invention provides a method of induction or preservation of neurogenesis comprising administering to an individual in need thereof a therapeutically effective amount of a cell population of neural cells differentiated from oral mucosa stem cells, thereby inducing or preserving neurogenesis.

According to yet another aspect, the present invention provides a method of differentiating human oral mucosa stem cells from the lamina propria (hOMSC) into a specific type of mature neural cells.

According to some embodiments the invention provides a method of differentiating OMSC into dopaminergic neural cells comprising the steps of:
(a) incubating hOMSC for at least 48 hours in a pre-differentiation medium; and
(b) incubating the hOMSC of (a) in a differentiation medium for at least 11 days.

According to some embodiments, the pre-differentiation incubation is performed for duration of about 48-96 hours, in a medium comprising at least one agent selected from the group consisting of: N-2 supplement, bFGF and EGF.

According to some embodiments, the differentiating incubation is performed for at least 11 days in a medium comprising plurality of agents selected from the group consisting of: B27, IBMX, dbcAMP, ascorbic acid, BNDF, Sonic Hedgehog, Wnt-1, FGF-8, and bFGF.

According to some particular embodiments, the differentiating incubation medium comprises 0.1-5% B27, 85-750 ng/mL Sonic Hedgehog, 30-300 ng/mL Wnt-1, 30-300 ng/mL FGF-8, 15-150 ng/mL BDNF, 15-150 ng/mL bFGF, and 65-600 ng/mL of ascorbic acid.

According to some particular embodiments, the differentiating incubation medium comprises 0.1-5% B27, 100-400 ng/mL Sonic Hedgehog, 50-150 ng/mL Wnt-1, 50-150 ng/mL FGF-8, 25-100 ng/mL BDNF, 25-100 ng/mL bFGF, and 100-400 ng/mL of ascorbic acid.

Neural stem cells differentiated from hOMSC according to the methods and protocols of the present invention are also within the scope of the present invention as well as cell populations comprising these differentiated stem cells and pharmaceutical compositions comprising them.

According to some embodiments the neural stem cells acquire a DA phenotype and a neuron-like morphology, over-expressing inherent transcription factors and tyrosine hydroxylase and increasing regulated dopamine secretion to the medium.

According to other embodiments, the hOMSC-derived neural cells are neuron supporting glial cells which acquired the ability to secrete neurotrophic factors, express astrocytic markers and increase glutamate transporters in differentiated hOMSC. According to particular embodiments, the glial cells are astrocytes.

Essentially all of the uses known or envisioned in the prior art for neural stem cells can be accomplished with the isolated and differentiated mucosa-derived cells of the present invention. These uses include diagnostic, prophylactic and therapeutic techniques.

The present invention further discloses, a mixed cell population comprising both neuronal cells and supporting cells differentiated from stem cells wherein at least one of the cell lineage was differentiated from hOMSC.

According to some particular embodiments, both the neuronal cells and the supporting cells were differentiated from hOMSC.

According to some embodiments, the mixed cell population comprises dopaminergic cells and glial cells, wherein at least one of the cell lineage was differentiated from hOMSC.

According to some embodiments, cells secreting neurotrophic factors, for example glial cells, are capable of maintaining the phenotype of stem cells that were induced to differentiate into a neuronal phenotype, for example dopaminergic neurons.

According to some embodiments, cells secreting neurotrophic factors support neuronal cell maintenance after removal of neuronal differentiation medium.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 2. Comparative microscopic analysis showing that hOMSC acquired a neuronal-like morphology after differentiation. hOMSC developed a neuronal-like morphology with multiple projections emerging from cell bodies after two different DA differentiation protocols. Bright field microscopy of hOMSC cultured in serum free medium (2A-2B), treatment A (2C-2D) and treatment B (2E-2F). Scale bars 100 μM (left) and 200 μM (right).

DETAILED DESCRIPTION OF THE INVENTION

Figure 1A:
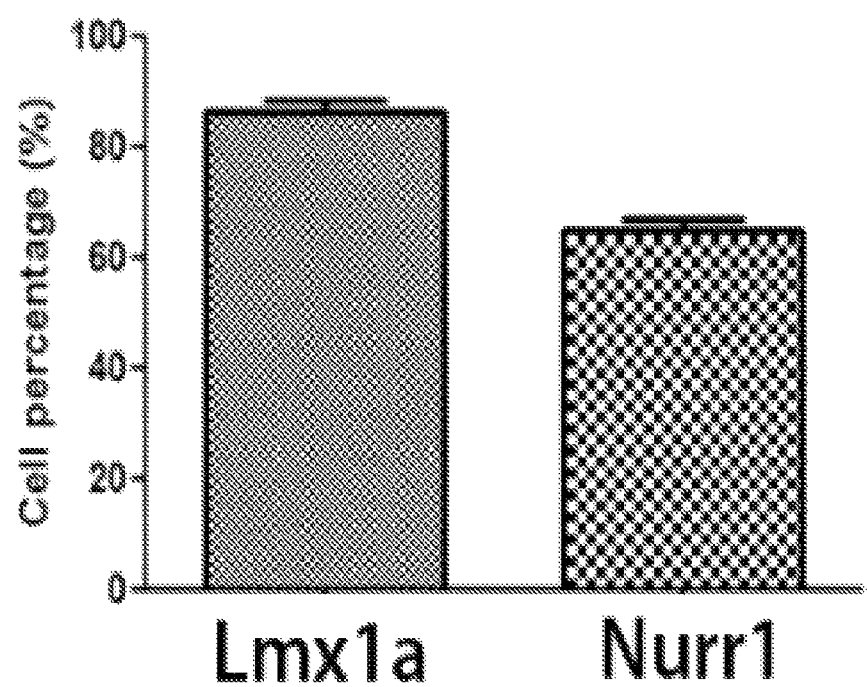
FIG. 1. Undifferentiated hOMSC constitutively express neuronal and dopaminergic markers. Flow cytometry analysis revealed that 86% and 68% of hOMSC express Lmx1a and Nurr1 respectively (1A and 1B).

The present invention provides neural cells differentiated from adult stem cells from human oral mucosa to restore neurological defects, improve neurological function, and treat various neurological and psychiatric disorders. The oral mucosa possesses a high regenerative capacity regardless of the individual's age. Recently, a unique stem cell population was isolated from the neural crest-derived lamina propria of the adult human oral mucosa, named hOMSC (Marynka-Kalmani et al. 2010, ibid). hOMSC express constitutively markers of embryonic (Oct4, Sox2, Nanog), mesenchymal (CD73, CD90, CD105) and neural crest (nestin, snail and p75) stem cells and differentiate into cell lineages of the three germ layers. hOMSC are a recently described neural crest (NC)-derived stem cell type, which coexpress the pluripotency markers Oct4, Nanog and Sox213 as well as the NC-SC markers, Snail, Slug, Sox10, Twist and Notch 1 in developing colonies and in vivo (Marynka-Kalmani K, et al. Stem Cells. 2010; 28:984-995; Widera D, et al. Stem Cells. 2009; 27:1899-1910; Davies L C, et al. Atem Cells Dev. 2010; 19:819-830). The NC is a transient neuroectodermal structure of the vertebrate embryo. During its embryonic existence it gives rise to migratory multipotent stem cells that populate various primordial tissues where they differentiate into neural lineages and or lineages with a mesenchymal phenotype termed ectomesenchyme or mesectoderm. Some of these NC-SC remain in a relative undifferentiated state in the adult, with a predisposition for neural differentiation even in tissues of mesenchymal origin such as dermis and bone marrow. However, this predisposition as determined by neural formation and differentiation is low (less than 1% of the cells) for supposed NC-SC obtained from skin compared to those obtained from dorsal root ganglia and even substantially lower in bone marrow derived cells (Nagoshi N, et al. Cell Stem Cell. 2008; 2:392-403). In contrast, the data of the present application indicate that neural and dopaminergic differentiation of hOMSC cultures takes place in the vast majority of the cells without the necessity of passaging the through the stage of neural sphere formation. This phenomenon point to the substantial advantage of the NC-SC derived from the lamina propria of adult oral mucosa over other sources.

The findings of this study and that of Marynka-Kalmani (ibid) also suggest that the niche of the oral mucosa lamina propria is more effective at preserving the stemness of embryonic NC-SC compared to the niche of other extrafacial tissues and extraoral facial tissues (Hauser S, et al. Stem Cells Dev. 2012; 21:742-756). The NC yields also to most of the peripheral nervous system (PNS) (neurons of the sensory, sympathetic, parasympathetic and enteric ganglia as well as ganglionic satellite glial cells and Schwann cells lining peripheral nerves) as well as the olfactory ensheathing cells of the olfactory nerve (Dupin E, Sommer L. Dev Biol. 2012; 366:83-95). The NC is also the origin of pigment and adrenal cells such as melanocytes and chromaffin cells respectively. Taking advantage of this biological phenomenon and through a non-invasive procedure, access to a NC-derived stem cells reservoir can be gained. hOMSC and DA neurons are both derived from the neural ectoderm, and moreover, the NC can give rise in vivo to hOMSC, neurons, melanocytes and adrenal cells (Dupin E, et al. C R Biol.

2007; 330:521-529). Interestingly, adrenal cells exhibit catecholamine's synthesis and TH expression, similar to DA neurons (Chung K F et al. Stem Cells. 2009; 27:2602-2613). Instead of TH, melanocytes express tyrosinase, enzyme which also converts tyrosine into L-Dopa, but because melanocytes lack the other catecholamine synthetic enzymes, they do not synthesize catecholamines. Given the ability of NC-derived cells to differentiate into cells with synthetic machinery resembling those of dopamine synthetic pathway, this study evaluated for the first time, hOMSC propensity of differentiating into dopamine secreting cells and demonstrated their restorative potential in a PD animal model.

Given the multipotency of OMSC, their neural crest related origin, the easy access and the invariable phenotype regardless donor's age, these cells are shown to serve as a useful stem cell source for autologous cell therapy for neurological disorders.

It is herein demonstrated for the first time that hOMSC express constitutively a repertoire of neural genes as well as specific dopaminergic neurons markers, such as tyrosine hydroxylase, Lmx1A and Nurr1 and astrocyte markers such as S100β, and therefore are an excellent source for autologous cell therapy of neurodegenerative and psychiatric diseases and disorders. Exposure of hOMSC to a dopaminergic differentiation medium, induced a neuronal-like morphology in the vast majority of the cells, accompanied by a down-regulation of early stem cells markers and an upregulation of dopaminergic developmental transcription factors such as Nurr1, Pitx3, FoxA2, Otx2 and Lmx1A. Notably, following dopaminergic differentiation, a significant increase in the regulated dopamine secretion was observed. By the other hand, after astrocyte differentiation protocol, hOMSC acquired an astrocyte-like morphology as well as an increase in specific markers such as S100β, GFAP, Glt1 and an increase in the secretion of neurotrophic factors.

The results demonstrate the excellent propensity of hOMSC to differentiate into functional DA neurons and into astrocytes-like cells with enhanced neurotrophic factors secretion in vitro. Considering these results and the ready accessibility of the oral mucosa, hOMSC emerge as an advantageous new stem cells population for the autologous cell therapy treatment of Parkinson's disease and other neurodegenerative and psychiatric diseases.

As previously shown, hOMSC express general neuronal markers constitutively, such as TUJ1 and MAP2. It is herein shown that hOMSC express the dopaminergic markers NURR1, LMX1A and low levels of TH, phenomena which has been already described in other stem cells (Montzka et al. BMC Neurosci. 2009; 10:16; Blondheim N R, Stem Cells Dev. 2006; 15:141-164). Taking as a starting point that hOMSC express neuronal and DA markers, the cells were challenged with two different differentiation protocols—treatment A and treatment B, both of which were sufficient to induce morphological neuronal-like changes in hOMSC. Treatment A was found to induce the dopaminergic-like differentiation of bone marrow MSC. Treatment B was more efficient in reducing the pluripotent-associated stem cells markers and in augmenting the neuronal marker Tuj1, pointing to a neuronal differentiation process. Notably treatment B, based on the composition of midbrain developmental signaling, was more effective than treatment A in inducing dopaminergic differentiation. This was evidenced by the higher expression of classical dopaminergic markers Pitx3, Nurr1, Lmx1a, DAT and TH in hOMSC differentiated into dopaminergic neurons (hOMSC-DA) compared to naïve hOMSC or hOMSC subjected to treatment A. The higher efficiency of treatment B to induce dopaminergic differentiation of hOMSC, at the gene and protein levels, was also demonstrated at the functional level in vitro. Upon stimulation with KCl, hOMSC-DA secreted 4 folds more dopamine that hOMSC subjected to treatment A. These results also indicate that hOMSC-DA acquired an ion-dependent regulated dopamine release mechanism.

Since dopaminergic differentiation of SC is majority controlled by transcription factors, the expression and the localization of Lmx1a, Nurr1 and Pitx3 in hOMSC during their differentiation was assessed. Naïve hOMSC showed cytoplasmic localization of Lmx1a and Nurr1; however after the differentiation process with treatment B, an increase in these transcription factors expressions and their shift towards the nucleus was evidenced.

Immunostaining analysis indicated that TH expression was increased in in the vast majority of hOMSC subjected to treatment B differentiation protocol. In parallel, western blot analysis also demonstrated 4 folds increase in TH immunoreactivity pointing to the correlation between the differentiation process and TH expression. This phenomenon is extremely high if compared to the low differentiation efficiencies seen in ESC, iPS or neural stem cells differentiation by soluble factors only. These findings demonstrate that hOMSC are prone to differentiate into cells with a dopaminergic-like phenotype.

The functional and therapeutic potentials of hOMSC-DA were tested in the well-established evaluation model of hemi-parkinsonian rat (Schwarting R K, Huston J P. Prog Neurobiol. 1996; 50:275-331; Whishaw I Q, et al. Behav Brain Res. 1997; 89:167-177). The amphetamine-induced rotations test demonstrated the effectiveness of hOMSC-DA transplantation into the rat striatum in contrast to the administration of saline or naïve hOMSC. At all the evaluated time points, 1, 4 and 8 weeks post-transplantation, a significant reduction in the induced rotation of 54, 40 and 47%, respectively was observed in the hOMSC-DA treated animals, compared to the saline treated group.

A trend in reduction of the induced-rotations in the naïve hOMSC treated group was observed that reached statistical significance compared to the saline treated group only at 8 weeks after transplantation. Without wishing to be bound to any theory of mechanism of action is proposed that this improvement is due to local secretion of neurotrophic factors by naïve hOMSC that have been reported to constitutively secrete FGF-2, VEGF, EGF and NGF14. Administration of 6-OHDA in the MFB causes gradual death of dopaminergic neurons as evidenced by the continuous increase in the number of amphetamine induced rotations in untreated control groups reported in the present and previous studies (Kirik D, Exp Neurol. 1998; 152:259-277). As the dopaminergic circuit connect the substantia nigra with the striatum through axon projections, it is conceivable that neurotrophic factors secretion into the striatum in the proximity of axon terminals, could lead by retrograde transport to a survival signaling cascade in damaged, but still not dead, DA neurons of the substantia nigra. It is therefore disclosed that neurotrophic factors secreting hOMSC can be used, even without prior differentiation, to restore neurological functions and or treat neurological diseases and disorders.

Motor asymmetry evaluation performed two weeks after transplantation revealed a significant improvement in the hOMSC-DA treated group as demonstrated by a reduction of 38% in the cylinder test score in this group compared to the other two groups.

General motor coordination was assessed by the rotor-rod test, in which a 40% reduction after the 6-OHDA injury was evidenced in accordance to the literature (Iancu et al. Behav Brain Res. 2005; 162:1-10; Rozas G, Labandeira Garcia J L. Brain Res. 1997; 749:188-199). This impairment was significantly restored following hOMSC-DA transplantation. One week after cell grafting, a major improvement was seen in animals transplanted with hOMSC-DA, while no recovery was detected in the other two control groups. This differential effect was maintained throughout the experimental period. The colocalization of TH with hOMSC-DA in the striatal tissue of the injured hemisphere and the higher content of DA in these hemispheres, indicate that the improvement in the motoric parameters were mediated by dopamine secretion. The results of the present study demonstrate that hOMSC-DA were able to engraft in the striatum and maintain their phenotype throughout the experimental period (10 weeks). As an important remark, no tumor formation was evidenced in the evaluated tissues.

The study of Marynka-Kalmani (ibid) has proved that trillions of hOMSC are cost-effectively and reproducibly generated from a biopsy of 3-4×2×1 mm that is obtained with negligible morbidity. It is now shown that hOMSC have a robust propensity to differentiate into dopaminergic-like neurons without the necessity to passaging them through the neural sphere stage required for other stem cells (Kaltschmidt B, et al. Stem Cell Rev. 2012; 8:658-671; Wang J, et al. Stem Cells Dev. 2010; 19:1375-1383). Previous work indicates that aging affect negligibly the growth, clonogenicity and differentiation of hOMSC. Considering that the majority of the patients affected by PD are elderly, these finding and the data presented in this study together with the readily and repetitive accessibility of the oral mucosa suggest that hOMSC are a preferable population for autologous cell therapy in Parkinson's Disease.

The hOMSC potential to differentiate into neuron supporting cells (NS) was evaluated in order to mimic physiological astrocytes trophic and neuroprotective effect. hOMSC were differentiated into cells showing an astrocyte-like morphology and expressing prototypical astrocyte markers such as GFAP, S100β and the glutamate transporter EAAT2. Moreover, these cells expressed GDNF, IGF-1 and high levels of BDNF and VEGF. It was demonstrated herein that the conditioned medium of astrocyte-like hOMSC that secrete neurotrophic factors (hOMSC-NS) is sufficient to rescue motorneurons from hypoxia or oxidative-induced cell death in vitro. As an in vivo approach, rats with sciatic nerve injury were transplanted with hOMSC-derived NSs. Notably, treated rats not only showed improved motor function but increased tissue levels of NTFs and a significant preservation of functional neuromuscular junctions. The findings show for the first time that cells resembling astrocytes with enhanced NTFs production and neuroprotective effects in vitro and in vivo, can be successfully generated from oral mucosa stem cells.

In the present work the expression of GFAP, VEGF and BDNF in muscular tissue after transplantation in sciatic nerve injured rats was quantified. The facts that a substantially higher expression of NTFs was observed in hOMSC-NS treated rats and that this secretion was colocalized with cells of human origin, point to the capacity of hOMSC-NS to maintain their astrocyte-like phenotype in vivo within the limit of the experimental period. These data is supported also by the work of Marynka-Kalmani et al. (ibid) who showed that hOMSC are capable of developing into Schwann-like cells two months following their transplantation into SCID mice.

The astrocyte-like phenotype of hOMSC-NS proved to have functional activity both in vitro and in vivo as evidenced by their ability to rescue motor neurons subjected to chemical and respiratory stress, and by the ability to preserve NMJ innervation and enhance functional recovery of sciatic nerve injured rats.

Taken together, the data of the present study indicate that the oral mucosa is a superior source for generating therapeutic quantities of stem cells with a high propensity to differentiate along glial lineages and function similar to glial cells of the nervous system.

Dopaminergic Neurons Induction Mechanisms

The success of emerging CRT for PD will reside among other issues such as implantation site, environment modification or patient selection, on the accurate combination of chosen stem cells type and the methodology or differentiation protocol that will be applied on them. Within a decade neuroscientists have gathered a wealth of information about the midbrain dopaminergic system and have identified many molecular processes and mechanisms that underlie midbrain DA neuron development, maintenance and function. To date several protocols have been designed to induce the desired A9 DA neuron phenotype using different stem cells sources. These protocols intend to simulate the natural development process induced by intrinsic and extrinsic factors involved in DA neurogenesis. Within the extrinsic factors, the most widely used are soluble proteins such as sonic hedgehog (SHH), fibroblast growth factors 2 and 8 (FGF 2, 8) and members of the Wnt family. SHH is a morphogenetic factor secreted from the floor plate with crucial effect on the ventral midbrain during development and induce the proliferation of DA neuron precursors (Hynes, M. & Rosenthal, A. *Neuron* 2000, 28, 11-14; Wang, Y. et al., *J Neuroimmune Pharmacol* 2007, 2, 243-250. In the same way FGF-8, produced by the isthmus organizer, also plays an important role in DA neuron specification and promotes DA neurogenesis (Ye, W. et al., *Cell* 1998, 93, 755-766). Members of the Wnt family are additional factors produced and secreted in the midbrain development which promote activities such as precursor proliferation and neural differentiation. Wnt signaling through the action of Wnt1, 3a and 5a has been reported as needed for the establishment of the midbrain-hindbrain regions and are involved in activating engrailed (EN) genes, which are necessary for later stages of midbrain DA neuronal development. Moreover mutant Wnt mice showed a loss of most midbrain DA neurons and ectopic expression of Wnt1 and 5a in NSC lead to DA differentiation and NURR1 positive cells (Castelo-Branco, G. & Arenas, E. *Neurodegener Dis* 2006, 3, 5-11). Other growth factors such as BDNF, GDNF, EGF and TGF-β have been used and showed a DA neuron inducer activity. Chemical inducers are also considered as extrinsic factors that enhance DA neuron formation. Among these factors, RA (retinoic acid), dbcAMP (dibutyryl cyclic-AMP), IBMX (3-isobutyl-1-methylxanthine), AA (ascorbic acid) and BHA (butylated hydroxyanisole) are currently the most effective inducers used (Levy, Y. S., et al. *Cytotherapy* 2008, 10, 340-352). To certain stem cells sources, extrinsic induction can be sufficient to generate DA neurons, but in cases of stem cells that are not naturally prone to become midbrain DA neurons, this process seems to be more difficult, inefficient and incomplete. Induction by intrinsic factors has facilitated and improved DA neuron generation. Genetic manipulation, mainly by lentiviral transduction, has demonstrated that ectopic insertion of transcription factors (TF) represented by homeodomain proteins, pro-neural genes and genes involved in epigenetic control, effectively induce a DA neuron phenotype (Kim, H. J. *Biochim Biophys Acta* 2011, 1812, 1-11). The development of mice deficient in PITX3, LMX1A/B, EN1, EN2, neurogenin 2 (NGN2) and the orphan nuclear receptor 1 (NURR1) has facilitated the development of a map that specifies gene—function relationships during midbrain DA neurons differentiation (Burbach, J. P. & Smidt, M. P. *Trends Neurosci* 2006, 29, 601-603). The expression of the gene encoding for LIM homeobox transcription factor 1 (LMX1A), has been reported as both necessary and sufficient for the induction of midbrain DA phenotype in midbrain neuroepithelial cells, ESC and MSC, effect that can be enhanced by extrinsic factors. Moreover, the neurotransmitter phenotype is partly determined by the transcription factor NURR1, which regulates several proteins that are required for dopamine synthesis and regulation, such as TH, vesicular monoamine transporter 2 (VMAT2), dopamine transporter (DAT) and RET receptor tyrosine kinase (cRET). Overexpression of PITX3 and FOXA2, other transcriptions factor involved in DA specification, was seen to actively assist NURR1 and LMX1A to induce human ESCs and NSCs terminal maturation to midbrain DA neurons. Currently, most protocols rely on early induction through SHH, FGF-8, WNT1/5A, TGFB and RA, which are often combined with the introduction of transcription factors like LMX1A and NURR1. The generated cells should be monitored for the expression of NURR1, EN1, EN2 and the midbrain DA neuron-specific gene PITX3, which display the full dopaminergic phenotype. In order to achieve rapid and safe clinical translation, transgenesis must be preferably avoided until safer gene delivery methods can be developed.

Astrocytes-Like Cells for Cell Therapy in Neurodegenerative Diseases

Astrocytes, a subtype of glial cell, playing a crucial role in the control of the homeostatic extracellular environment in the adult brain, are the main producers of neutrophic factors, among others, nerve growth factor (NGF) and brain-derived neurotrophic factor (BDNF), as well as glial-derived neurotrophic factor (GDNF) (Muller, H. W., Junghans, U. & Kappler, J. 1995, *Pharmacol Ther* 65, 1-18). As part of their activity, astrocytes clear the brain of excess glutamate and dopamine, both of which might be toxic for dopaminergic neurons (Teismann, P., et al. *Mov Disord* 2003, 18, 121-129). Previous work showed that through a defined two-step protocol for astrocyte differentiation, MSC exhibited the typical satellite-like astrocyte morphology accompanied by positive immunoreactivity to three major astrocyte markers: S10013, GFAP, GS and with an enhanced secretion of neurotrophic factors (Bahat-Stroomza, M., et al. *J Mol Neurosci* 2009, 39, 199-210). Moreover they showed that only the differentiated cells medium could protect neuroblastoma cell line (SH-SY5Y) against oxidative stress induced by 6-OHDA, whereas the media derived from non-differentiated (MSC) cultures had no effect on cell survival. This protection may be explained by the higher levels of NTFs shown to be secreted from the differentiated cells. MSC derived astrocytes-like cells were transplanted into the striatum of 6-hydroxydopamine-lesioned rats, a model of PD, and produced a progressive reduction in the apomorphine-induced contralateral rotations as well as behavioral improvement in rotor-rod and the "sunflower seeds" eating motor tests. Histological assessments revealed that the engrafted cells survived until the end of the experiment (120 days) and expressed the astrocyte marker GFAP, indicating the preservation of their astrocyte-like characteristics. Moreover the reduction in the apomorphine-induced rotations could have been due to sprouting of the nerve terminals of the remaining dopaminergic neurons in response to the neurotrophins produced and locally released by the engrafted astrocyte-like cells. This assumption is supported by the marked increase in the density of the TH immunoreactive fibers in the lesioned/engrafted striata compared to the saline-treated control group. Taken together, these data indicate that transplanted astrocyte-like cells, probably through their continuous neurotrophin factor secretion, are capable of renovating and restoring the lost network of striatal dopaminergic nerve terminals in PD. Also striatal transplantation of MSC with VEGF or BDNF overexpression ameliorated significantly the apomorphine-evoked rotations and reduced the loss of dopaminergic neurons in the lesioned substantia nigra.

Stem cells contained in the lamina propria may be differentiated, using specific protocols, into dopaminergic or astrocyte neural cells and used for prevention and treatment of neurodegenerative diseases and disorders. In addition, whole populations of oral mucosa can be used without requiring laborious purification, as a source for pluripotent stem cells capable of differentiating into neural cell lineages under in vivo and/or in vitro conditions.

Typical whole populations contain low proportion of stem cells and therefore expansion and isolation of stem cells are laborious, long and usually not efficient. It was demonstrated that primary whole population and expanded whole cell population derived from the lamina propria of the oral mucosa consists mainly (more then 80%) of stem cells. High proportions (80-90%) of cell populations obtained from the oral mucosa of three different donors are shown herein to express mesenchymal stem cells markers. A typical isolation method of stem cells from a solid tissue for clinical utilization comprises releasing the cells from the extracellular matrix by enzymatic digestion or by explantation; expanding primary whole population in order to obtain sufficiently large populations; and isolation of stem cells from the whole populations.

The quality and quantity of the isolated stem cells population form the lamina propria oral mucosa is largely unaffected by aging, and can be expanded in vitro without loosing its pluripotency and can be safely retransplanted into the affected donor to effectively achieve neural regeneration.

Without wishing to be bound to any mechanism of action, it is proposed that neuronal differentiation is supported by soluble factors that are transiently expressed during time windows. Once neuronal differentiation is achieved, this state is maintained by glial cells probably through the secretion of neurotrophic factors. The present invention therefor discloses also a mixed cells population comprising both functional cells and supporting cells secreting factors such as growth factors, wherein at least one of the cells' types was differentiated from hOMSC. The mixed cells population comprises, according to some embodiments, both neuronal cells and supporting cells secreting neurotrophic factors wherein at least one of the cell type is differentiated from hOMSC. Cells secreting neurotrophic factors, for example glial cells, are capable of maintaining the phenotype of stem cells that were induced to differentiate into a neuronal phenotype, for example dopaminergic neurons.

Definitions

"Stem cells" (SC) are undifferentiated cells, which can give rise to a succession of mature functional cells.

"Embryonic stem (ES) cells" are cells derived from the inner cell mass of the embryonic blastocysts that are pluripotent, thus possessing the capability of developing into any organ or tissue type or, at least potentially, into a complete embryo.

"Adult stem cells" are post-natal stem cells derived from tissues, organs or blood of an organism after its birth.

"Pluripotent stem cells" are stem cells capable of generating the three embryonic cell layers and their derivatives cell lineages and tissues;

"Multipotent stem cells" are stem cells capable of forming multiple cell lineages that constitutes an entire tissue or organ;

The term "oral mucosa" refers to the mucosal lining the oral cavity, namely: the cheeks and the alveolar ridge including the gingiva and the palate, the tongue, the floor of the mouth and the oral part of the lips.

A "neurotrophic factor" refers to a cell factor that acts on the nervous system comprising growth, differentiation, functional maintenance and/or survival effects on neurons. Examples of neurotrophic factors include, but are not limited to, glial derived neurotrophic factor (GDNF), GenBank accession nos. L19063, L15306; brain-derived neurotrophic factor (BDNF), GenBank accession no CAA62632; neurotrophin-3 (NT-3), GenBank Accession No. M37763; neurotrophin-4/5; Neurturin (NTN), GenBank Accession No. NP_004549; Neurotrophin-4, GenBank Accession No. M86528; Persephin, GenBank accession no. AAC39640; brain derived neurotrophic factor, (BDNF), GenBank accession no. CAA42761; artemin (ART), GenBank accession no. AAD13110; ciliary neurotrophic factor (CNTF), GenBank accession no. NP_000605; insulin growth factor-I (IGF-I), GenBank accession no. NP_000609; and Neublastin GenBank accession no. AAD21075.

Separation Methods

Separation of the stem cells according to the present invention may be performed according to various physical properties, such as fluorescent properties or other optical properties, magnetic properties, density, electrical properties, etc. Cell types can be isolated by a variety of means including fluorescence activated cell sorting (FACS), protein-conjugated magnetic bead separation, morphologic criteria, specific gene expression patterns (using RT-PCR), or specific antibody staining.

The use of separation techniques include, but are not limited to, those based on differences in physical (density gradient centrifugation and counter-flow centrifugal elutriation), cell surface (lectin and antibody affinity), and vital staining properties (mitochondria-binding dye rho123 and DNA-binding dye Hoechst 33342).

Cells may be selected based on light-scatter properties as well as their expression of various cell surface antigens. The purified stem cells have low side scatter and low to medium forward scatter profiles by FACS analysis. Cytospin preparations show the enriched stem cells to have a size between mature lymphoid cells and mature granulocytes.

Various techniques can be employed to separate the cells by initially removing cells of dedicated lineage. Monoclonal antibodies are particularly useful. The antibodies can be attached to a solid support to allow for crude separation. The separation techniques employed should maximize the retention of viability of the fraction to be collected.

The separation techniques employed should maximize the retention of viability of the fraction to be collected. Various techniques of different efficacy may be employed to obtain "relatively crude" separations. Such separations are where up to 30%, usually not more than about 5%, preferably not more than about 1%, of the total cells present are undesired cells that remain with the cell population to be retained. The particular technique employed will depend upon efficiency of separation, associated cytotoxicity, ease and speed of performance, and necessity for sophisticated equipment and/or technical skill.

Procedures for separation may include magnetic separation, using antibody-coated magnetic beads, affinity chromatography, cytotoxic agents joined to a monoclonal antibody or used in conjunction with a monoclonal antibody, e.g., complement and cytotoxins, and "panning" with antibody attached to a solid matrix, e.g., plate, or other convenient technique.

Techniques providing accurate separation include fluorescence activated cell sorters, which can have varying degrees of sophistication, e.g., a plurality of color channels, low angle and obtuse light scattering detecting channels, impedance channels, etc.

Other techniques for positive selection may be employed, which permit accurate separation, such as affinity columns, and the like.

Antibodies used for separation may be conjugated with markers, such as magnetic beads, which allow for direct separation, biotin, which can be removed with avidin or streptavidin bound to a support, fluorochromes, which can be used with a fluorescence activated cell sorter, or the like, to allow for ease of separation of the particular cell type. Any technique may be employed which is not unduly detrimental to the viability of the remaining cells.

While it is believed that the particular order of separation is not critical to this invention, the order indicated is preferred. Preferably, cells are initially separated by a coarse separation, followed by a fine separation, with positive selection of one or more markers associated with the stem cells and negative selection for markers associated with lineage committed cells.

Use of Stem Cells for Therapeutic Purposes

A significant challenge to the use of stem cells for therapy is to control growth and differentiation into the particular type of tissue required for treatment of each patient. Methods for achieving or promoting this type of use have been disclosed in the art. The following are merely examples of suitable methods for utilizing stem cells in cell therapy.

Differentiated cells of the present invention can be used for tissue reconstitution, protection or regeneration in a human patient in need thereof. The cells are administered in a manner that permits them to graft to the intended tissue site and reconstitute or regenerate the functionally deficient area.

Cell Therapy Applications for Neuronal Disorders

Differentiated cells of present invention can also be used for transplant therapy. For example, neural stem cells can be transplanted directly into parenchymal or intrathecal sites of the central nervous system, according to the disease being treated (U.S. Pat. No. 5,968,829 for example). The efficacy of neural cell transplants can be assessed in a rat model for acutely injured spinal cord as described by McDonald et al. (Nat. Med. 5, 1410, 1999).

Certain neural differentiated cells of the present invention may be designed for treatment of acute or chronic damage to the nervous system. For example, excitotoxicity has been implicated in a variety of conditions including epilepsy, stroke, ischemia, Huntington's disease, Parkinson's disease and Alzheimer's disease. Certain differentiated cells of this invention may also be appropriate for treating demyelinating or dysmyelinating disorders, such as Pelizaeus-Merzbacher disease, multiple sclerosis, leukodystrophies, neuritis and neuropathies. Appropriate for these purposes are cell cultures enriched in oligodendrocytes or oligodendrocyte precursors to promote remyelination. The differentiated cells of the present invention can be generated in large quantities, and therefore may serve as an excellent source for cell replacement therapy in neurological disorders.

Gene Therapy

Gene therapy refers to the transfer and stable insertion of new genetic information into cells for the therapeutic treatment of diseases or disorders. The foreign gene is transferred into a cell that proliferates to spread the new gene throughout the cell population. Thus stem cells, or pluripotent progenitor cells, are usually the target of gene transfer, since they are proliferative cells that produce various progeny lineages which will potentially express the foreign gene.

Pluripotent or multipotent stem cells according to the present invention may be used in gene therapy for the treatment of a variety of diseases, particularly genetic diseases.

Optionally, the progenitor cells obtained using the method of the present invention can be manipulated to express desired gene products. Gene therapy can be used to either modify a cell to replace a gene product, to facilitate regeneration of tissue, to treat disease, or to improve survival of the cells following implantation into a patient (i.e. prevent rejection). In this embodiment, the progenitor cells are transfected prior to expansion and differentiation. Techniques for transfecting cells are known in the art.

A skilled artisan could envision a multitude of genes which would convey beneficial properties to the transfected cell or, more indirectly, to the recipient patient/animal. The added gene may ultimately remain in the recipient cell and all its progeny, or may only remain transiently, depending on the embodiment. For example, genes encoding angiogenic factors could be transfected into progenitor cells isolated from smooth muscle. Such genes would be useful for inducing collateral blood vessel formation as the smooth muscle tissue is regenerated. It some situations, it may be desirable to transfect the cell with more than one gene.

Cryopreservation

The freezing of cells is ordinarily destructive. On cooling, water within the cell freezes. Injury then occurs by osmotic effects on the cell membrane, cell dehydration, solute concentration, and ice crystal formation. As ice forms outside the cell, available water is removed from solution and withdrawn from the cell, causing osmotic dehydration and raised solute concentration which eventually destroys the cell. These injurious effects can be circumvented by (a) use of a cryoprotective agent, (b) control of the freezing rate, and (c) storage at a temperature sufficiently low to minimize degradative reactions.

Cryoprotective agents which can be used include but are not limited to dimethyl sulfoxide (DMSO), glycerol, polyvinylpyrrolidine, polyethylene glycol, albumin, dextran, sucrose, ethylene glycol, i-erythritol, D-ribitol, D-mannitol, D-sorbitol, i-inositol, D-lactose, choline chloride, amino acids, methanol, acetamide, glycerol monoacetate, and inorganic salts.

In a preferred embodiment, DMSO is used, a liquid which is nontoxic to cells in low concentrations. DMSO freely permeates the cell and serves as a cryoprotectant. Cryoprotectants protect intracellular organelles by combining with water to modify its freezability and prevent damage from ice formation. Addition of plasma (e.g., to a concentration of 20-25%) can augment the protective effect of DMSO. After addition of DMSO, cells should be kept at 0° C. until freezing, since DMSO concentrations of about 1% are toxic at temperatures above 4° C.

A controlled slow cooling rate is critical. Different cryoprotective agents and different cell types have different optimal cooling rates (Lewis, J. P., et al. Transfusion 7, 17-32, 1967). The heat of fusion phase where water turns to ice should be minimal. The cooling procedure can be carried out by use of, e.g., a programmable freezing device or a methanol bath procedure. Programmable freezing apparatuses allow determination of optimal cooling rates and facilitate standard reproducible cooling. Programmable controlled-rate freezers such as Cryomed or Planar permit tuning of the freezing regimen to the desired cooling rate curve. For example, for marrow cells in 10% DMSO and 20% plasma, the optimal rate is 1 to 3° C./minute from 0° C. to −80° C. In a preferred embodiment, this cooling rate can be used for the cells of the invention. The container holding the cells must be stable at cryogenic temperatures and allow for rapid heat transfer for effective control of both freezing and thawing. Sealed plastic vials (e.g., Nunc, Wheaton cryules) or glass ampoules can be used for multiple small amounts (1-2 ml), while larger volumes (100-200 ml) can be frozen in polyolefin bags (e.g., Delmed) held between metal plates for better heat transfer during cooling. (Bags of bone marrow cells have been successfully frozen by placing them in −80° C. freezers which, fortuitously, gives a cooling rate of approximately 3° C./minute).

In an alternative embodiment, the methanol bath method of cooling can be used. The methanol bath method is well-suited to routine cryopreservation of multiple small items on a large scale. The method does not require manual control of the freezing rate nor a recorder to monitor the rate. In a preferred aspect, DMSO-treated cells are pre-cooled on ice and transferred to a tray containing chilled methanol which is placed, in turn, in a mechanical refrigerator (e.g., Harris or Revco) at −80° C. Thermocouple measurements of the methanol bath and the samples indicate the desired cooling rate of 1 to 3° C./minute. After at least two hours, the specimens have-reached a temperature of −8° C. and can be placed directly into liquid nitrogen (−196° C.) for permanent storage.

After thorough freezing, cells can be rapidly transferred to a long-term cryogenic storage vessel. In a preferred embodiment, samples can be cryogenically stored in liquid nitrogen (−196° C.) or its vapor (−165° C.). Such storage is greatly facilitated by the availability of highly efficient liquid nitrogen refrigerators, which resemble large Thermos containers with an extremely low vacuum and internal super insulation, such that heat leakage and nitrogen losses are kept to an absolute minimum.

Methods of cryopreservation of viable cells, or modifications thereof, are available and envisioned for use (e.g., cold metal-mirror techniques; U.S. Pat. Nos. 4,199,022; 3,753,357; 4,559,298). U.S. Pat. No. 6,310,195 discloses a method for preservation of pluripotent progenitor cells, as well as totipotent progenitor cells based on a use of a specific protein. In a preferred case, the protein can preserve hematopoietic progenitor cells, but progenitor cells from other tissues can also be preserved, including nerve, muscle, skin, gut, bone, kidney, liver, pancreas, or thymus progenitor cells.

Frozen cells are preferably thawed quickly (e.g., in a water bath maintained at 37-41° C.) and chilled immediately upon thawing. In particular, the vial containing the frozen cells can be immersed up to its neck in a warm water bath; gentle rotation will ensure mixing of the cell suspension as it thaws and increase heat transfer from the warm water to the internal ice mass. As soon as the ice has completely melted, the vial can be immediately placed in ice.

In Vitro Culture and Expansion of Stem Cells

An optional procedure (either before or after cryopreservation) is to expand the stem in vitro. However, care should be taken to ensure that growth in vitro does not result in the production of differentiated progeny cells at the expense of multipotent stem cells which are therapeutically necessary for reconstitution.

Various factors can also be tested for use in stimulation of proliferation in vitro, including but not limited to interleukin-3 (IL-3), granulocyte-macrophage (GM)-colony stimulating factor (CSF), IL-1 (hemopoietin-1), IL-4 (B cell growth factor), IL-6, alone or in combination.

The present invention further encompasses methods for obtaining compositions of cells which are highly enriched in stem cells. The method comprises incubating the compositions described above under conditions suitable for generation of stem cells. Compositions comprising the original stem cells and/or the generated stem cells are obtained thereby.

Clonogenicity

Figure 4:
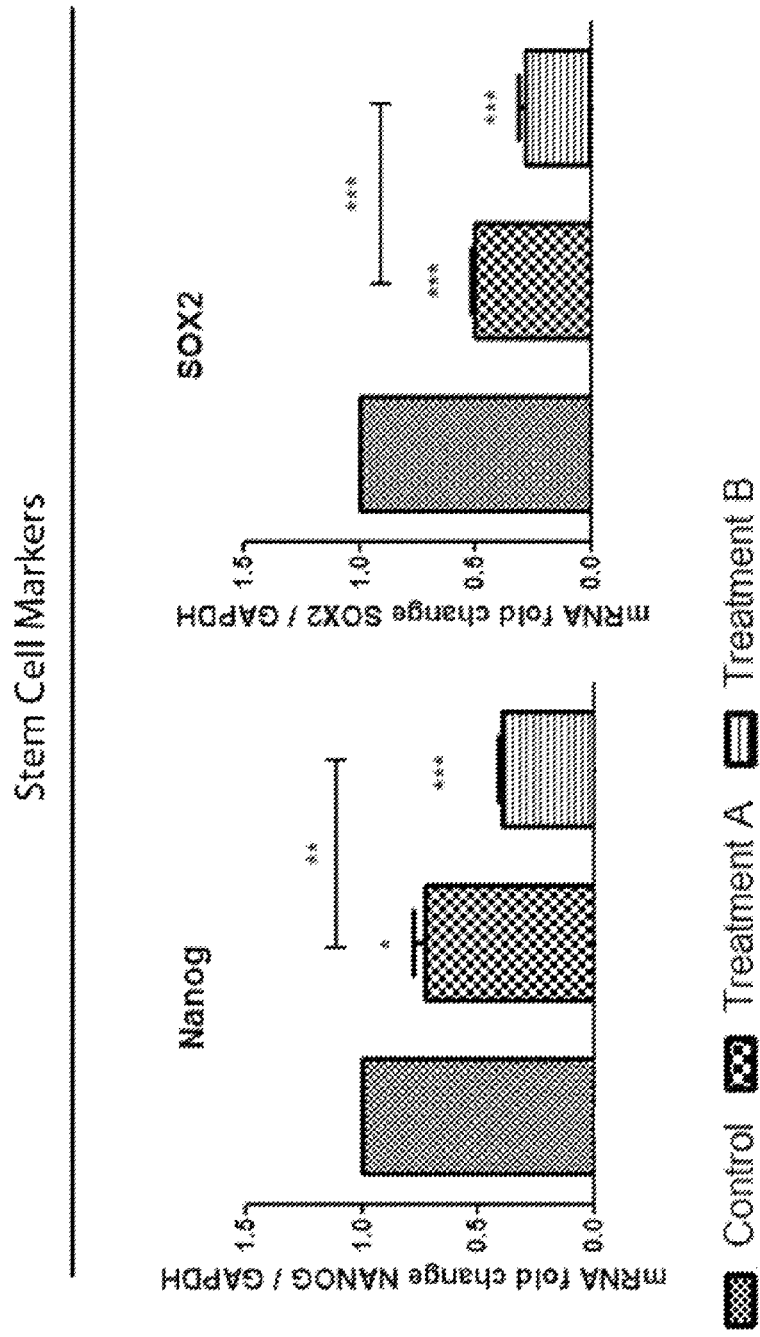
FIG. 4. Induction of differentiation in hOMSC increased the expression of DA markers. Real Time PCR analysis of differentiated hOMSC with either treatment A or B. The analysis show increased neuronal and dopaminergic markers, as well as reduced hOMSC stem cell markers. Data is expressed as Mean±SEM, significance levels *p<0.05, p<0.01, *p<0.001.
Figure 4:
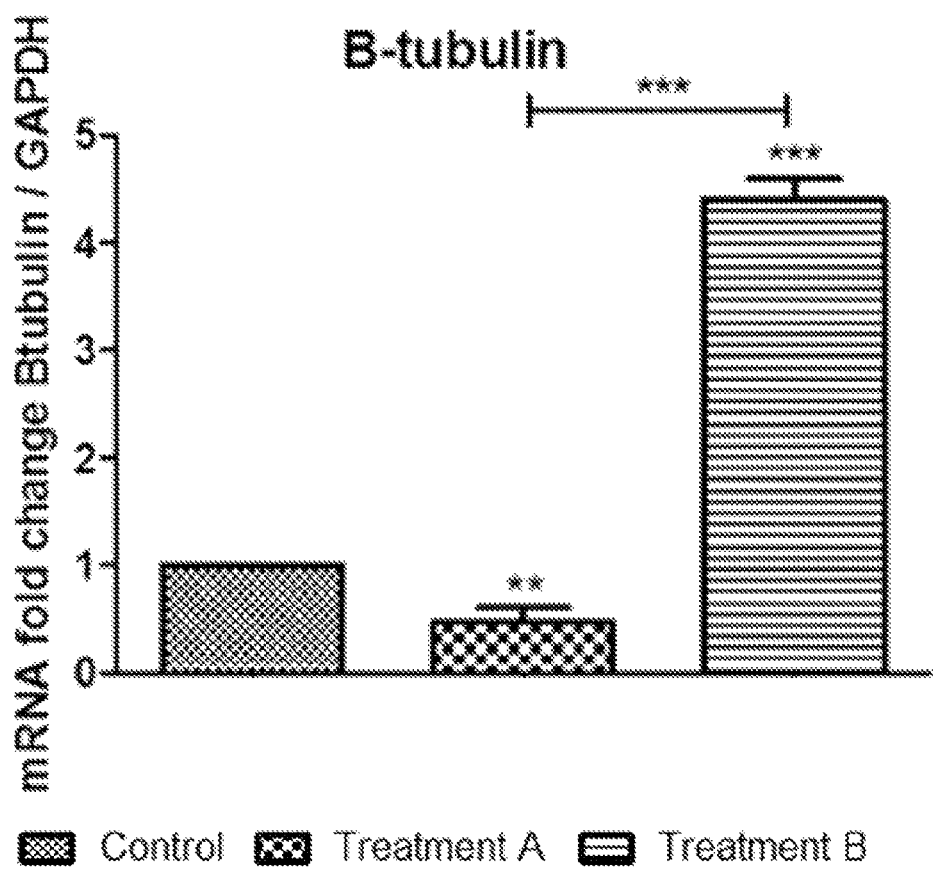
Figure 4:
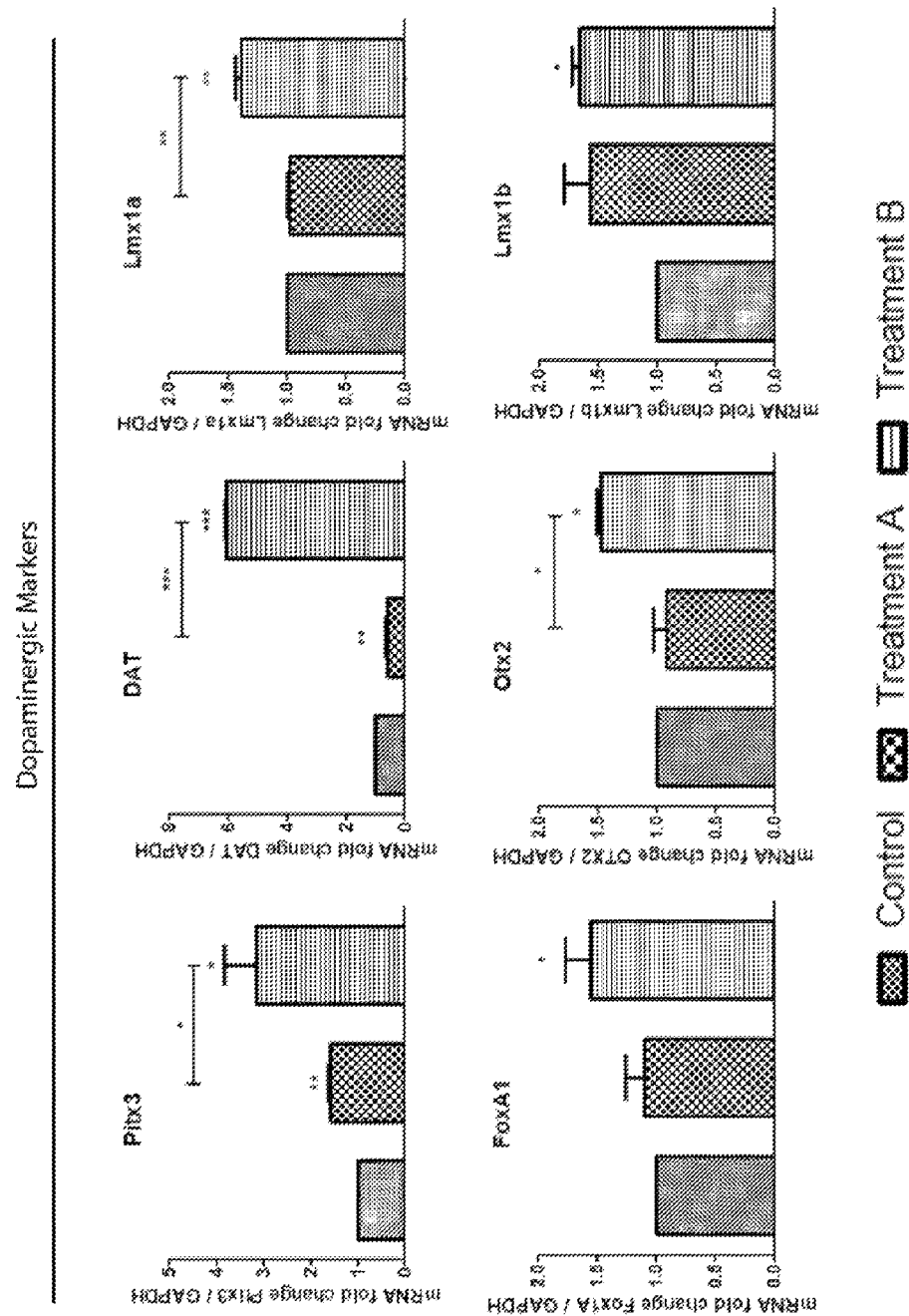

A common method in the art to assess the size of a potential stem cell population in a tissue is to test the number of 1 cell-derived growing clones that can be derived in vitro from a population of cells obtained from the specific tissue. To assess the general frequency of clonogenic cells the limited dilution technique was used and the results were analyzed according to Poisson distribution. The results indicate that 1 in 1.88 cells in the hOMSC population is a clonogenic cell (Marinka-Kalmani et al 2010 ibid). Interestingly, explants from gingival lamina propria re-explanted successively continue to generate several successive generations of primary cultures with equivalent growth abilities, suggesting that these explants contains a stem cells population with high self renewal capacity. A cell population derived from the lamina propria of the gingival oral mucosa was passaged for 13 passages which are equivalent to 40 population doublings (PD). The CFE of this population at P1 was 8.75%, peaked to 31% at P7 and declined to 14.5% at P13 (FIG. 4). These results strongly indicate that primary gingival populations are enriched with stem cells.

Multipotency

A common method in the art to assess the size and potency of a whole population is to test its plasticity, that is, the capacity of this population to differentiate into various cell lines of various tissues. The higher the proportion of stem cells in the population the higher the propensity of this population to differentiate into a larger number of cell lines. In such an experiment it was found that in contradistinction to other whole non-bone marrow derived-mesenchymal populations (e.g. dermal fibroblasts) the whole populations differentiated into osteoblastic and adipocytic lineages as reflected by the formation of alizarin red and oil red positive cultures. The results demonstrate that the whole cell population of the lamina propria of the gingiva is enriched with a relative high number of multipotent mesenchymal stem cells. To assess the proportion of multipotent stem cells in the whole populations, these were labeled with antibodies known as characteristic for mesenchymal stem cells and the number of labeled cells was assessed by FACS. The results obtained from 3 donors indicate that more 95% of the cells where labeled for at least two mesenchymal stem cell markers, demonstrating that essentially the whole population of gingival lamina propria consisted of multipotent stem cells. Therefore, whole populations of oral mucosa can be used "as is" without further purification, as a source for multipotent stem cells capable of differentiating into a variety of cell lineages under in vivo and/or in vitro conditions. This finding is unique to cell population derived from the oral mucosa and was not observed in any adult tissue.

Pluripotency

Pluripotency refer to the capacity of a cell population to differentiate to any cell lineage of the adult organism. This property is usually attributed to the embryonic stem cells (ESCs). ESCs are characterized by a number of surface and nuclear markers such as: SSEA3, SSEA4, Tra-1-61, Tra-1-81 and Oct-4. In an experiment in which some of these markers were tested by immunofluorescence microscopy on cell population obtained from the oral mucosa of 3 donors more than 50% of the cells were positive for at least one of these markers. No other adult tissue known in the art was found to contain such a high proportion of pluripotent stem cells as evidenced by their capacity to express markers characteristic to embryonic stem cells. This finding is unique to cell populations derived from the oral mucosa and was not observed in any adult tissue. Therefore, oral mucosa is the best source for obtaining pluripotent stem cells in the adult that are capable of differentiating into cell lineages of mesodermal and ectodermal in vivo and in vitro conditions and endodermal origin under in vitro conditions.

Examples of cell lineages of ectodermal origin that can be obtained from oral mucosa derived pluripotent stem cells are: neural cells (neurons, astrocytes, oligodendrocytes and Schwann cells), keratinocytes lining the skin and the oral cavity, glandular epithelium (salivary epithelium, sweat gland epithelium), hair follicle epithelium, corneal epithelium, glandular cells of the adenohypophysis and adrenal medulla, ameloblasts and any other epithelial cell line that is derived from the embryonic ectoderm. Examples of tissues and organs that can be treated and/or repaired or regenerated by utilizing pluripotent stem cells derived from the oral mucosa or the herein mentioned ectodermal cell lineages generated from oral mucosa derived stem cells or the combination of these are: epidermis, the epithelial component of the oral mucosa, nervous tissue, cornea, salivary glands, hair, respiratory epithelium and any other tissues or organs derived from the embryonic ectoderm.

The following examples are intended to illustrate how to make and use the compounds and methods of this invention and are in no way to be construed as a limitation. Although the invention will now be described in conjunction with specific embodiments thereof, it is evident that many modifications and variations will be apparent to those skilled in the art. Accordingly, it is intended to embrace all such modifications and variations that fall within the spirit and broad scope of the appended claims.

EXAMPLES

The results described below were obtained mainly from cell populations derived from the lamina propria (not including the epithelial part) of the human gingiva which is an integral part of the oral mucosa lining the oral cavity.

Material and Methods

Antibodies

Primary Antibodies: For flow cytometry: mouse monoclonal anti CD105-PE, mouse monoclonal anti CD90-PE, mouse monoclonal anti CD45-PE, mouse monoclonal anti CD29-FITC, mouse monoclonal anti HLA-ABC-PE, mouse monoclonal anti HLA-DR-PE, mouse monoclonal anti TRA-1-60-PE and mouse monoclonal anti TRA-1-81-PE were obtained from eBioscience (San Diego, Calif., USA); mouse monoclonal anti-CD73-PE was obtained from BD Bioscience (San Jose, Calif., USA); mouse monoclonal anti CD106-PE, mouse monoclonal anti Tra 2-49 and mouse monoclonal anti Tra 2-54 from Chemicon (Temecula, Calif., USA); Mouse monoclonal anti CD166-PE, mouse monoclonal anti CD117-FITC, mouse monoclonal anti Stro-1, mouse monoclonal anti SSEA1-PE, rat monoclonal anti SSEA3, mouse monoclonal anti SSEA4-PE, mouse monoclonal anti Sox2-PE, Goat polyclonal anti Nanog, mouse monoclonal anti CD146-PE, rat monoclonal anti Oct4-PE and mouse monoclonal anti Nestin-FITC from R&D Systems (Minneapolis, Minn.); mouse monoclonal anti CD34-FITC was from IQ products (DL, Groningen, The Netherlands).

For immuno-fluorescence: Rabbit polyclonal anti Sox2 was obtained from Abcam (Cambridge, U.K.); Goat polyclonal anti Nanog, mouse monoclonal anti Nestin, mouse monoclonal anti βIII-Tubulin (TuJ1), mouse monoclonal anti Oligodendrocyte 4 (O4), goat polyclonal anti Sox17, goat polyclonal anti FoxA2(hHNF-3β), mouse monoclonal anti aggrecan and mouse monoclonal anti CXCR4 were obtained from R&D Systems (Minneapolis, Minn.) and mouse monoclonal anti-Neu-N, rabbit polyclonal and anti Oct4 from Chemicon (Temecula, Calif., USA). Rabbit polyclonal anti p75 (Promega, Madison, Wis. USA), Mouse monoclonal anti Oct4 from Santa Cruz biotechnology (Santa Cruz, Calif. U.S.A.).

For immunohistochemistry: Mouse monoclonal anti collagen II and mouse monoclonal anti human mitochondria were from Chemicon (Temecula, Calif., USA) and antihuman S100B antibodies kit from DakoCytomation, Glostrup, Denmark.

Secondary antibodies: Secondary antibodies used were Goat polyclonal to Mouse IgG Cy3 conjugated from Abcam (Cambridge, U.K.), Goat polyclonal to mouse IgG FITC conjugated, Goat polyclonal to mouse IgM FITC conjugated, Goat polyclonal to Rabbit IgG Cy3 conjugated and Mouse polyclonal to Goat IgG FITC conjugated and mouse to mouse IHC detection system from Chemicon (Temecula, Calif., USA). Pepro Tech ELISA assay kits were used.

Immunophenotyping

Flow Cytometry Analysis

Cultures $P_4$-$P_7$ were harvested in trypsin—EDTA. Following trypsin inactivation with 10% FCS, cells were centrifuged, resuspended in blocking buffer (PBS+0.1% BSA and 0.01% sodium azide) and passaged through 70 μm strainer. For direct staining of cell surface antigens aliquots of 0.5-1×10$^6$ cells were transferred to FACS tubes, centrifuged, resuspended in 100 μl blocking buffer for 1 hour and stained with conjugated FITC or PE primary antibody according to the manufactures instructions. For indirect staining the cell aliquots were incubated with non-conjugated primary antibodies, centrifuged, washed with 3 ml blocking buffer and incubated with FITC-conjugated secondary antibody according to the manufactures instructions. For intracellular antigens staining single cell suspensions were fixed in 1.5% paraformaldehyde in PBS for 10 minutes, washed in 3 ml of blocking buffer, permeabilized in 0.1% TritonX100 for 10 min, washed in 3 ml of blocking buffer and stained as described above. Replacement of the conjugated primary antibodies by their identical conjugated isotype immunoglobulins and omission of the non-conjugated primary antibody served as controls for direct and indirect labeling, respectively. Following antibody labeling cells were washed in blocking buffer, centrifuged, resuspended in Mg and Ca free PBS and analyzed with a FACScan. FACS sorter WinMDI 2.9 was used to analyze the data. Each marker was analyzed in separate cultures obtained from 3-8 donors from each age group.

Tissue Immunofluorescence
  a. Gingival biopsies were fixed in 4% paraformaldehyde at 4° C. overnight, frozen in liquid nitrogen embedded in OTC and cut into 6 μm thick sections. Following permeabilization with methanol/ethanol (1:1 v/v) sections were stained with primary antibodies for p75, Sox2, Oct4 and Nanog and then with Cy3 conjugated secondary antibodies according to the manufactures instructions. Sections in which the primary antibody was replaced with PBS served as controls. For double staining sections were incubated for 10 min with ethanol, dried, incubated with 0.3% TritonX100 for 10 min, washed ×3 in PBS, blocked with 1% BSA for 40 min, incubated for 1 hr with mouse anti human Oct4 and rabbit anti human p75, rinsed ×3 in PBS and incubated for 1 hr with FITC-conjugated antimouse and Cy3-conjugated antirabbit antibodies according to the manufacturer instructions. Sections in which the primary antibodies were replaced with PBS served as controls. Sections were covered with a DAPI containing mounting solution, and visualized and captured with a Zeiss Axioplan light and fluorescent microscope.
  b. Cultures are washed with PBS, fixed in 1% paraformaldehyde in 125 mM HEPES (pH 7.6; 10 min, 4° C.) and for intracellular markers permeabilized in 0.5% Triton X-100 in PBS (30 min,), blocked with 10% non-immune serum, incubated with the selected primary antibodies, rinsed in PBS, blocked in PBS supplemented with 1% BSA, 0.2% fish skin gelatin, 0.1% casein, rinsed in PBS and reacted with fluorescent secondary antibodies, rinsed 3× time in PBS, mounted in VectaShield labeled with DAPI (Vector Labs) and visualized with a Zeiss Axioplan2 photomicroscope equipped for fluorescence. For double staining the same procedure is used, except that, both primary antibodies and then secondary antibodies are incubated simultaneously. Cultures incubated with non-immune serum and secondary antibodies serve as negative controls. (Protocol modified from Pitaru S et al. Connect Tissue Res., 2002, 43:257-264).
  c. For indirect immunofluorescent identification of cell surface and intracellular antigens cells cultured in 8-wells Labtek chambers were washed in Mg and Ca free PBS, fixed for 10 min in 4% cold paraformaldehyde, washed 2 times with PBS and permeabilized for 10 min with 0.1% Triton X-100. For cell surface markers staining the Triton X-100 step was omitted. Then, cultures were incubated with blocking solution consisting of PBS+1% BSA for 45 min, labeled with primary antibodies according to the manufactures instructions, washed 5 times for 2 minutes in PBS and incubated with FITS or Cy3 secondary antibodies for 30-60 min, washed ×8 in PBS and mounted with mounting medium containing DAPI. Cultures in which the primary antibody was replaced with goat serum or PBS served as controls. Staining was visualized and captured with either a Leica confocal microscope or with a Zeiss Axioplan fluorescent microscope.
  d. Cells were fixed in 4% paraformaldehyde-PBS and pre-incubated for 60 min in blocking solution (5% goat serum, 1% BSA, 0.05% Triton-X in PBS). Primary antibodies were diluted in the blocking solution and applied overnight at 4° C. Fluorophore-conjugated secondary antibodies were diluted in PBS and applied for 1 hour. For DA cells the following antibodies were used: Neuronal markers anti β-III-Tubulin (1:200, AB7751, Abcam), anti-Map2 (1:200, AB5622, Chemicon) and anti-synapsin (1:200, AB1543, Millipore). DA neuron markers, anti-tyrosine hydroxylase (1:200, B152, SIGMA), anti-Lmx1a (1:200, MB369, Chemicon), anti-Pitx3 (1:200, AB5722, Chemicon) and anti-Nurr1 (1:200, AB5778, Millipore). For NS cells the following antibodies were used: GFAP antibody (1:200, DAKO, Denmark), S100β (1:200, Sigma Aldrich), BDNF (1:100; Santa Cruz Biotechnology Inc., USA), GDNF (1:100, Santa Cruz Biotechnology Inc., USA), IGF-1 (Santa Cruz Biotechnology Inc., USA), VEGF (Santa Cruz Biotechnology Inc., USA). Primary antibodies were detected with fluorescently labeled secondary antibodies Alexa 488 and 568 (1:500, Molecular Probes) for 1 h at room temperature. Negative control and photography exposition settings were obtained by incubation of the secondary antibody only at the same concentration used for the samples. Nuclear DNA was stained using 4,6-diamino-2-phenylindole (DAPI) (1:1000, Sigma). Photographs were taken with a fluorescence Olympus IX70-S8F2 microscope with a fluorescent light source (excitation wavelength, 330-385 nm; barrier filter, 420 nm) and a U-MNU filter cube (Olympus, Center Valley, Pa.). Fluorescence quantification was performed by integrated density of fluorescence by Image J software (National Institutes of Health, Bethesda, Md., USA).

Western Blot

Cells were lysed in buffer containing PBS, 1% SDS, complete protease inhibitor (SIGMA) and loaded into SDS-PAGE 12%. Three independent cultures were used as biological replicates. Gels were transferred using liquid transference (300 mA, 1.15 hs) and membranes were blocked using PBS buffer 5% milk for 2 hr at room temperature. The membranes were probed with anti-TH (SIGMA), anti-Pitx3 (Chemicon) and anti-actin (Chemicon), followed by IRDye (680, 800 nm) or horseradish peroxidase conjugated secondary antibody (LI-COR). The membrane was analyzed and bands quantified with Odyssey infrared imaging systems (LI-COR).

hOMSC Culture hOMSC were obtained from oral mucosa biopsies particularly of gingival origin from donors aged 25-80 years as described above and in WO 2008/132722.

Briefly, gingival or alveolar mucosa biopsies 3-4×2×1 mm were minced and explants were cultured in 25 cm² tissue culture flasks and cultured in low glucose Dulbecco's modified Eagle's medium (LGDMEM) supplemented with 100 μg/ml streptomycin, 100 U/ml penicillin, (Biological Industries, Beit-Haemek, Israel), glutamine 2 mM (Invitrogen) and 10% fetal calf serum (FCS) (Gibco) as described by Marinka-Kalmani et al 2010 (ibid). This medium is referred as expansion medium or "Growing Medium". The term "Control Medium" is used for serum free conditions. For expanding primary cultures ($P_0$), these were grown to 70% confluence, harvested and aliquots of $10^5$ cells were passaged into 25 cm² tissue cultures flasks and cultured to 50% confluence and passaged repetitively.

Midbrain Mouse Primary Culture

Mouse mesencephalic primary cultures were performed according to Fasano et al. 2008 (Fasano C, et al., Curr Protoc Neurosci. 2008; Chapter 3:Unit 3 21), using four days old newborn mice. 250.000 cells were seeded in 24 well-plates and examined for dopaminergic neurons markers analysis after fixation with PFA 4%.

Dopaminergic Induction of hOMSC

To induce dopaminergic differentiation hOMSC were subjected to two different protocols, denoted Treatment A and Treatment B. Treatment B is a novel protocol disclosed and used herein for the first time. Both protocols include first an induction stage of 48-72 hr during which hOMSC were cultured in serum free medium (DMEM low glucose) supplemented with N-2 (GIBCO) and basic Fibroblast Growth Factor 2 (bFGF) (R&D Systems) and Epidermal Growth Factor (EGF) (R&D Systems), each at a final concentration of 20 ng/mL. Thereafter, hOMSC cultures designated for Treatment A (Barzilay R, et al. Stem Cells Dev. 2008; 17:547-554) were incubated for 4 days in Neurobasal® medium (Invitrogen) supplemented with 0.5% B27 (Invitrogen), 0.5 mM IBMX (SIGMA), 1 mM dbcAMP (SIGMA), 200 μM ascorbic acid and 50 ng/mL Brain Derived Neurotrophic Factor (BDNF) (Peprotech). hOMSC allocated for Treatment B, were incubated for 13-15 days in Neurobasal® medium (Invitrogen) supplemented with 0.5% B27 (Invitrogen), 250 ng/mL Sonic Hedgehog (Shh), 100 ng/mL of Wnt-1 and FGF-8, 50 ng/mL of BDNF and bFGF and 200 μM of ascorbic acid. All factors used in treatment A or B were obtained from PeproTech unless otherwise specified.

Neuron Supporting Cell Induction of hOMSC

A two-step medium based differentiation protocol was performed. In the first step, the cells were incubated in serum free conditions (DMEM low glucose/SPN/Glutamine) with the addition of N2 supplement (GIBCO), basic Fibroblast Growth Factor 2 (bFGF) (R&D Systems) and Epidermal Growth Factor (EGF) (R&D Systems) at a 20 ng/mL final concentration. Following 72 hr., the second differentiation step was initiated. Cells were incubated in serum free medium (DMEM low glucose/SPN/Glutamine) with the addition of dbcAMP (1 mM) (SIGMA), IBMX (0.5 mM) (SIGMA), Neuregulin (50 ng/mL) and PDGF (1 ng/mL) (Peprotech) for additional 72 hrs. The differentiation protocol was performed in cells that didn't undergo more than ten passages.

For all differentiating protocols, the differentiation medium of the culture or suspension of cells is replaced during the incubations, as required to maintain the medium conditions.

Real Time PCR:

a. Total RNA is isolated by using RNeasy mini kit (Qiagen Inc., Valencia, Calif.) according to the manufacturer's instructions. Ten μg of total RNA is used as template for single strand cDNA synthesis in a reaction using oligo (dT) primers and Moloney murine leukemia virus-reverse transcriptase (Invitrogen) according to the manufacturer's protocol. Real Time PCR is performed in triplicate with SyBr Green PCR Master Mix (ABI) and 200 nM each of forward and reverse primers. PCR is performed with a 10-min hot start at 95° C., followed by 40 cycles of 30 s at 95° C. and 1 min at 61° C. The average threshold cycle (Ct) for each gene is determined from triplicate reactions, and levels of gene expression relative to glyceraldehyde-3-phosphate dehydrogenase (GAPDH) are determined.

b. Total RNA was isolated by TM reagent (Invitrogen) according to the supplier's recommendations. 2 μg of RNA was used for reverse transcription performed with random primers and SuperScriptIII (Invitrogen). Real-time PCR of the genes of interest was performed in an ABI Prism 7700 sequence detection system (Applied Biosystems) by using Platinum® SYBRR Green qPCR SuperMix UDG with ROX (Invitrogen). PCR amplification, using the primer sequences detailed in Table 1, was performed by 40 cycles (program: 2 min at 50° C.; 2 min at 95° C.; 40 repeats of 15 s at 95° C. and 30 s at 60° C.). Data were quantified by using the ΔΔCT method and averaged upon normalization to the GAPDH gene.

TABLE 1 primer sequences used

| Gene | Sense | SEQ ID NO: | Antisense | SEQ ID NO: |
|---|---|---|---|---|
| GAPDH | CGACAGTCAGCCGCATCTT | 1 | CCAATACGACCAAATCCGTTG | 2 |
| LMX1a | CCTGCAGGAAGGTGAGAGAGA | 3 | TGGACGACACGGACACTCAG | 4 |
| Sox2 | CAGGAGAACCCCAAGATGC | 5 | GCAGCCGCTTAGCCTCG | 6 |
| NGN2 | CAACTAAGATGTTCGTCAAATCCG | 7 | CCTTCAACTCCAAGGTCTCGG | 8 |
| MASH1 | AGCAGGGTGATCGCACAAC | 9 | ACGCCACTGACAAGAAAGCACTA | 10 |
| En1 | GTTATTCGGATCGTCCATCCTC | 11 | CGCCTTGAGTCTCTGCAGCT | 12 |
| Pitx3 | GTTCGCTGAAAAAGAAGCAGC | 13 | TCTGGAAGGTCGCCTCTAGCT | 14 |
| Nurr1 | GGATGGTCAAAGAAGTGGTTCG | 15 | CCTGTGGGCTCTTCGGTTT | 16 |
| VMAT2 | CCGCCCTGGTACTCTTGGAT | 17 | TCCCCTTCTGACTCTCTGGCT | 18 |
| Dopamine transporter | CTGGAGCCATAGACGGCATC | 19 | CCGCGTCAATCCAAACAGA | 20 |
| NANOG | TGCCTCACACGGAGACTGTC | 21 | AGTGGGTTGTTTGCCTTTGG | 22 |
| OTX2 | CGAGGGTGCAGGTATGGTTTA | 23 | TCCCGAGCTGGAGATGTCTT | 24 |
| DAT | CCAGCAATGACCATGAAG | 25 | AGGCCACCCATGAGTAGG | 26 |
| FOXA1 | GGCTGAAACCAGCGACTG | 27 | AGGCTCCTGCGTGTCTG | 28 |
| GDNF | CAAATATGCCAGAGGATTATCCTG | 29 | GCCATTTGTTTATCTGGTGACCTT | 30 |
| BDNF | AGCTCCGGGTTGGTATACTGG | 31 | CCTGGTGGAACTTCTTTGCG | 32 |
| NGF | CATGCTGGACCCAAGCTCA | 33 | GACATTACGCTATGCACCTCAGTG | 34 |
| GFAP | TAGAGGGCGAGGAGAACCG | 35 | GTGGCCTTCTGACACAGACTTG | 36 |
| EAAT2 | CGAAGGCCTGCAGAGACC | 37 | AGGGTATACTCCTGCTCCATGC | 38 |

Dopamine Quantification

Cellular dopamine release determination was performed by reverse-phase HPLC, using three independent cell cultures for each condition. Medium of differentiated and naïve cell cultures was replaced first with Hanks Balanced Salt Solution (HBSS) buffer for 35 minutes at 37° C. Then, the HBSS buffer was replaced with new HBSS supplemented with 56 mm KCl to induce membrane depolarization. The supernatant was collected and stabilized with 4 mM sodium meta-bisulfite (SIGMA) and 1 mM EDTA (SIGMA), and stored at −80° C. Dopamine was extracted by aluminum adsorption and analyzed by injection (20 µl) into a HPLC system (Waters, Milford, Mass., USA) equipped with a C18 reverse phase, 3 µm LUNA column (100 mm×2 mm; Phenomenex, Torrance, Calif., USA). The sample was eluted by a mobile phase made of 25 mM NaH2PO4, 50 mM Na-citrate, 0.03 mM EDTA, 10 mM diethylamine HCl, and 2.2 mm sodium octyl sulfate (pH 3.2), 30 mL/L methanol and 22 mL/L dimethylacetamide at a flow rate of 0.4 mL/min. The dopamine peak was determined by electrochemical detection at a potential of 0.6 V. The dopamine content in the sample was calculated by extrapolating the peak area from a standard curve (range 1-200 pg of dopamine) constructed under the same conditions during each run by the Maxima Workstation (Waters). For brain samples, animals (n=8/group) were sacrificed by CO2, brains were quickly removed and kept on ice. Hemispheres were divided and homogenized in ice cold 0.1 perchloric acid. Samples were centrifuged and supernatants were transferred into 0.2 µm nylon filers (Costar). Filtrates were analyzed for dopamine content as described above.

6-OHDA Lesion, Cell Transplantation, and Behavioral Analysis

Rats were maintained under 12-hour-light/12-hour-dark conditions and grown in individually ventilated cages (IVC) with ad libitum access to food and water. All experimental protocols were approved by the Tel Aviv University Committee of Animal Use for Research and Education. Every effort was made to reduce the number of animals used and to minimize their suffering. Two independent experiments were performed. For each experiment hOMSC obtained from a different donor were used. In each experiment 21 adult rats (230-250 g) were anaesthetized with ketamine and xylazine (60 mg/kg and 10 mg/kg, respectively) and placed in a stereotactic frame. The DA denervation was done by 6-OHDA (6 µL; 2.5 mg/ml in normal saline with 0.02% ascorbic acid) stereotactic injections into the medial forebrain bundle (MFB) (anterior −4.0 mm; lateral −1.3 mm; ventral −7.7 mm, as determined from the bregma and the skull surface). Differentiated and naive cells were labeled with PKH26 (SIGMA), harvested and resuspended at a concentration of 1×10$^5$ cells/µL of saline, and maintained at 40 C on ice until transplantation. Each type of cell suspension was inoculated into the affected striatum at two different coordinates by injection of 4 µL in each point (AP −0.8 ML −4.2 DV −5.5, AP 0.0 ML −2.8 DV −4.6). Trypan blue staining was performed in parallel aliquots to ascertain 99% cell viability. An additional control group of animals were inoculated with 100 µL of saline. The effect of cell transplantation on motor function was assessed by 3 assays: i) amphetamine induced turning behavior was measured for 60 min using an automated Rotameter device (San Diego Instruments) by s.c. injection (2.5 mg/kg) (SIGMA). The net ipsilateral rotations were measured 2 weeks after 6-OHDA injection. Only rats with two or more rotations/min, were used for cell transplantation purposes (saline and hOMSC n=12, hOMSC-DA n=13). Rotations were assessed 2, 4 and 8 weeks post-transplantation; ii) motor asymmetry was measured by the cylinder test three weeks after cell transplantation (saline n=7, hOMSC n=4 and hOMSC-DA n=9). The number of wall contacts with each forelimb when rearing in at least 15 rearing cycles was computed. Data was expressed as cylinder test score, as follows: (use of the lesioned forepaw (contralateral)−intact forepaw (ipsilateral))/total (contra+ipsi+both); iii) motor activity was measured using the San Diego Instrument test, Rotor-Rod (San Diego Instruments, CA, USA) two days before cell transplantation and 1, 2 and 4 weeks after (saline and hOMSC n=8, hOMSC-DA n=9). This test measured the time that the rats remained on a rotating rod at accelerating speed (0-25 RPM). The average time measured in three consecutive runs for each rat was recorded and the groups' performance was compared. Data is presented as percentage values of each individual (Mean±SEM) relative to the initial time they spent on the rod before injury. The differences between the animal numbers used for each motor test is due to the two independent experiments. For the amphetamine-induced rotations a combination of both experiments was performed, while rotorod and cylinder test were performed only in the second experiment.

Brain Tissue Analysis

For immunodetection, rats (n=4/group) were anesthetized and perfused with PFA 4%. Brains were extracted, sectioned (10 μm) by cryostat and deposited into glass slides. Brain slides were blocked in 5% goat serum, 1% BSA, 0.05% Triton-X in PBS for 2 hr., and incubated with their respective antibodies for further analysis. For fluorescence and chemical based TH detection, antigen retrieval was performed by boiling the slides in citrate buffer 10 Mm for 10 min was performed. For TH chemical detection DAB (3-3' diaminobenzidine) peroxidase kit (VECTOR Laboratories) was used. Same animals were used for immunochemistry and immunofluorescence, and 6 slides/animal were used for immunodetection and further analysis.

ELISA Based Measurement of NTFs Secretion

At the end of the differentiation process, human VEGF and BDNF concentrations in the cell culture supernatant were measured using a sandwich ELISA procedure according to the manufacturer's instructions (DuoSet, R&D System for human BDNF and VEGF). Briefly, supernatant media samples (100 μL) were measured in triplicate per flask. The samples were incubated overnight on coated plates, followed by exposure to a second antibody and streptavidin-HRP based detection ($H_2O_2$ and tetramethylbenzidine solution). The absorbance at 450 nm and 570 nm was recorded using a Microplate Reader. The results were calculated for one million cells.

Cell Viability Assay

The ability of undifferentiated and differentiated hOMSC conditioned media to protect motor neuron cell-line (NSC-34) from hypoxic and oxidative stress was tested. NSCs-34 were plated in 96 well plates at a 10.000 cells/well and placed in a hypoxic environment for 72 hours in a chamber together with the respective conditioned media. After 72 hours, Alamar blue 10% (AbDSerotec, Kidlington, UK) was added to the cells to quantify viability. The assay was conducted in triplicate and results were read at wavelengths of 590 nm using a fluostar device. Results were normalized to cells under the same treatments in normoxia. For oxidative stress studies NSC34 cells were exposed to 25 μM hydrogen peroxide (SIGMA) and incubated with conditioned media of undifferentiated and differentiated hOMSC for 24 hrs. Data was normalized and expressed as percentage of cells present in serum free conditions with no insult.

Sciatic Nerve Injury and Cell Transplantation

The sciatic nerve crush model was applied on male Sprague-Dawley rats (n=24; Harlan, Jerusalem) weighing 230-250 g. Rats were placed under 12-hour-light/12-hour-dark conditions and grown in individually ventilated cages (IVC) with ad libitum access to food and water. All experimental protocols were approved by the Tel Aviv University Committee of Animal Use for Research and Education. Every effort was made to reduce the number of animals used and to minimize their suffering. Two independent experiments of 4 animals/group (total=8/group) was performed. For each experiment two different donors were used, obtaining reproducible results.

Rats were anesthetized with Chloral hydrate (300 mg/kg) (Sigma-Aldrich, St. Louis) and subcutaneous daily cyclosporine was given (3.75 mg/rat) (Novartis). The right or left sciatic nerve was exposed and a vessel clamp was applied 10 mm above the first branching of the nerve, for 30 seconds. Then, the muscle and skin were closed in layers. After 24 hr. differentiated and naïve cells were harvested, labeled with superparamagnetic iron oxide (SPIO) (5 g/ml; Feridex; Bayer HealthCare, Leverkusen, Germany), centrifuged, resuspended at a concentration of $1 \times 10^6$ cells/100 μL of saline, and maintained at 40° C. on ice until transplantation. Each type of cell suspension was inoculated in the vicinity of the damaged sciatic nerve by injection in each of 16 animals (8 rats/group). Trypan blue staining was performed in parallel aliquots to ascertain 98% cell viability. An additional control group of 8 animals were inoculated with 100 μL of saline only.

Motor activity was measured using the San Diego Instrument test, Rotor-Rod (San Diego Instruments, CA, USA) between days 1 at 10 after cell transplantation. This test measured the time that the rats remained on a rotating rod in accelerated speed (0-25 RPM). Following a brief training period, adult Sprague Dawley rats were able to remain balanced in the rod for up to 4 minutes. After sciatic nerve crush the rat's ability to balance is severely compromised, hence causing the animal to falloff the rod after shorter periods of time. The average time measured in three consecutive runs for each rat was recorded and the groups' performance was compared. The machine has a laser beam that detects the fall. Rotor-rod test was assessed at days −1, 0, 2, 4, 6 and 10 after transplantation. Data is presented as percentage values of each individual (Mean±SEM) relative to the initial time they spent on the rod before injury.

Assessment of Cell Engraftment and Phenotype Maintenance

To analyze cell survival following transplantation, rats were sacrificed with $CO_2$, hind limb muscles were removed and frozen in liquid nitrogen, 10 days after transplantation (n=5/group). Muscles were sectioned at 20 μm using a cryostat (Leica CM1850) and placed on glass slides for staining. The sections were fixed with 4% PFA-PBS and dyed with Prussian blue staining (Accustain, Sigma Aldrich) to detect the SPIO-labeled transplanted cells. Nuclear DNA was stained using 4,6-diamino-2-phenylindole (DAPI) (1:1000, Sigma). Photographs were taken with a fluorescence Olympus IX70-S8F2 microscope with a fluorescent light source (excitation wavelength, 330-385 nm; barrier filter, 420 nm) and a U-MNU filter cube (Olympus, Center Valley, Pa.). Fluorescence estimation was performed by integrated density of fluorescence by Image J software (National Institutes of Health, Bethesda, Md., USA).

Assessment of Neuromuscular Junction (NMJ) Innervations

Hind limb muscles were dissected and frozen in liquid nitrogen (n=5/group). Muscles were sectioned at 20 μm using a cryostat and placed on glass slides for staining. Sections (n=10/animal) were fixed with 4% PFA-PBS and labeled with alpha-bungarotoxin conjugated with fluorescence marker Alexa Fluor 594 (1:500, Invitrogen, CA, USA) and anti-synaptophysin (rabbit polyclonal, 1:500, Santa Cruz Biotechnology, Santa Cruz, USA) antibodies overnight at 4° C. After washing with PBS, the sections were incubated with anti-rabbit Alexa Fluor 488-conjugated antibody (1:1, 000, Invitrogen) for one hour at room temperature followed by washes and covered with cover glasses using aqueous mounting medium (Invitrogen). NMJs were classified into two groups based on the degree of innervation of postsynaptic receptor plaques by nerve terminals. Endplates were scored as "innervated" if there was an overlap with the axon terminal, or "denervated" if the end plate was not associated with an axon.

Statistical Analysis

Results are expressed as mean±SEM. All analyses were performed using SPSS version 19 software. Differences between two groups were statistically analyzed by Student's T test, while comparisons between three groups were analyzed by One Way ANOVA. For the cell transplantation in vivo experiment, Two Way ANOVA was performed. Tukey's multiple comparison posthoc test was used to evidence specific differences between groups. Significance levels are as follows, * $p<0.05$,  $p<0.01$, * $p<0.001$.

Example 1

Analysis of Basal State hOMSC Cultures

Figure 1B:
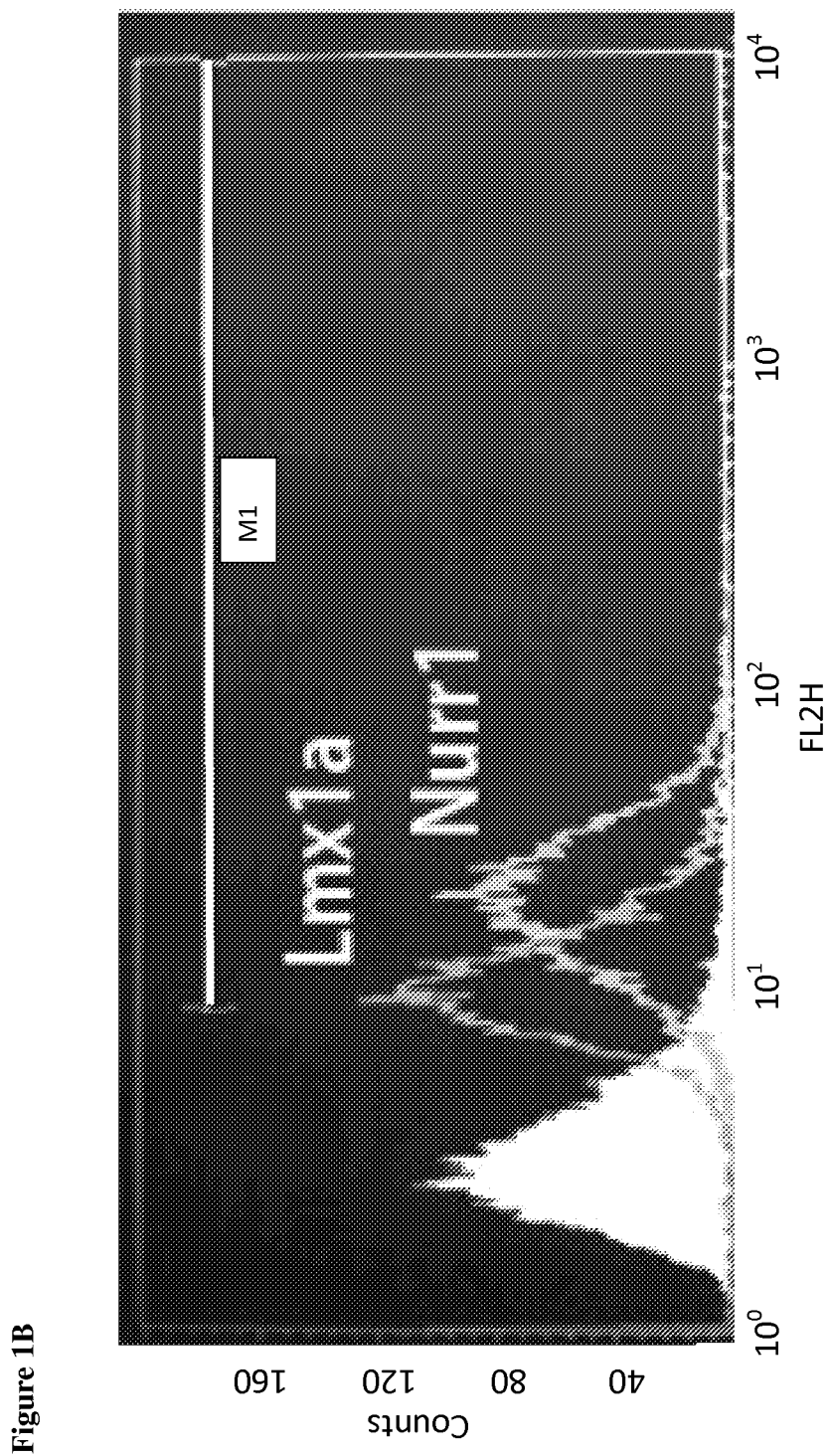

Undifferentiated hOMSC express constitutively neuronal and dopaminergic markers: hOMSC cultured in expansion medium (10% FCS) exhibit constitutive expression of neural markers. The expression of the neuronal markers TUJ1 (β-TubIII), MAP2 and Synapsin was observed. hOMSC also express constitutively the dopaminergic neurons markers Lmx1a and Nurr1. Interestingly, the DA transcription factors were localized in the cytoplasm with no nuclear localization evidence. Flow cytometry analysis revealed that 86% and 68% of hOMSC express constitutively Lmx1a and Nurr1 respectively (FIGS. 1A and 1B respectively). The antibody specificity was evident in mouse midbrain primary cultures, where only a small fraction of cells were positively stained, as expected by the small proportion of dopaminergic neurons present and the cross reactivity of the antibody between human and mouse. It was also found that in midbrain primary culture, positive cells for Nurr1 and Lmx1a exhibited predominantly nuclear localization, in contrast to the cytoplasmic localization of these transcription factors in hOMSC.

Example 2

DA Neuronal Markers Expression after Dopaminergic Differentiation hOMSC exhibit neuronal-like morphology after differentiation: Two different protocols for the differentiation of hOMSC into DA-like neurons were tested. The first protocol (treatment A) was reported by us in 2008 (Barzilay R, et al. ibid). The second one (treatment B) is a new designed protocol based on new data that become available regarding the signal pathways involved in dopaminergic differentiation during the midbrain development. Both differentiation protocols are detailed in Materials and Methods. While hOMSC in the control group did not undergo morphological changes, treatment A and B produced notable changes in hOMSC morphology from fusiform to a neuronal-like one (FIG. 2). Morphological changes were characterized by the appearance of bipolar and multipolar cells, presenting numerous projections emerging from the cell body, as seen by bright field microscopy.

Example 3

Evaluation of Stem Cells Markers

Figure 3:
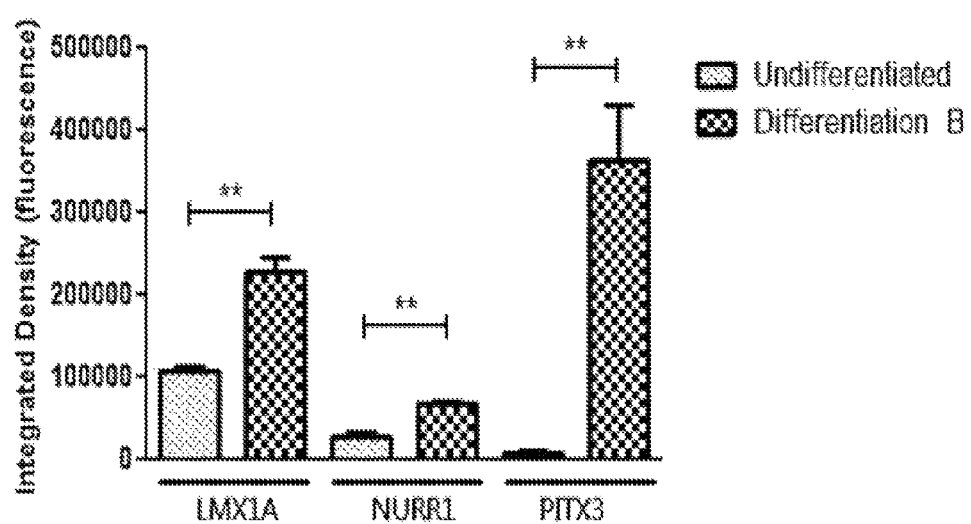
FIG. 3. Induction of differentiation in hOMSC increased the expression of DA markers. Real Time PCR analysis of differentiated hOMSC with either treatment A or B. The analysis show increased neuronal and dopaminergic markers, as well as reduced hOMSC stem cell markers. Data is expressed as Mean±SEM, significance levels *p<0.05, p<0.01, *p<0.001.

Real time PCR analysis revealed a significant decrease in the stem cell markers Sox2 and Nanog after both differentiation processes (FIG. 3-4). Specifically, treatment B induced a more significant decrease in stemness markers than treatment A, suggesting a more advanced differentiated stage. Treatment B increased significantly the transcript levels for Tuj1 and for the DA markers Pitx3, DAT, Lmx1a/b, Foxa1 and Otx2 whereas treatment A did not affect the expression of these genes except for an increase in the level of Lmx1b. Thus, treatment B is more effective than treatment A in inducing the expression of specific DA genes in hOMSC.

Next, it was checked whether the enhanced expression of Lmx1a, Nurr1 and Pitx3 induced by treatment B was translated into an increase in protein expression. Given that treatment A didn't enhanced dopaminergic genes, evaluation of transcription factors by immunofluorescence was only performed in hOMSC induced with treatment B. Using quantitative immunofluorescence it was found that treatment B not only increased the synthesis of these proteins, but most importantly, this treatment induced their translocation to the nucleus suggesting function.

Example 6

Evaluation of Tyrosine Hydroxylase (TH) Expression and Dopamine Release

Figure 5A:
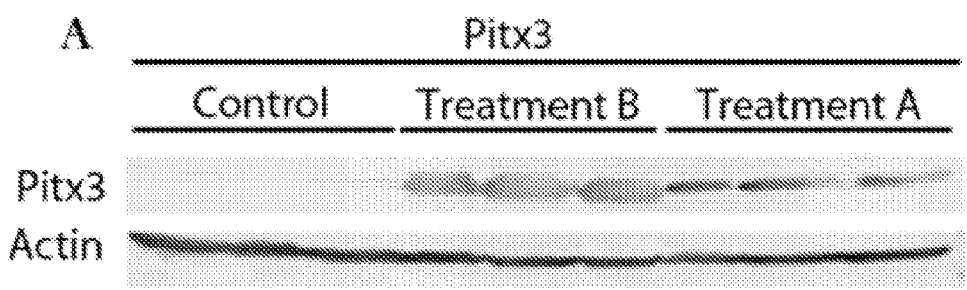
FIG. 5. hOMSC differentiated with treatment B express mature DA markers and secretes DA into the medium. Western blots and band densitometric quantification of mature DA-markers Pitx3 (5A, 5C) and TH (5B, 5D). Fluorescence quantification of TH immunocytochemistry (5E-5F) using ImageJ software. Conditioned medium of naïve, treatment A and B hOMSC after induction of dopamine release with KCl (5E). In the absence of KCl, treatment B-differentiated cells failed to secrete dopamine into the medium (5F). Data is presented as Mean±SEM. Significance levels *p<0.05, p<0.01, *p<0.001.
Figure 5B:
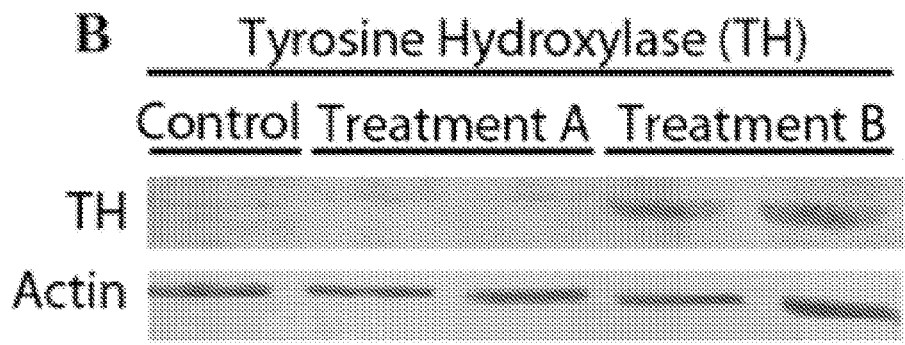
Figure 5C:
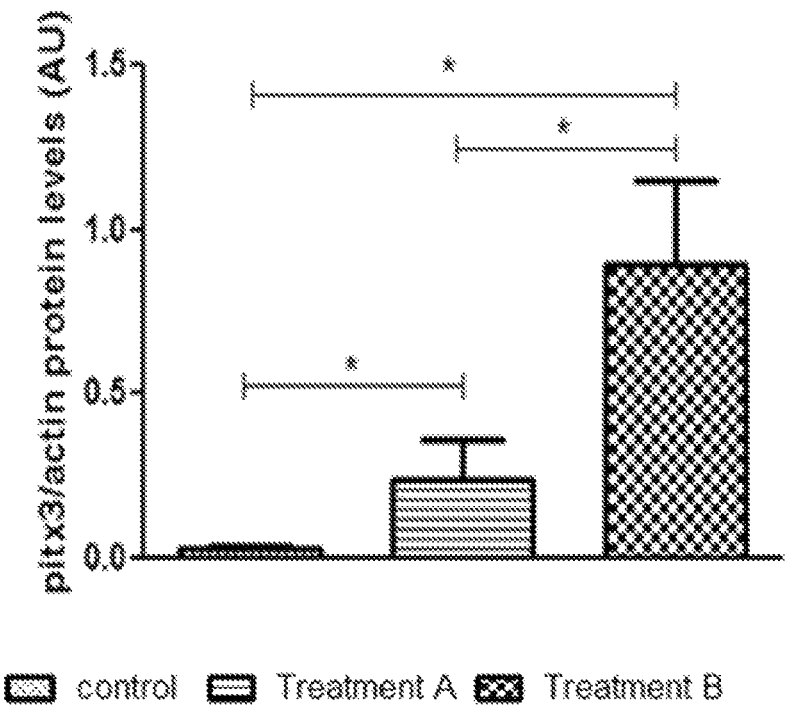
Figure 5D:
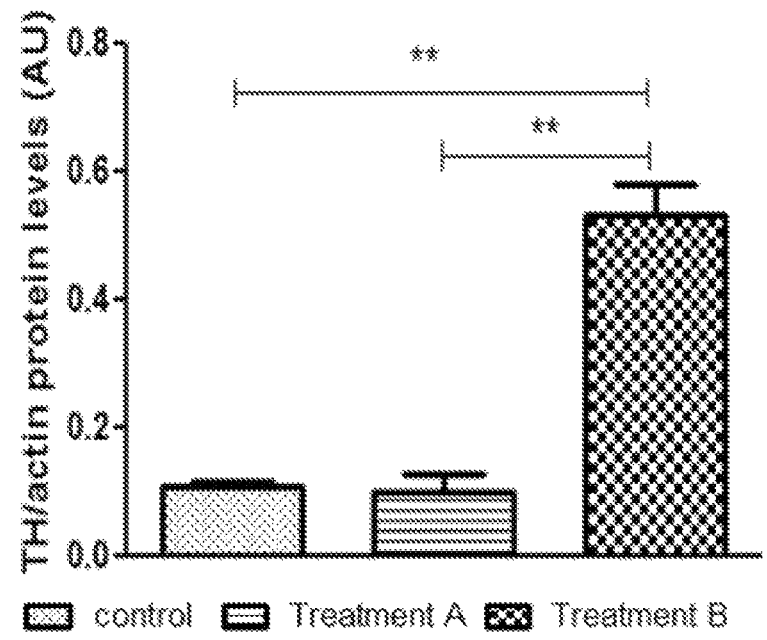
Figure 5E:
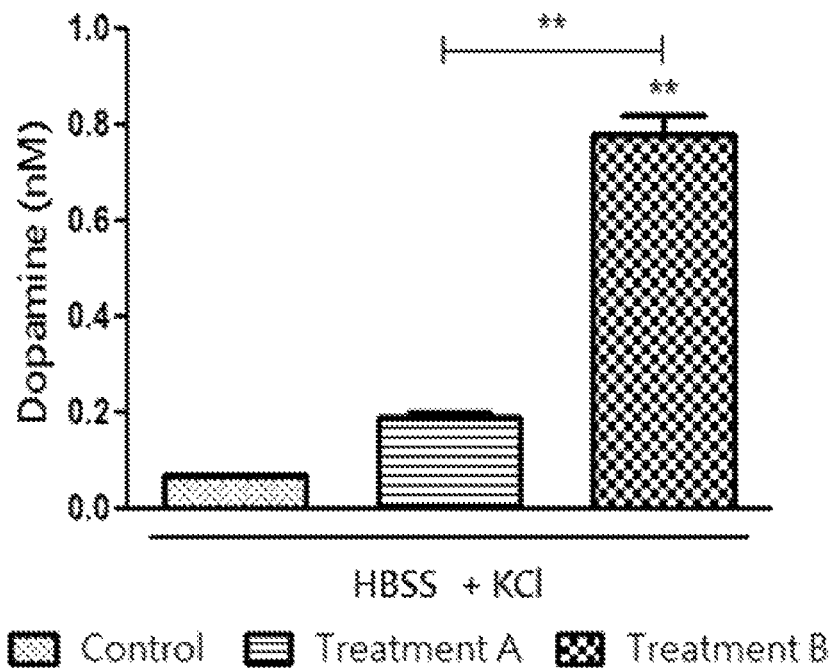
Figure 5F:
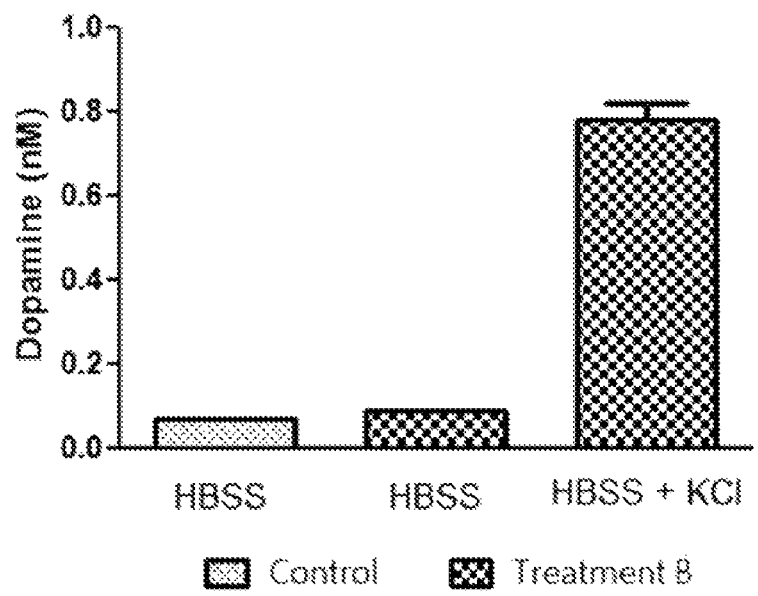

The level of mature DA markers at the protein level was evaluated by western blots in hOMSC cultures subjected to both differentiation protocols. The protein levels of the end-stage transcription factor Pitx3 and the characteristic DA marker, tyrosine hydroxylase (TH) were enhanced in the differentiated hOMSC cultures subjected to both treatments compared to control cultures (FIG. 5). However, treatment B significantly increased the expression of Pitx3 and TH by 10 and 5 fold respectively compared to treatment A (FIG. 5A-D). TH expression was also assessed by immunocytochemistry at the single cell and revealed that most of the cells induced with treatment B show a positive staining, while only few of the undifferentiated cells exhibited low signal. These results are in line with those obtained by western blots. hOMSC subjected to either treatment A or B secreted higher levels of dopamine into the medium in comparison to naïve hOMSC (FIG. 5E). Treatment B-differentiated cells secreted higher amounts of dopamine, exhibiting a 4 and 10 fold increase, compared to treatment A-differentiated hOMSC or naïve hOMSC respectively. Moreover, B-differentiated hOMSC not challenged by KCl, failed to release dopamine into the medium, evidencing an ion-dependent release mechanism (FIG. 5F).

Figure 6G:
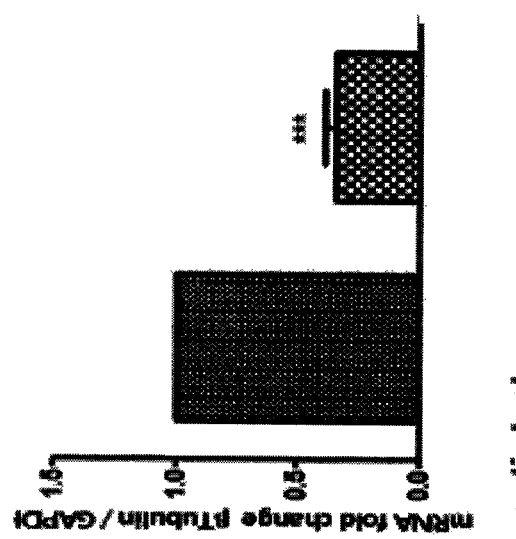
FIG. 6. Differentiated hOMSC exhibit an astrocyte-like phenotype.
FIGS. 6A and 6B illustrate by bright field microscopy the changes in hOMSC morphology from spindle-shape to astrocyte-like. Scale bar=100 μm.
FIGS. 6C and 6D depict by double immunofluorescence the increase in the expression of S100B and GFAP in the differentiated hOMSC. The nuclei are counterstained with DAPI. 6E, 6F and 6G—Real time PCR analysis indicate an increase in the expression of GFAP and glutamate transporter EAAT2 and a reduction in the expression of βIII-tubulin, respectively. Significance levels *p<0.05, **p<0.01.
Figure 6F:
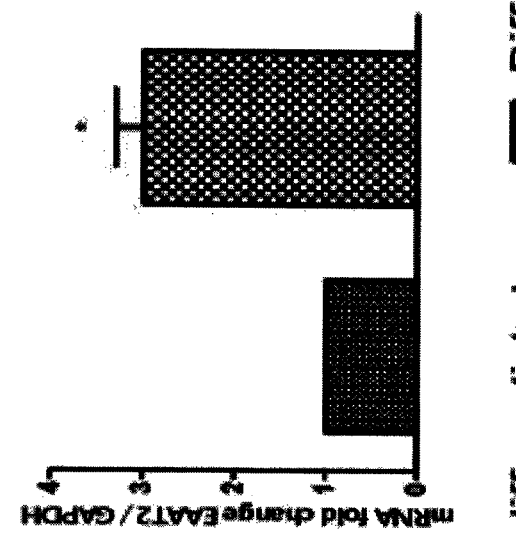
Figure 6E:
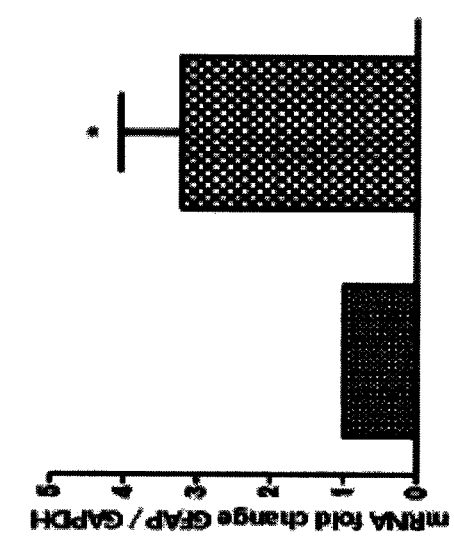

Example 7 hOMSC after Neuron Supporting Cells Differentiation (NSC) Differentiate into an Astrocyte-Like Phenotype—hOMSC-NS Following the two-step glial differentiation protocol as described above, the entire culture of induced hOMSC assumed substantial morphological changes to a neural-like morphology, resembling that of astrocytes (FIG. 6). These morphological changes include cell condensation from an initial fusiform morphology to the formation of multiple projections emerging from the cell body. These changes correlate with an increase in the expression of two classic astrocytic markers, GFAP and S100β at the gene and protein levels as evidenced by real time PCR and immunofluorescence analysis (FIG. 6A-D). Moreover, differentiated hOMSC showed increased levels of glutamate transporter EAAT2 (GLT-1) as well as a significant reduction in the transcription levels of the neuronal marker TUJ1, as compared to undifferentiated hOMSC (FIG. 6E-G). Collectively, the results point to the differentiation of hOMSC along the astrocyte-like phenotype.

Example 8

Figure 7A:
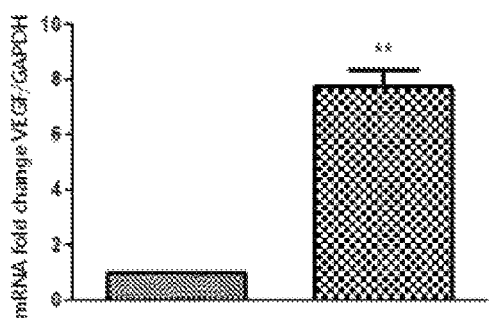
FIG. 7. Immunofluorescence of intracellular neurotrophic factors before (undifferentiated) and after differentiation (differentiated). mRNA levels of VEGF (7A) and BDNF (7B) were enhanced after differentiation protocol, as seen by real time PCR. Neurotrophic factor secretion was increased after differentiation, as seen by VEGF (7C) and BDNF (7D) conditioned medium ELISA analysis. Significance levels *p<0.05, p<0.01, *p<0.001. Scale bar=100 μm.
Figure 7B:
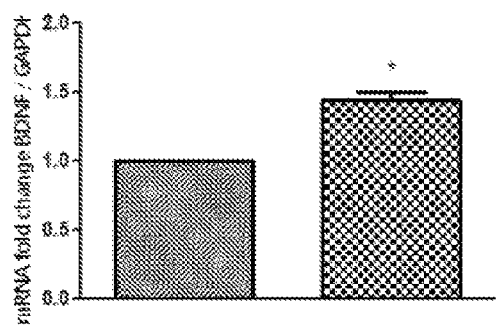
Figure 7C:
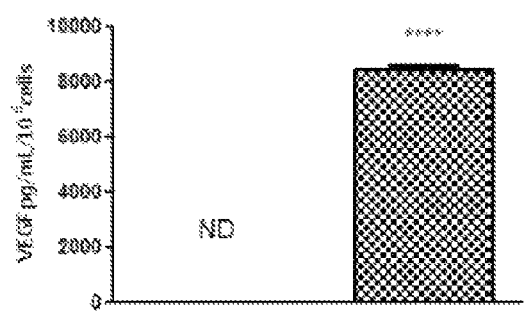
Figure 7D:
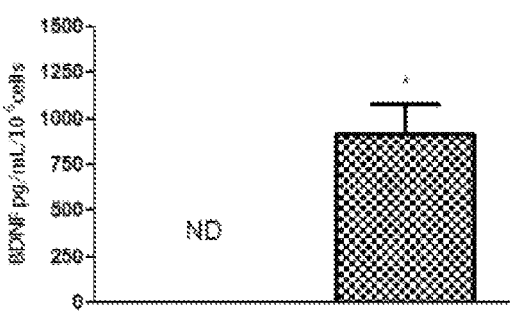

Differentiated hOMSC-NS Exhibit Enhanced Neurotrophic Factors Synthesis and Secretion hOMSC differentiation into astrocyte-like cells resulted in the expression of the neurotrophic factors BDNF, GDNF, IGF-1 and VEGF at the protein level as evidenced by immunofluorescence. At mRNA level, VEGF and BDNF were upregulated (FIG. 7A-B). ELISA analysis of the conditioned medium was performed to evaluate whether the increase in VEGF and BDNF synthesis is followed by their secretion. VEGF and BDNF secretion levels were strongly increased, reaching concentrations of approximately 8 ng/mL/106 cells and 1 ng/mL/106 cells respectively (FIG. 7C-D).

Example 9 hOMSC-NS Transplantation Ameliorates Sciatic Nerve Injury in Rats

Figure 8A:
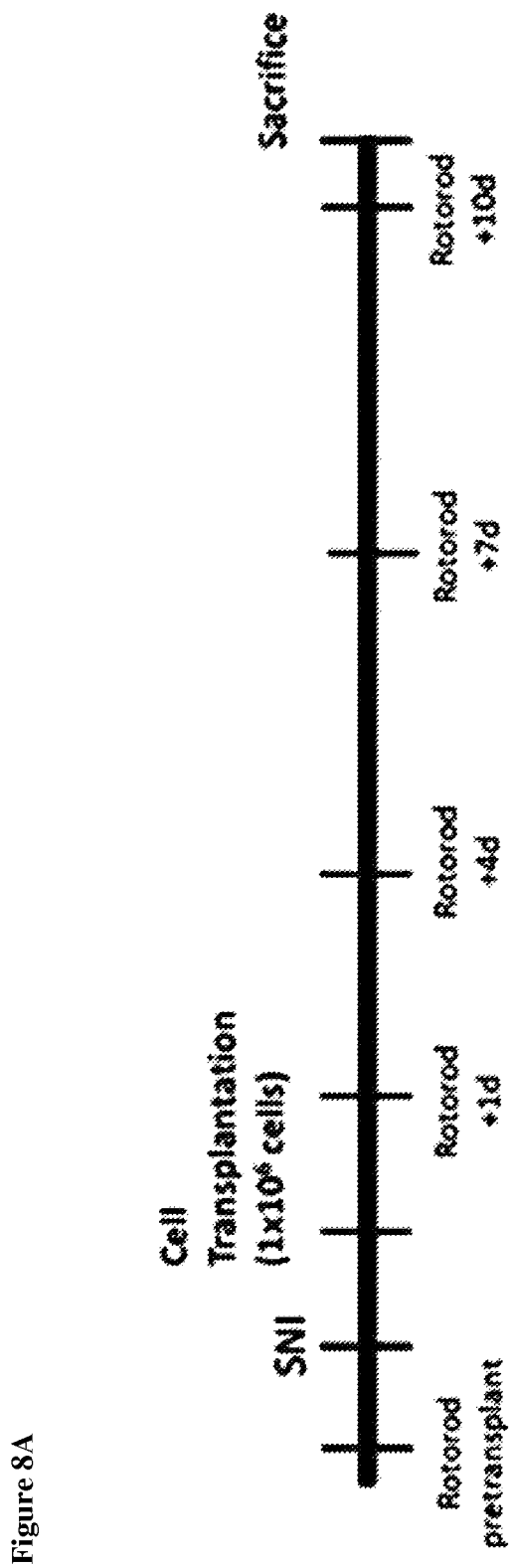
FIG. 8. Transplanted hOMSC-derived-NSs improve motor behavior of sciatic nerve injury affected rats. 8A) Cell transplantation and functional evaluation scheme. 8B) Transplantation of hOMSC-NSs (n=8), hOMSC (n=8) and saline (n=8) was performed 1 day after mechanical crush (day 0) of the right hind limb sciatic nerve. A volume of 100 μL containing $1 \times 10^6$ cells was inoculated 24 hr. after injury (day 1). Motor function/recovery was assessed by Rotarod test at days −1, 0, 2, 4, 6 and 10 and is presented as time spent on rod (seconds). The motoric function of the animals in the hOMSC-NS treated group was significantly higher than that of the naïve hOMSC and saline treated groups. Data is presented as Means+SEM, statistical analysis was performed using ANOVA repeated measures test with Tukeys multiple comparison posthoc test (p=0.0261).
Figure 8B:
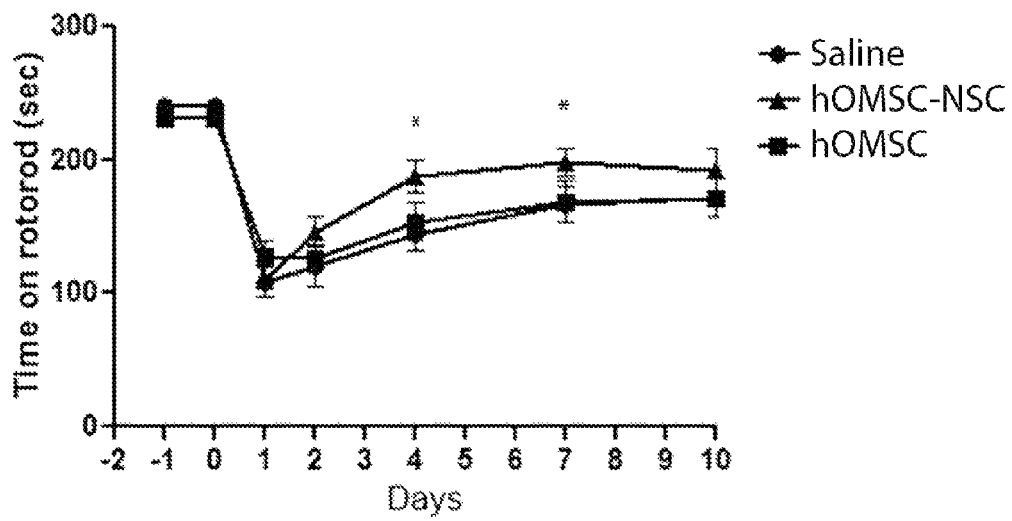

To assess the restorative potential of hOMSC-NS in vivo, a sciatic nerve injury experiment was performed in rats (FIG. 8A-B). The injury was done by a mechanical crush of the right hind limb sciatic nerve (day 0). One day after surgery three groups of rats (n=8/group) were injected into the affected area with a volume of 100 μL saline or with $1 \times 10^6$ hOMSC or with $1 \times 10^6$ hOMSC-NS. As demonstrated by the Rotor-rod test, a significant improvement in the motor function was achieved in the animals of the hOMSC-NS-transplanted group during the first stages of recovery compared to that of animals treated with naïve hOMSC or saline. This improvement was prominent and statistically significant ($p<0.05$) between days 1-7 after cell transplantation. No differences in the improvement of motor function were observed between the saline-treated and the naive hOMSC-treated groups ($p>0.05$).

Example 10

Transplantation of hOMSC-Derived DA-Like Neurons Ameliorates Motor Function in a Rat PD Model Since hOMSC differentiated according to treatment B protocol (hOMSC-DA) exhibited the highest similarity to dopaminergic neurons, the functional capacity of these cells was assessed in the hemiparkinsonian rat PD model. Saline-treated and hOMSC treated hemiparkinsonian rats served as controls. The in vivo results presented here are the combination of two independent experiments, given the low rate of damaged rats with net rotations>2/min. By this, we were sure that every animal which entered the experiment had severe dopaminergic neuron depletion in the affected hemisphere. The combination of both experiments was used only for drug-induced rotations (saline and hOMSC n=12, hOMSC-DA n=13) and not for cylinder or Rotarod tests (Table 2).

TABLE 2 hOMSC-DA transplantation in rat PD animal model data. Group performances of saline, hOMSC and hOMSC-DA in amphetamine-induced rotations (A), Rotarod (B) and cylinder test (C).

| A. Induced rotations Two Way Anova, $p < 0.0001$ | | | | | | | |
|---|---|---|---|---|---|---|---|
| | Saline n = 12 | | hOMSC n = 12 | | hOMSC-DA n = 13 | | |
| Time (weeks) | Mean (%) | SEM | Mean (%) | SEM | Mean (%) | SEM | p value |
| 0 | 100.0 | 0.0 | 100.0 | 0.0 | 100.0 | 0.0 | >0.05 |
| 1 | 125.5 | 12.6 | 94.7 | 7.1 | 58.1 | 5.4 | <0.05 |
| 4 | 141.7 | 10.5 | 123.6 | 9.1 | 84.0 | 8.0 | <0.05 |
| 8 | 165.5 | 15.0 | 124.9 | 10.7 | 87.4 | 10.4 | <0.05 |
| B. Rotorod Test Two Way Anova, $p = 0.0086$ | | | | | | | |
| | Saline n = 8 | | hOMSC n = 8 | | hOMSC-DA n = 9 | | |
| Time (weeks) | Mean (%) | SEM | Mean (%) | SEM | Mean (%) | SEM | p value |
| 0 | 59.7 | 2.8 | 61.7 | 5.5 | 61.2 | 5.4 | >0.05 |
| 1 | 62.8 | 9.5 | 69.9 | 4.9 | 99.4 | 5.1 | <0.05 |
| 2 | 76.6 | 10.1 | 67.8 | 6.3 | 107.3 | 8.9 | <0.05 |
| 4 | 89.7 | 10.0 | 81.2 | 9.1 | 122.1 | 13.9 | <0.05 |
| C. Cylinder test One Way Anova, $p = 0.0009$ | | | | | | | |
| | Saline n = 7 | | hOMSC n = 4 | | hOMSC-DA n = 9 | | |
| Time (weeks) | Mean (score) | SEM | Mean (score) | SEM | Mean (score) | SEM | p value |
| 3 | 0.79 | 0.03 | 0.81 | 0.08 | 0.55 | 0.04 | <0.05 |

Figure 9A:
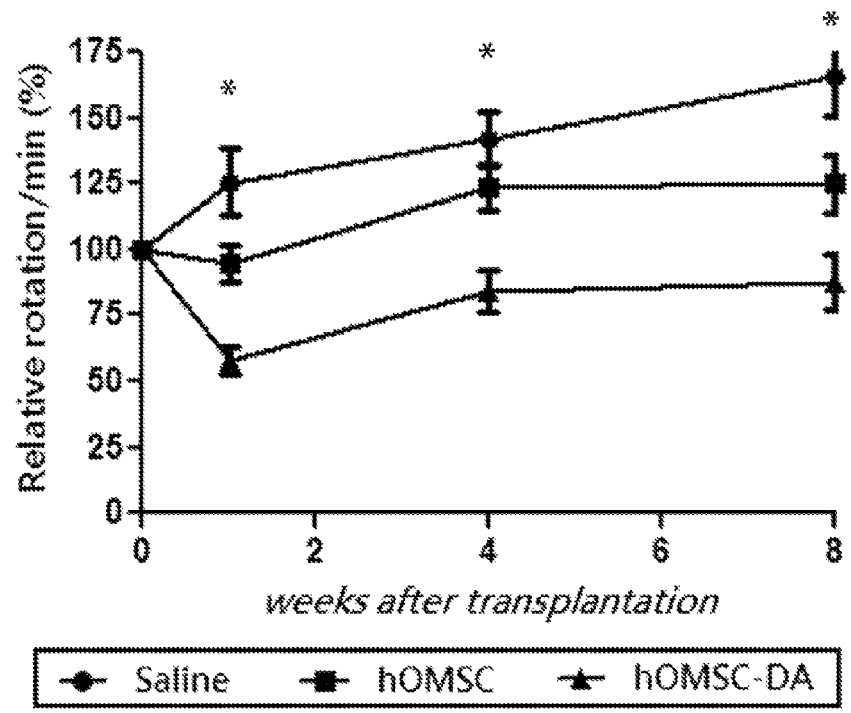
FIG. 9. hOMSC-DA transplantation ameliorates motor parameters in a rat PD model. Striatal transplantation of DA-hOMSC reduced amphetamine-induced rotations (9A), motor asymmetry (9B) and improved motor coordination (9C) in hemiparkinsonian rats (6-OHDA). Data is expressed as Mean±SEM. One Way (9B) and Two Way ANOVA (9A, 9C) statistical analysis was performed with Tukeys post hoc test. Significance levels *p<0.05, **p<0.01.

In the amphetamine-induced rotations tests following transplantation, we observed a robust reduction of 54%, 40% and 47% ($p<0.0001$) in weeks 1, 4 and 8 respectively, between hOMSC-DA and saline treated group ($p<0.05$) (FIG. 9A). Even though to a less extent, a similar significant reduction in the number of induced rotation was observed in the hOMSC-DA treated group compared to the naïve hOMSC treated one ($p<0.05$). A trend of reduction in the induced rotation was observed in animals treated with naive hOMSC that reached statistical significance compared to saline-treated animals at week 4 ($p<0.05$).

Figure 9B:
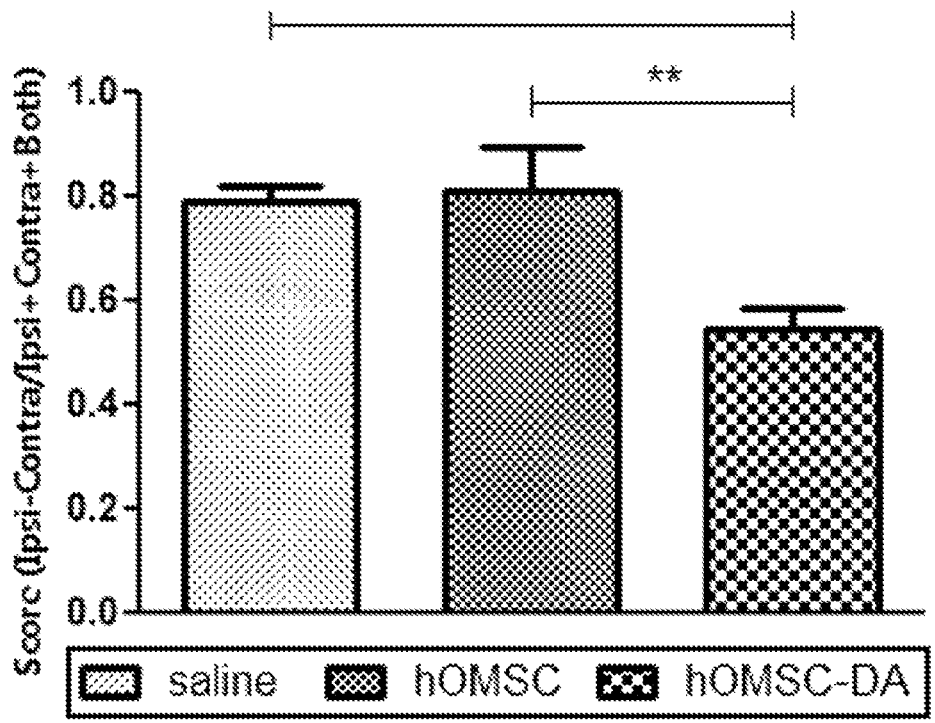

Motor asymmetry was assessed by the cylinder test three weeks after transplantation (saline n=7, hOMSC n=4, hOMSC-DA n=9). The more frequent use of the ipsilateral forelimb (unaffected) was evident in all the evaluated groups. No differences were observed between saline or naïve hOMSC treated rats in this respect (FIG. 9B). hOMSC-DA treated rats showed a significant reduction of 38% in motor asymmetry in comparison to the other two tested groups (p=0.0009). This data point to an increase in the use of the contralateral forelimb (affected) in the hOMSC-DA transplanted animals.

Figure 9C:
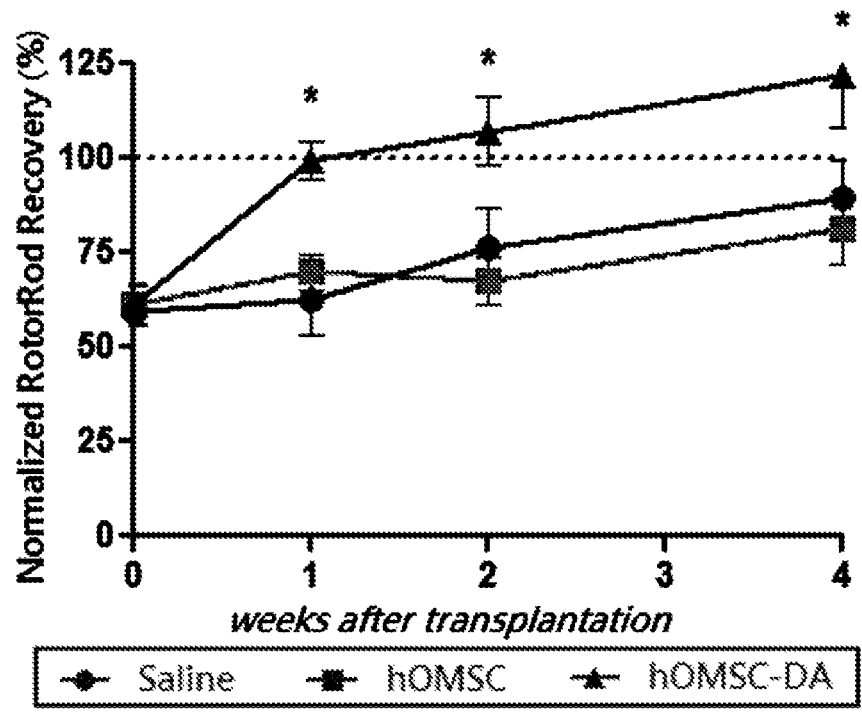

General motor coordination was also assessed by the Rotarod test (saline and hOMSC n=8, hOMSC-DA n=9) at weeks 1, 2 and 4 after transplantation (FIG. 9C). After the 6OHDA injury, a 40% reduction in the motor coordination was evidenced (p=0.0086). The results are expressed as percentage of the performance before injury. One week after transplantation, no recovery was observed in saline (62.7±9.4) or hOMSC (69.8±4.8) treated rats, whereas animals treated with hOMSC-DA presented almost a full recovery in regard to rotor-rod test (99.4±5.1, pvalue<0.05). In the second and fourth week after transplantation, the groups displayed an improvement in their performance possibly due to a learning curve. However, the difference between the hOMSC-DA treated group and the other two groups remained unchanged during this experimental period (FIG. 9C).

Figure 10A:
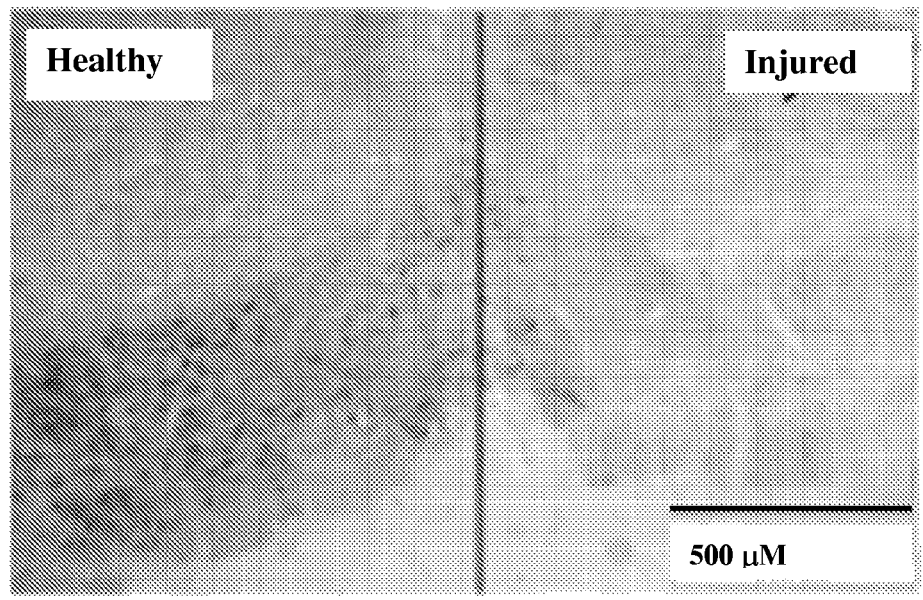
FIG. 10. hOMSC-DA transplanted rats show striatal TH expression and increased hemisphere DA content. Substantia nigra TH immunohistochemistry developed with DAB show DA depletion in the affected hemisphere (10A). Scale bar=500 μm. Hemisphere DA (10B) and 5HT (10C) quantification by HPLC show increased levels of dopamine in hOMSC-DA transplanted animals, while no serotonin modification was observed. Data is presented as Mean±SEM and ANOVA statistical analysis was performed. Significance levels *p<0.05, p<0.01, *p<0.001.
Figure 10B:
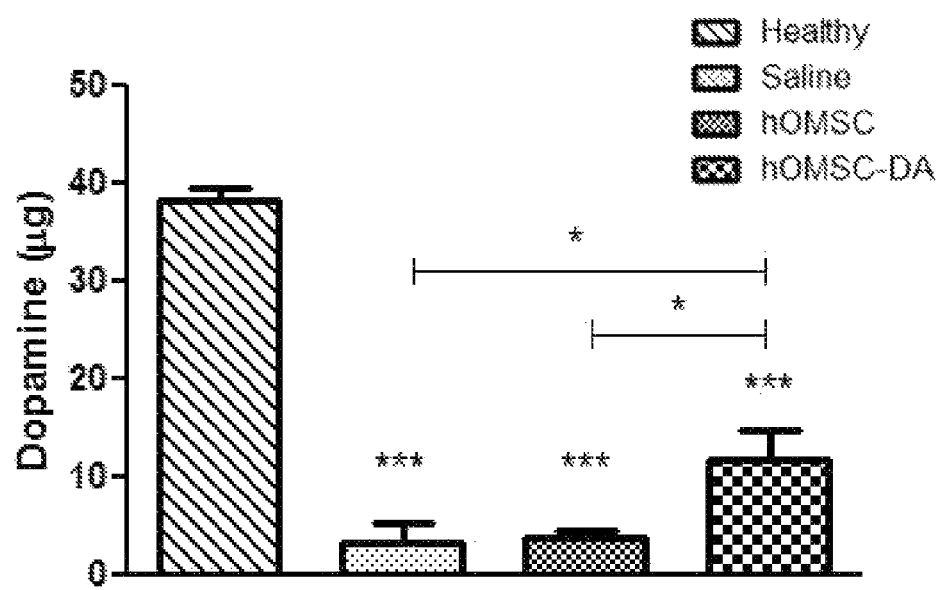
Figure 10C:
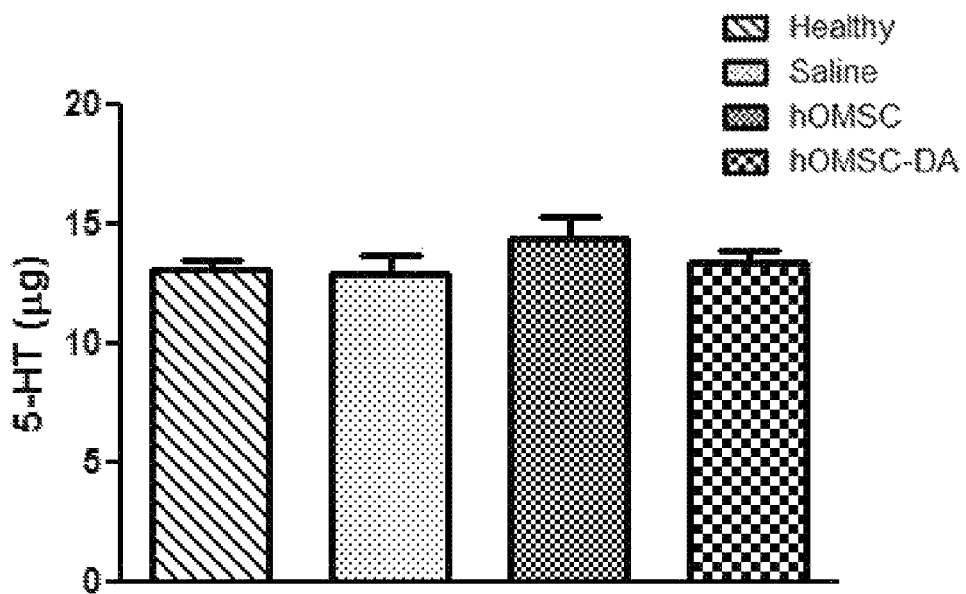

Example 11 hOMSC-DA-Like Neurons Maintains their Phenotype Ten Weeks after Intra-Striatal Transplantation Ten weeks after cell transplantation rats of the 3 groups were sacrificed. Brains were obtained for immunodetection of dopaminergic related factors in the striatum and substantia nigra. Identification of the transplanted hOMSC and their capacity to express TH in the striatum as well as the biochemical quantification of dopamine and serotonin in the healthy and treated hemispheres was performed. PKH26 positive cells were identified in the striatum of naïve hOMSC and in hOMSC-DA treated animals. TH was not detected in the substantia nigra of the injured hemispheres (FIG. 10A) indicating the destruction of dopaminergic neurons by 6OHDA in these sites, and supporting the impaired motor function observed in the functional assays described above. TH was detected in the healthy striatum of each group and in the injured striatum of the hOMSC-DA treated animals. However TH was not identified in the injured striatum of saline and hOMSC treated rats. TH was localized in PKH26 positive cells, indicating that hOMSC-DA cells express TH. HPLC analysis of dopamine and serotonin levels in the health and injured hemisphere indicated a reduction in the dopamine level in all the injured hemispheres compared to those in the healthy ones 11.8±3.0 µg, 3.8±2.2 µg and 3.4±1.8 µg in the hOMSC-DA, naive hOMSC and saline treated hemispheres, respectively vs. 38.2±3.2 µg in the healthy hemispheres (FIG. 10B). However, the dopamine level in the hOMSC-DA treated injured hemispheres was by 3 folds higher than the other 2 groups of injured hemispheres, Serotonin (5HT) levels were similar in all the hemispheres (FIG. 10C) indicating that the changes observed in the dopamine levels were specific.

Summary for DA Cells:

A stem cells source with great advantages for PD clinical translation is provided. It was demonstrated for the first time that SC derived from the human oral mucosa can be successfully differentiated into DA-like neurons by a medium based protocol. Obtained cells showed induction of typical DA markers, secreted dopamine and maintained the ability to ameliorate a rat PD model following intra-striatal transplantation. Moreover, improvements where evidenced by three independent motor-behavioral tests, being positively correlated with TH and dopamine striatal increase. By non-invasive procedures, access to a neural crest-derived stem cells reservoir was gained. hOMSC can be rapidly expanded in culture, their properties are not-affected by donors' age, are capable of surviving and integrating into the host tissue and demonstrated to have neuronal prone characteristics. The present study thus discloses that generated hOMSC-DA should be clinically considered for autologous cell replacement therapy in PD.

Example 12

Figure 11A:
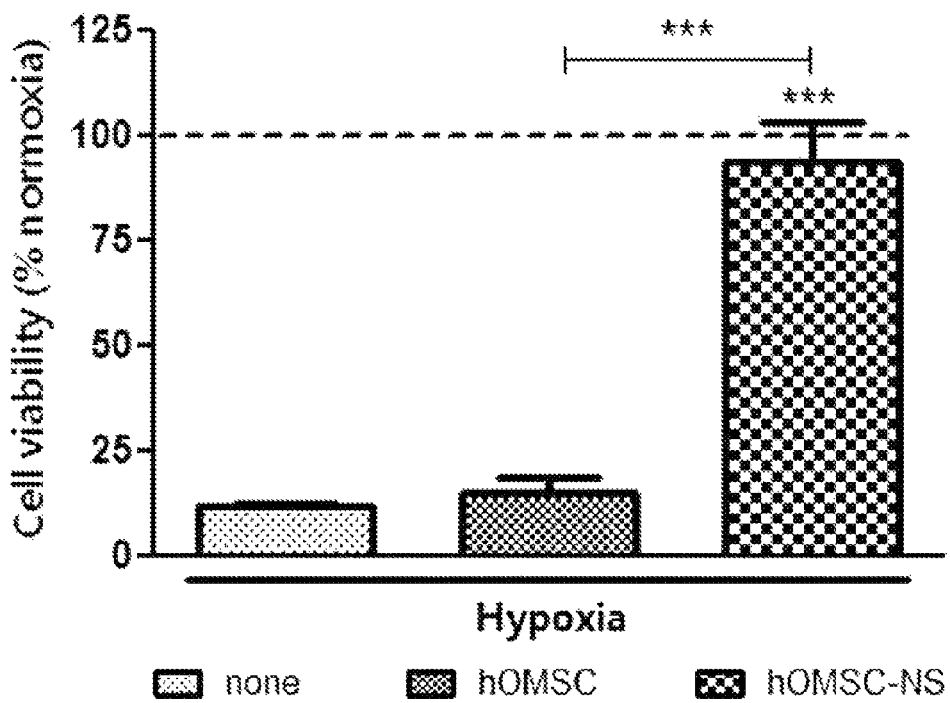
FIG. 11. Conditioned medium from differentiated hOMSC protects motor neurons from hypoxia and oxidative stress. Motor neurons (NSC34 cell line) were incubated for 72 hr. under hypoxic conditions (11A) or 48 hr. with hydrogen peroxide (25 μM) (11B). Treatments include serum free conditions (none) and conditioned medium from undifferentiated (hOMSC) or differentiated hOMSC (hOMSC-NSs). Data is presented as percentage (Means±SEM) of cells without insult. Significance levels are *p<0.05, p<0.01, *p<0.001.
Figure 11B:
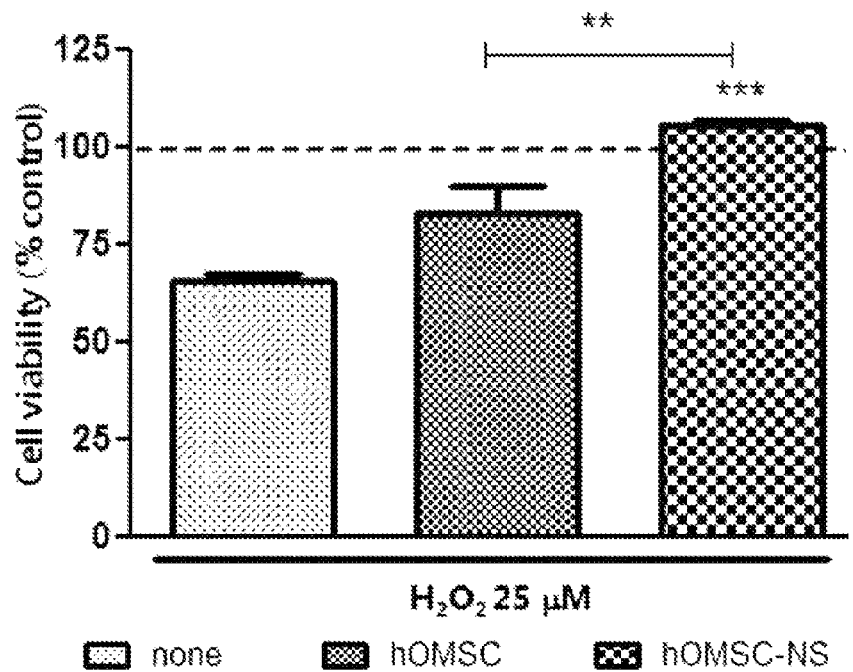

Conditioned Medium of Differentiated hOMSC Protects Motorneurons from Hypoxia and Oxidative Stress Induced-Cell Death In Vitro To evaluate the potential of differentiated hOMSC to protect neuronal cultures from hypoxia and oxidative stress induced-cell death, the motorneuron cell line NSC34 38 was used. After 72 hours of hypoxia condition (FIG. 11A) a significant decrease in cell viability of 11.85±0.82% and 15.23±3.87% as compared to cells grown under normoxia conditions was observed in the serum free cultured NSC34 as well as in the NSC34 cultures maintained in conditioned medium of naïve hOMSC respectively. In contrast, NSC34 treated with conditioned medium from differentiated hOMSC cultures exhibited survival rates comparable to those of cells cultured under normoxia conditions 93.8±9% (p<0.001). The relative survival rate of NSC34 motorneurons that were exposed to oxidative stress for 48 hr. ($H_2O_2$ 25 µM, FIG. 11B) was significantly higher in cell cultures maintained in conditioned medium of differentiated hOMSC (105.9±1.1 compared to untreated controls) than that of motorneuron cultures maintained in serum free and that of undifferentiated hOMSC (65.88±1.74% and 83.47±6.8% respectively). Because of the neuroprotective capacity of the hOMSC differentiated cells they will be refereed herein as hOMSC-derived neuron supporting cells (hOMSC-NS).

Example 13 hOMSC-NS Maintain their Phenotype In Vivo

Figure 12A:
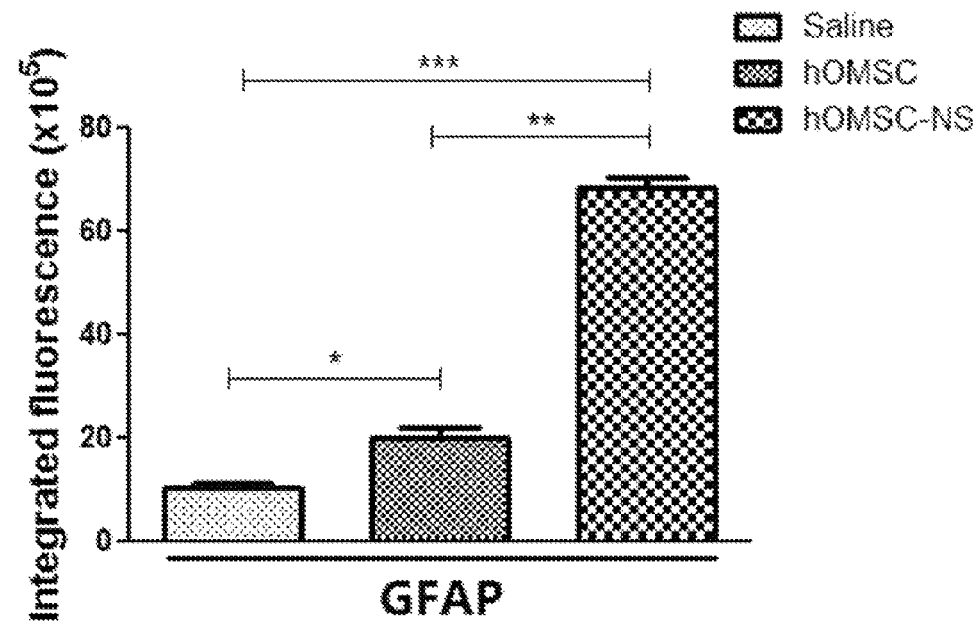
FIG. 12. hOMSC-NSs maintain phenotype and NTFs secretion in vivo. Muscle sections of sciatic nerve injured rats transplanted with saline, hOMSC or hOMSC-NSs. Integrated density of fluorescence as fluorescence estimation was calculated for GFAP (A), VEGF (B) and BDNF (C) using Image J software. One Way ANOVA (pvalue<0.0001, pvalue<0.001, pvalue<0.004, for J, K and L respectively). Tukey's multiple comparison posthoc test was used, significance levels *p<0.05, p<0.01, *p<0.001.
Figure 12B:
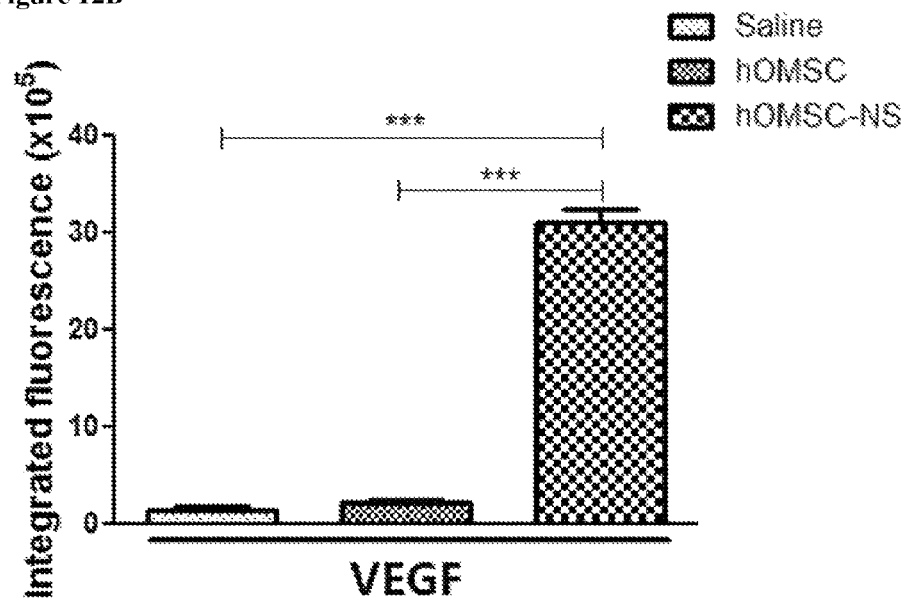
Figure 12C:
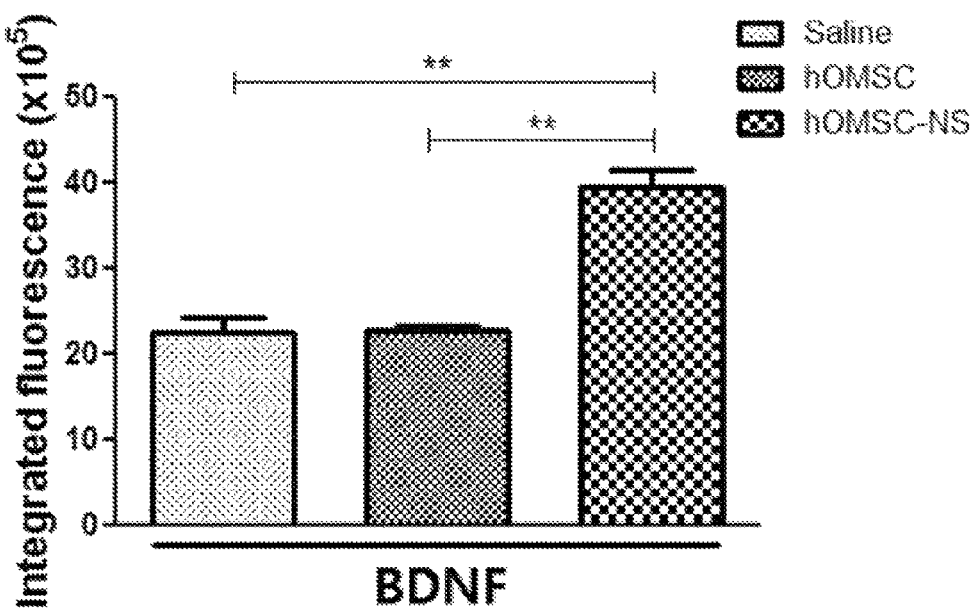

To test the fate of the transplanted cells, the inoculated muscular area and its surrounding were examined by histochemistry and immunofluorescence. Undifferentiated and differentiated cells were detected in the assumed inoculated areas only in the transplanted animals. Prussian blue staining revealed blue spots indicating the presence of cells which were labeled with superparagmagnetic iron oxide (SPIO) before transplantation. Moreover, immunofluorescence analysis confirmed the presence of human nuclei (HuNu) positive cells in cell-transplanted muscles but no signal was observed in the saline injected muscle tissue. Differentiated cells maintained their capacity of secreting neurotrophic factors and their astrocyte-like phenotype in vivo as evidenced by the expression of BDNF, VEGF and GFAP, respectively. Colocalization of GFAP and VEGF in the hOMSC-NS transplanted muscles indicated that GFAP positive cells are actively secreting VEGF in the vicinity of the injured nerve 10 days following their transplantation in vivo. Furthermore, we observed colocalization of human nuclear antigen (HuNu) with BDNF in NS transplanted sections and a significant increase in BDNF signal in comparison to sections obtained from animals treated with saline or naïve hOMSC. A low BDNF signal was also observed in in the sections obtained from the control groups, probably due to endogenous BDNF synthesis by muscle progenitor cells 39, 40. Notably, naïve hOMSC also express low levels of GFAP. Estimation of the GFAP-positive areas (FIG. 12A) indicate that sections derived from hOMSC-NS transplanted animals exhibited a 3.3 and 6 fold increase in relative fluorescence compared to sections obtained from naïve hOMSC and saline treated animals, respectively ($p<0.0001$). Similarly, the relative fluorescence of VEGF-positive areas in section obtained from hOMSC-NS treated animals were by 13.8 and 16.6 fold higher than that observed in sections obtained from animals transplanted with naive hOMSC or treated with saline, respectively ($p<0.001$) (FIG. 12B). BDNF-positive areas exhibited a similar pattern, even though the differences in the relative fluorescence between the groups were smaller than those observed for the previous two markers (FIG. 12C).

Example 14

Transplanted hOMSC-NS Preserved Neuromuscular Junctions after Injury

Figure 13:
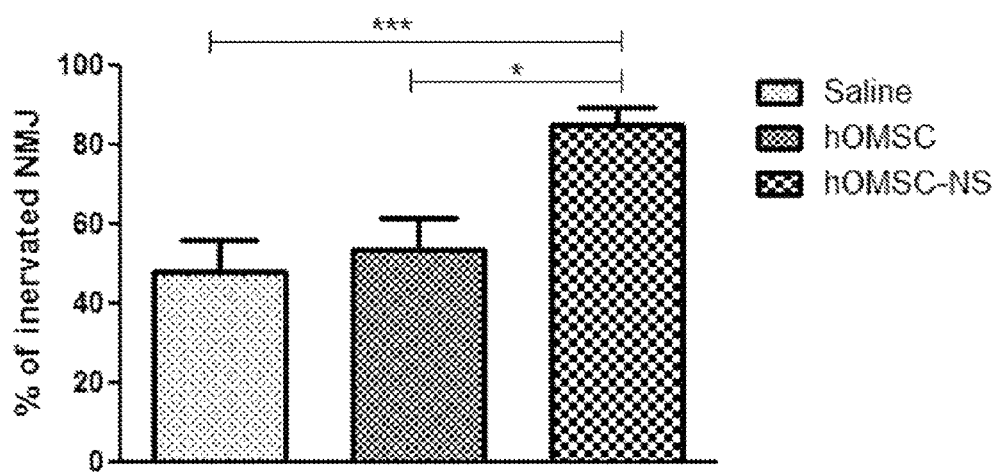
FIG. 13. Transplanted hOMSC-NS reduced NMJs denervation. Ten days after sciatic nerve crush and injection of saline, hOMSC or hOMSC-NS, hind limbs muscle sections were double stained using antibodies against alpha bungarotoxin and synaptophysin antibodies to measure functional NMJ. Quantification of innervated NMJs is expressed as percentage of preserved NMJ ($\alpha BTX^+SYP^+$) over total ($\alpha BTX^+SYP^+ + \alpha BTX^+ + SYP^+$). (n=4, means±SEM, *p<0.05, ***p<0.0001 determined by ANOVA and Tukeys posthoc analysis).

Ten days after the sciatic nerve crush, NMJs were evaluated and counted within the gastrocnemius and tibialis muscles in the crushed area in animals of the three groups. Colocalization of acetylcholine receptor ligand, alpha bungarotoxin ($\alpha$-BTX) and of the post synaptic protein synaptophysin (SYP) pointed to preserved and innervated NMJ. Staining for $\alpha$-BTX or SYP alone was considered as denervated NMJ. Evaluation of the NMJ was plotted in bar chart and expressed as percentage of preserved NMJ counts over total counted ($\alpha$BTX+SYP++$\alpha$BTX++SYP+, FIG. 13). It was found that in gastrocnemius and tibialis muscles transplanted with hOMSC-NS, 89.4±4.6% of the NMJs were innervated. In contrast, in muscles transplanted with hOMSC or saline only 53.5±8.3% and 48.2±8% of the NMJs were innervated, respectively. Statistical analysis demonstrate significance (ANOVA with and Tukeys posthoc analysis $p=0.0006$) between the hOMSC-NS treated group and the other two groups, which did not differ from each other.

Summary for NS Cells

It is herein shown for the first time that cells with enhanced neurotrophic factors secretion and therapeutic relevance, can be successfully obtained through hOMSC differentiation these cells significantly accelerated the regeneration of the sciatic nerve after crush injury. Considering the many advantages of using oral mucosa stem cells and the results showed here, hOMSC emerge as a novel stem cell population for autologous cell therapy of peripheral nerve injuries and possibly other neuropathies.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method for inducing selective differentiation of oral mucosa stem cells (OMSC) into neuron-supporting glial cells, comprising:
   (a) obtaining oral mucosa stem cells (OMSC) from oral mucosa;
   (b) incubating the OMSC of (a) in a pre-differentiating medium, comprising N-2 supplement, basic fibroblast growth factor 2 (bFGF) and epidermal growth factor (EGF); and
   (c) after incubation of the OMSC in (b), replacing the pre-differentiation medium of (b) with a differentiating medium comprising dibutyryl cyclic adenosine monophosphate (dbcAMP), IBMX (3-Isobutyl-1-methylxanthine), neuregulin, and platelet-derived growth factor (PDGF) and incubating the OMSC from (b) in the differentiation medium to selectively differentiate OMSC into neuron-supporting glial cells secreting neurotrophic factors.

2. The method according to claim 1, wherein the OMSC are incubated in a differentiating medium comprising 0.1-10 mM dbcAMP, 0.1-10 mM IBMX, 5-500 ng/ml neuregulin, and 0.1-10 ng/ml PDGF for about 48-96 hours, for about 24-120 hours.

3. The method according to claim 1, wherein the OMSC are incubated in a differentiating medium comprising about 0.5-2 mM dbcAMP, about 0.2-1 mM IBMX, about 20-100 ng/ml neuregulin, and about 0.5-2 ng/ml PDGF for about 48-96 hours.

4. The method according to claim 1, wherein the OMSC are incubated in a differentiating medium comprising about 1 mM dbcAMP, about 0.5 mM IBMX, about 50 ng/ml neuregulin, and about 1 ng/ml PDGF for about 48-96 hours.

5. The method according to claim 1, in which OMSC, separate from the OMSC selectively differentiating into neuron-supporting glial cells, are induced to selectively differentiate into a separate population of dopaminergic neural cells, further comprising:
   (d) incubating a separate population of OMSC obtained from oral mucosa in a pre-differentiation medium comprising N2, bFGF and EGF; and
   (e) after incubation of the OMSC in (d), replacing the pre-differentiation medium of (d) with a differentiation medium comprising a plurality of agents selected from the group consisting of B27, IBMX (3-Isobutyl-1-methylxanthine), dbcAMP, ascorbic acid, BDNF, Sonic Hedgehog (SHH), Wnt-1, fibroblast growth factor-8 (FGF-8), and bFGF and incubating the OMSC from (d) in the differentiation medium for a duration of at least 2 days to selectively differentiate the separate population of OMSC into a separate population of dopaminergic neural cells, so that when mixed with the OMSC selectively differentiated into neuron-supporting glial cells the mixture forms a mixed population of selectively differentiated neuron-supporting glial cells and selectively differentiated dopaminergic neural cells .

6. The method according to claim 5, wherein the OMSC are incubated in a differentiating medium comprising 0.1-5% B27, 0.1-5 mM IBMX, 0.1-10 mM dbcAMP, 10-500 μM ascorbic, and 10-500 ng/ml BDNF, for about 2-4 days.

7. The method according to claim 5, wherein the OMSC are incubated in a differentiating medium comprising 0.5% B27, 85-750 ng/mL Sonic Hedgehog, 30-300 ng/mL Wnt-1, 30-300 ng/mL FGF-8, 15-150 ng/mL BDNF, 15-150 ng/mL bFGF, and 65-600 ng/mL ascorbic acid, for at least 4 days.

8. The method according to claim 5, wherein step (d) is performed for duration of about 48-96 hours.

9. The method according to claim 5, wherein step (e) is performed for at least 12 days in a differentiating medium comprising 0.1-5% B27, 85-750 ng/mL Sonic Hedgehog, 30-300 ng/mL Wnt-1, 30-300 ng/mL FGF-8, 15-150 ng/mL BNDF, 15-150 ng/mL bFGF, and 65-600 ng/mL ascorbic acid.

10. The method according to claim 5, wherein the OMSC are incubated in a differentiating medium comprising 0.5% B27, 100-400 ng/mL Sonic Hedgehog, 50-150 ng/mL Wnt-1, 50-150 ng/mL FGF-8, 25-100 ng/mL BDNF, 25-100 ng/mL bFGF, and 100-400 ng/mL of ascorbic acid for 13 days.

\* \* \* \* \*

SEQUENCE LISTING

```
<160> NUMBER OF SEQ ID NOS: 38

<210> SEQ ID NO 1
<211> LENGTH: 19
<212> TYPE: DNA
<213> ORGANISM: Artificial
<220> FEATURE:
<223> OTHER INFORMATION: primer

<400> SEQUENCE: 1
cgacagtcag ccgcatctt                                                   19

<210> SEQ ID NO 2
<211> LENGTH: 21
<212> TYPE: DNA
<213> ORGANISM: Artificial
<220> FEATURE:
<223> OTHER INFORMATION: primer

<400> SEQUENCE: 2
ccaatacgac caaatccgtt g                                                21
```

-continued

```
<210> SEQ ID NO 3
<211> LENGTH: 21
<212> TYPE: DNA
<213> ORGANISM: Artificial
<220> FEATURE:
<223> OTHER INFORMATION: primer

<400> SEQUENCE: 3
cctgcaggaa ggtgagagag a                                              21

<210> SEQ ID NO 4
<211> LENGTH: 20
<212> TYPE: DNA
<213> ORGANISM: Artificial
<220> FEATURE:
<223> OTHER INFORMATION: primer

<400> SEQUENCE: 4
tggacgacac ggacactcag                                                20

<210> SEQ ID NO 5
<211> LENGTH: 19
<212> TYPE: DNA
<213> ORGANISM: Artificial
<220> FEATURE:
<223> OTHER INFORMATION: primer

<400> SEQUENCE: 5
caggagaacc ccaagatgc                                                 19

<210> SEQ ID NO 6
<211> LENGTH: 17
<212> TYPE: DNA
<213> ORGANISM: Artificial
<220> FEATURE:
<223> OTHER INFORMATION: primer

<400> SEQUENCE: 6
gcagccgctt agcctcg                                                   17

<210> SEQ ID NO 7
<211> LENGTH: 24
<212> TYPE: DNA
<213> ORGANISM: Artificial
<220> FEATURE:
<223> OTHER INFORMATION: primer

<400> SEQUENCE: 7
caactaagat gttcgtcaaa tccg                                           24

<210> SEQ ID NO 8
<211> LENGTH: 21
<212> TYPE: DNA
<213> ORGANISM: Artificial
<220> FEATURE:
<223> OTHER INFORMATION: primer

<400> SEQUENCE: 8
ccttcaactc caaggtctcg g                                              21

<210> SEQ ID NO 9
<211> LENGTH: 19
<212> TYPE: DNA
<213> ORGANISM: Artificial
<220> FEATURE:
<223> OTHER INFORMATION: primer
```

```
<400> SEQUENCE: 9
agcagggtga tcgcacaac                                              19

<210> SEQ ID NO 10
<211> LENGTH: 23
<212> TYPE: DNA
<213> ORGANISM: Artificial
<220> FEATURE:
<223> OTHER INFORMATION: primer

<400> SEQUENCE: 10
acgccactga caagaaagca cta                                         23

<210> SEQ ID NO 11
<211> LENGTH: 22
<212> TYPE: DNA
<213> ORGANISM: Artificial
<220> FEATURE:
<223> OTHER INFORMATION: primer

<400> SEQUENCE: 11
gttattcgga tcgtccatcc tc                                          22

<210> SEQ ID NO 12
<211> LENGTH: 20
<212> TYPE: DNA
<213> ORGANISM: Artificial
<220> FEATURE:
<223> OTHER INFORMATION: primer

<400> SEQUENCE: 12
cgccttgagt ctctgcagct                                             20

<210> SEQ ID NO 13
<211> LENGTH: 21
<212> TYPE: DNA
<213> ORGANISM: Artificial
<220> FEATURE:
<223> OTHER INFORMATION: primer

<400> SEQUENCE: 13
gttcgctgaa aagaagcag c                                            21

<210> SEQ ID NO 14
<211> LENGTH: 21
<212> TYPE: DNA
<213> ORGANISM: Artificial
<220> FEATURE:
<223> OTHER INFORMATION: primer

<400> SEQUENCE: 14
tctggaaggt cgcctctagc t                                           21

<210> SEQ ID NO 15
<211> LENGTH: 22
<212> TYPE: DNA
<213> ORGANISM: Artificial
<220> FEATURE:
<223> OTHER INFORMATION: primer

<400> SEQUENCE: 15
ggatggtcaa agaagtggtt cg                                          22

<210> SEQ ID NO 16
<211> LENGTH: 19
```

```
<212> TYPE: DNA
<213> ORGANISM: Artificial
<220> FEATURE:
<223> OTHER INFORMATION: primer

<400> SEQUENCE: 16
cctgtgggct cttcggttt                                                 19

<210> SEQ ID NO 17
<211> LENGTH: 20
<212> TYPE: DNA
<213> ORGANISM: Artificial
<220> FEATURE:
<223> OTHER INFORMATION: primer

<400> SEQUENCE: 17
ccgccctggt actcttggat                                                20

<210> SEQ ID NO 18
<211> LENGTH: 21
<212> TYPE: DNA
<213> ORGANISM: Artificial
<220> FEATURE:
<223> OTHER INFORMATION: primer

<400> SEQUENCE: 18
tccccttctg actctctggc t                                              21

<210> SEQ ID NO 19
<211> LENGTH: 20
<212> TYPE: DNA
<213> ORGANISM: Artificial
<220> FEATURE:
<223> OTHER INFORMATION: primer

<400> SEQUENCE: 19
ctggagccat agacggcatc                                                20

<210> SEQ ID NO 20
<211> LENGTH: 19
<212> TYPE: DNA
<213> ORGANISM: Artificial
<220> FEATURE:
<223> OTHER INFORMATION: primer

<400> SEQUENCE: 20
ccgcgtcaat ccaaacaga                                                 19

<210> SEQ ID NO 21
<211> LENGTH: 20
<212> TYPE: DNA
<213> ORGANISM: Artificial
<220> FEATURE:
<223> OTHER INFORMATION: primer

<400> SEQUENCE: 21
tgcctcacac ggagactgtc                                                20

<210> SEQ ID NO 22
<211> LENGTH: 20
<212> TYPE: DNA
<213> ORGANISM: Artificial
<220> FEATURE:
<223> OTHER INFORMATION: primer

<400> SEQUENCE: 22
```

-continued agtgggttgt ttgcctttgg                                          20

<210> SEQ ID NO 23
<211> LENGTH: 21
<212> TYPE: DNA
<213> ORGANISM: Artificial
<220> FEATURE:
<223> OTHER INFORMATION: primer

<400> SEQUENCE: 23
cgagggtgca ggtatggttt a                                        21

<210> SEQ ID NO 24
<211> LENGTH: 20
<212> TYPE: DNA
<213> ORGANISM: Artificial
<220> FEATURE:
<223> OTHER INFORMATION: primer

<400> SEQUENCE: 24
tcccgagctg gagatgtctt                                          20

<210> SEQ ID NO 25
<211> LENGTH: 18
<212> TYPE: DNA
<213> ORGANISM: Artificial
<220> FEATURE:
<223> OTHER INFORMATION: primer

<400> SEQUENCE: 25
ccagcaatga ccatgaag                                            18

<210> SEQ ID NO 26
<211> LENGTH: 18
<212> TYPE: DNA
<213> ORGANISM: Artificial
<220> FEATURE:
<223> OTHER INFORMATION: primer

<400> SEQUENCE: 26
aggccaccca tgagtagg                                            18

<210> SEQ ID NO 27
<211> LENGTH: 18
<212> TYPE: DNA
<213> ORGANISM: Artificial
<220> FEATURE:
<223> OTHER INFORMATION: primer

<400> SEQUENCE: 27
ggctgaaacc agcgactg                                            18

<210> SEQ ID NO 28
<211> LENGTH: 17
<212> TYPE: DNA
<213> ORGANISM: Artificial
<220> FEATURE:
<223> OTHER INFORMATION: primer

<400> SEQUENCE: 28
aggctcctgc gtgtctg                                             17

<210> SEQ ID NO 29
<211> LENGTH: 24
<212> TYPE: DNA
<213> ORGANISM: Artificial

```
<220> FEATURE:
<223> OTHER INFORMATION: primer

<400> SEQUENCE: 29
caaatatgcc agaggattat cctg                                              24

<210> SEQ ID NO 30
<211> LENGTH: 24
<212> TYPE: DNA
<213> ORGANISM: Artificial
<220> FEATURE:
<223> OTHER INFORMATION: primer

<400> SEQUENCE: 30
gccatttgtt tatctggtga cctt                                              24

<210> SEQ ID NO 31
<211> LENGTH: 21
<212> TYPE: DNA
<213> ORGANISM: Artificial
<220> FEATURE:
<223> OTHER INFORMATION: primer

<400> SEQUENCE: 31
agctccgggt tggtatactg g                                                 21

<210> SEQ ID NO 32
<211> LENGTH: 20
<212> TYPE: DNA
<213> ORGANISM: Artificial
<220> FEATURE:
<223> OTHER INFORMATION: primer

<400> SEQUENCE: 32
cctggtggaa cttctttgcg                                                   20

<210> SEQ ID NO 33
<211> LENGTH: 19
<212> TYPE: DNA
<213> ORGANISM: Artificial
<220> FEATURE:
<223> OTHER INFORMATION: primer

<400> SEQUENCE: 33
catgctggac ccaagctca                                                    19

<210> SEQ ID NO 34
<211> LENGTH: 24
<212> TYPE: DNA
<213> ORGANISM: Artificial
<220> FEATURE:
<223> OTHER INFORMATION: primer

<400> SEQUENCE: 34
gacattacgc tatgcacctc agtg                                              24

<210> SEQ ID NO 35
<211> LENGTH: 19
<212> TYPE: DNA
<213> ORGANISM: Artificial
<220> FEATURE:
<223> OTHER INFORMATION: primer

<400> SEQUENCE: 35
tagagggcga ggagaaccg                                                    19
```

```
<210> SEQ ID NO 36
<211> LENGTH: 22
<212> TYPE: DNA
<213> ORGANISM: Artificial
<220> FEATURE:
<223> OTHER INFORMATION: primer

<400> SEQUENCE: 36
gtggccttct gacacagact tg                                              22

<210> SEQ ID NO 37
<211> LENGTH: 18
<212> TYPE: DNA
<213> ORGANISM: Artificial
<220> FEATURE:
<223> OTHER INFORMATION: primer

<400> SEQUENCE: 37
cgaaggcctg cagagacc                                                   18

<210> SEQ ID NO 38
<211> LENGTH: 22
<212> TYPE: DNA
<213> ORGANISM: Artificial
<220> FEATURE:
<223> OTHER INFORMATION: primer

<400> SEQUENCE: 38
agggtatact cctgctccat gc                                              22
```